United States Patent
Victoria et al.

(10) Patent No.: US 6,207,160 B1
(45) Date of Patent: *Mar. 27, 2001

(54) APL IMMUNOREACTIVE PEPTIDES, CONJUGATES THEREOF AND METHODS OF TREATMENT FOR APL ANTIBODY-MEDIATED PATHOLOGIES

(75) Inventors: Edward Jess Victoria, San Diego; David Matthew Marquis, Encinitas; David S. Jones; Lin Yu, both of San Diego, all of CA (US)

(73) Assignee: La Jolla Pharmaceutical Company, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/660,092

(22) Filed: Jun. 6, 1996

Related U.S. Application Data

(63) Continuation-in-part of application No. 08/482,651, filed on Jun. 7, 1995, now Pat. No. 5,874,409.

(51) Int. Cl.[7] .................. A61K 39/385; A61K 38/04
(52) U.S. Cl. ................... 424/185.1; 424/193.1; 424/280.1; 514/11; 514/14; 514/15; 514/16; 530/403
(58) Field of Search ................ 514/14–16, 11; 424/184.1, 185.1, 280.1, 193.1; 530/403

(56) References Cited

U.S. PATENT DOCUMENTS

| | | |
|---|---|---|
| 4,191,668 | 3/1980 | Katz . |
| 4,650,675 | 3/1987 | Borel et al. . |
| 4,751,181 | 6/1988 | Keene . |
| 5,126,131 | 6/1992 | Dintzis et al. . |
| 5,162,515 | 11/1992 | Conrad et al. ............... 536/26.1 |
| 5,268,454 | 12/1993 | Barstad et al. .............. 424/193.1 |
| 5,276,013 | 1/1994 | Conrad et al. ................... 514/2 |
| 5,344,758 | 9/1994 | Krilis et al. ................... 435/7.1 |
| 5,370,871 | 12/1994 | Dintzis et al. . |
| 5,472,883 | 12/1995 | Matsuura et al. ............. 436/518 |
| 5,498,538 | 3/1996 | Kay et al. . |
| 5,506,110 | 4/1996 | Matsuura et al. . |
| 5,552,391 | * 9/1996 | Coutts et al. .................. 514/44 |
| 5,606,047 | 2/1997 | Coutts et al. . |
| 5,633,395 | 5/1997 | Coutts et al. . |
| 6,022,544 | 2/2000 | Dintzis et al. . |

FOREIGN PATENT DOCUMENTS

| | | |
|---|---|---|
| 0 438 259 A1 | 7/1991 | (EP) . |
| 0 442 724 A2 | 8/1991 | (EP) . |
| 0 498 658 A2 | 8/1992 | (EP) . |
| 0 642 798 A2 | 3/1995 | (EP) . |
| 0 730 155 A1 | 9/1996 | (EP) . |
| WO 86/04093 A1 | 7/1986 | (WO) . |
| WO 87/00056 A1 | 1/1987 | (WO) . |
| WO 88/09810 A1 | 12/1988 | (WO) . |
| WO 89/09628 A1 | 10/1989 | (WO) . |
| WO 91/10426 A1 | 7/1991 | (WO) . |
| WO 91/15722 A1 | 10/1991 | (WO) . |
| WO 92/11029 A1 | 7/1992 | (WO) . |
| WO 92/13558 A1 | 8/1992 | (WO) . |
| WO 95/07073 A1 | 3/1995 | (WO) . |
| WO 96/40197 | 12/1996 | (WO) . |
| WO 97/46251 | 12/1997 | (WO) . |

OTHER PUBLICATIONS

Cruse et al., Illustrated Dictionary of Immunology, CRC Press, Boca Raton, FL, 1995, p. 156.*

Ada, G.L. (1987). "The generation of cellular vs. humoral immunity" Chapter 3 in *Synthetic Vaccines*. R. Arnon ed., CRC Press, Inc.: Boca Raton, Florida, vol. 1, pp. 25–37.

Del Papa et al. (1998). "Human β2–glycoprotein I binds to endothelial cells through a cluster of lysine residues that are critical for anionic phospholipid binding and offers epitopes for anti–β2– glycoprotein I antibodies," *Journal of Immunology* 160(11): 5572–5578.

Efimov et al. (1993). "Synthesis of Conjugates of Oligonucleotides with Polyethyleneglycol," Plenum Publishing Corporation, pp. 464–468. Translated from *Bioorganicheskaya Khimiya* 19(8): 800–804.

Francis et al. (1988). "Peptides with added T–cell epitopes can overcome genetic restriction of the immune response"in *Vaccines 88*. H. Ginsberg et al. eds. Cold Spring Harbor Laboratory, pp. 1–7.

Habicht et al. (1973). "Methods for the study of the cellular basis of immunological tolerance" Chapter 6 in *Immune Response at the Cellular Level*. T.P. Zacharia ed., Marcel Dekker, Inc.: New York, pp. 141–160, especially 142.

(List continued on next page.)

*Primary Examiner*—Donna C. Wortman
(74) *Attorney, Agent, or Firm*—Morrison & Foerster, LLP

(57) ABSTRACT aPL analogs that (a) bind specifically to B cells to which an aPL epitope binds and are disclosed. Optimized analogs lack T cell epitope(s) are useful as conjugates for treating aPL antibody-mediated diseases. Methods of preparing and identifying said analogs, methods of treatment using said analogs, methods and compositions for preparing conjugates of said analogs and diagnostic immunoassays for aPL antibodies are disclosed.

25 Claims, 20 Drawing Sheets

OTHER PUBLICATIONS

Hagihara et al. (1995). "Role of the N– and C–terminal domains of bovine β₂–glycoprotein I in its interaction with cardiolipin," *Journal of Biochemistry* 118(1): 129–136.

Hertler, A.A.. (1988). "Human immune response to immunotoxins" in *Immunotoxins*. A.E. Frankel ed., Kluwer Academic Publishers: Boston, pp. 475–480.

Iverson et al. (1998). "Anti–β2 glycoprotein I (β2GPI) autoantibodies recognize an epitope on the first domain of β2GPI," *Proc. Natl. Acad. Sci. U.S.A.* 95: 15542–15546.

Jones et al. (1994) "Conjugates of double–stranded oligonucleotides with poly(ethylene glycol) and keyhole limpet hemocyanin: a model for treating systemic lupus erythematosus," *Bioconjugate Chem.* 5(5):390–399.

Jones et al. (1995). "Immunospecific reduction of antioligonucleotide antibody–forming cells with a tetrakis–oligoncleotide conjugate (LJP 394), a therapeutic candidate for the treatment of lupus nephritis," *Journal of Medicinal Chemistry* 38(12): 2138–2144.

Lenstra et al. (1992). "Isolation of sequences from a random–sequence expression library that mimics viral epitopes," *J. Immunological. Methods* 152: 149–157.

Nossal, G.J. (1989). "Immunologic Tolerance" Chapter 19 in *Fundamental Immunology*. W.E. Paul ed., Raven Pres, Ltd.: New York, pp. 571–586, especially 577–579.

Papalian et al. (1980). "Reaction of systemic lupus erythematogus antinative DNA antibodies with native DNA fragments from 20 to 1,200 base pairs," *J. Clin. Invest.* 65:469–477.

Sehon, A.H. (1991). "Suppression of antibody responses by conjugates of antigens and monomethoxypoly(ethylene glycol)" *Advanced Drug Delivery Reviews* 6(2): 203–217.

McNeil et al., "Immunology and clinical importance of antiphospholipid antibodies" *Adv. Immunol.* (1991) 49:193–280.

Bakimer et al., "Induction of primary antiphospholipid syndrome in mice by immunization with a human monoclonal anticardiolipin antibody (H–3)" *J. Clin. Invest.* (1992) 89:1558– 1563.

Blank et al., "Induction of anti–phospholipid syndrome in naive mice with mouse lupus monoclonal and human polyclonal anti–cardiolipin antibodies" *Proc. Natl. Acad. Sci. USA* (1991) 88:3069–3073.

McNeil et al., Anti–phospholipid antibodies are directed against a complex antigen that includes a lipid–binding inhibitor of coagulation: β₂–glycoprotein I (apoliprotein H) *Proc. Natl. Acad. Sci.* (1990) 87:4120–4124.

Galli et al., "Anticardiolipin antibodies (ACA) directed not to cardiolipin but to a plasma protein cofactor" *Lancet* (1990): pp. 1544–1547.

Wagenknecht et al., "Changes in β₂–glycoprotein I antigenicity induced by phospholipid binding" *Thromb. Haemostas.* (1993) 69:361–365.

Jones et al.,, "Antigenic specificity of anticardiolipin antibodies appears to depend on conformation of β₂–glycoprotein I" (Sep. 9–12, 1992) *Proc. 5th Intl. Symp. Antiphospholipid Antibodies*, Hyatt Regency San Antonio, Texas, (Abstract S5) (4 pages total).

Hunt et al., "The fifth domain of β₂–glycoprotein I contains a phospholipid binding site (cys281–cys288) and a region recognized by anticardiolipin antibodies" *J. Immunol.* (1994) 152:653–659.

Lauer et al., "Amino acid sequence fo the region of β₂–glycoprotein 1 (gp1) which mediates binding of autoantibodies to the cardiolipin–gp1 complex in humans" *Immunol.* (1993) 80:22–28.

Hasselaar et al., "Crossreactivity of antibodies directed against cardiolipin, DNA, endothelial cells and blood platelets" *Thromb. Haemostas.* (1990) 63:169–173.

Vermylen et al., "Is the antiphospholipid syndrome caused by antibodies directed against physiologically relevant phospholipid–protein complexes?" *J. Clin. Lab. Med.* (1992) 120:10–12.

Arvieux et al., "Platelet activating properties of murine monoclonal antibodies to β₂– glycoprotein I" *Thromb. Haemostas.* (1993) 70:336–341.

Scott., J.K., "Identifying lead peptides from epitope libraries" *Biological Approaches to Rational Drug Design* GN (CRC Press, Weiner, D. B. and W.V. Williams, eds., Boca Raton, FL., 1994), Chapter 1, pp. 1–28.

Moos et al., "Recent advances in the generation of molecular diversity" *Ann. Reports Med. Chem.* (1993) 28:315–324.

Scott et al., "Searching for peptide ligands with an epitope library" *Science* (1990) 249:386– 390.

Cesareni, "Peptide display on filamentous phage capsids" *FEBS Lett.* (1992) 307:66–70.

Luzzago et al., "Mimicking of discontinuous epitopes by phage–displayed peptides, I. Epitope mapping of human H ferritin using a phage library of constrained peptides" *Gene* (1993) 128:51–57.

Balass et al., "Identification of a hexapeptide that mimics a conformation–dependent binding site of acetylcholine receptor by use of a phage–epitope library" *Proc. Natl. Acad. Sci. USA* (1993) 90:10638–10642.

Powell, "Peptide stability in drug development: In vitro peptide degradation in plasma and serum" *Ann. Reports Med. Chem.* (1993) 28:285–294.

Reber et al., "Multicenter evaluation of nine commercial kits for the quantitation of anticardiolipin antibodies" (1995) *Thrombosis and Haemostat.* 73:444–452.

Barbas III et al., "Assembly of combinatorial antibody libraries on phage surfaces: The gene III site" (1991) *Proc. Natl. Acad. Sci. USA* 88:7978–7982.

Posnett et al., "A novel method for producing anti–peptide antibodies" (1988) *J. Biol. Chem.* 263:1719–1725.

Steinkasserer et al., "Activity, disulphide mapping and structural modelling of the fifth domain of human β₂–glycoprotein I" *FEBS Lett.* (1992) 313:193–197.

Holmes et al., "A rapid boiling method for the preparation of bacterial plasmids" (1981) *Anal. Biochem.* 144:193–197.

Cwirla et al., "Peptides on phage: A vast library of peptides for identifying ligands" *Proc. Natl. Acad. Sci. USA* (1990) 87:6378–6382.

Dower et al., "High efficiency transformation of *E. coli* by high voltage electroporation" (1988) *Nucleic Acid Res.* 16:6127–6145.

Smith et al., "Libraries of peptides and proteins displayed on filamentous phage" (1993) *Meth. Enzymol.* 217:228–257.

Haas et al., "Rapid sequencing of viral DNA from filamentous bacteriophage" (1993) *BioTechniques* 15:422–423, 426, 428–429.

Sanger et al., "DNA sequencing with chain–terminating inhibitors" (1977) *Proc. Natl. Acad. Sci. USA* 74:5463–5467.

Harris, "Antiphospholipid antibodies" (1990) *Brit. J. Haemotol.* 74:1–9.

Aichele et al., "Peptide–induced T–cell tolerance to prevent autoimmune diabetes in a transgenic mouse model" (1994) *Proc. Natl. Acad. Sci. USA* 91:444–448.

Elliott, "Anergy and suppression in B–cell responses" (1992) *Scand. J. Immunol.* 36:761–767.

McConathy et al., "Isolation and characterization of other apolipoproteins" *Meth. Enzymol.* (1986) 128:296–310.

Nonaka et al., "Molecular cloning of mouse $\beta_2$–glycoprotein I and mapping of the gene to chromosome 11" *Genomics* (1992) 13:1082–1087.

Kato et al., "Amino acid sequence and location of the disulfide bonds in bovine $\beta_2$ glycoprotein I: The presence fo five sushi domains" *Biochem.* (1991) 30:11687–11694.

Steinkasserer et al., "Complete nucleotide and deduced amino acid sequence of human $\beta_2$– glycoprotein I" *Biochem. J.* (1991) 277:387–391.

Petri et al., "Diagnosis of antiphospholipid antibodies" *Rheumatic Disease Clinics of North America*, (1994) 20(2):443–469.

McCarty–Farid "Antiphospholipid antibodies in systemic lupus erythematosus and Sjögren's syndrome" *Current Opinion in Rheumatology* (1993) 5:596–603.

Valesini et al., "A new player in the antiphospholipid syndrome: the $\beta_2$ glycoprotein I cofactor" *Autoimmunity* (1992) 14:105–110.

Wang et al., "Epitope specificity of monoclonal anti–$\beta_2$–glycoprotein I antibodies derived from patients with the antiphospholipid syndrome" *J. Immunol.* (1995) 155:1629–1636.

Gharavi et al., "Induction of antiphospholipid antibodies by immunization with a 15–amino acid peptide spanning the phospholipid binding site of $\beta_2$ glycoprotein I" *J. Invest. Med.* (1996) 44:69A.

Brighton et al., "Antiphospholipid antibodies and thrombosis" *Balliere's Clin. Haematol.* (1994) 7(3):541–557.

Kandiah et al., "Epitope mapping studies of antiphospholipid antibodies and $\beta_2$–GPI using synthetic peptides" *Lupus* (1995) 4(Suppl 1):S7–S11.

* cited by examiner

APL IMMUNOREACTIVE PEPTIDES, CONJUGATES THEREOF AND METHODS OF TREATMENT FOR APL ANTIBODY-MEDIATED PATHOLOGIES

This application is a Continuation-in-Part of U.S. patent application Ser. No. 08/482,651 filed Jun. 7, 1995, now U.S. Pat. No. 5,874,409.

TECHNICAL FIELD

This invention is in the field of immunology and relates to compositions and methods for treating and diagnosing antiphospholipid (aPL) antibody-mediated pathologies. More specifically, the invention relates to conjugates of chemically-defined nonimmunogenic valency platform molecules and immunospecific analogs of aPL-binding epitopes as well as methods and compositions for producing these conjugates. Optimized analogs lack T cell epitopes. In addition, the invention relates to diagnostic assays for detecting the presence of and quantitating the amount of antiphospholipid antibodies in a biological sample. The invention also relates to a method of utilizing random peptide libraries to identify immunospecific analogs of aPL-binding epitopes.

BACKGROUND OF THE INVENTION

Antiphospholipid antibodies occur in autoimmune diseases such as systemic lupus erythematosus (SLE) and antiphospholipid antibody syndrome (APS) as well as in association with infections and drug therapy. APS is characterized by one or more clinical features such as arterial or venous thrombosis, thrombocytopenia and fetal loss. APS may be primary or it may be associated with other conditions, primarily SLE. (PHOSPHOLIPID-BINDING ANTI-BODIES (Harris et al., eds., CRC Press, Boca Raton, Fla., 1991); McNeil et al. ADVANCES IN IMMUNOLOGY, Vol. 49, pp. 193–281 (Austen et al., eds., Academic Press, San Diego, Calif., 1991)). Approximately 30–40% of patients with SLE have aPL, however, 50% of patients with aPL antibodies do not have SLE. This 50% may have other autoimmune rheumatic diseases, miscellaneous conditions or they may have been subjected to drug therapy, particularly chlorpromazine. In one study of 70 patients, 26 males and 44 females, with primary APS (PAPS) but no evidence of SLE, the following features were observed: deep venous thrombosis (DVT) in 31; arterial occlusion in 31, particularly stroke or transient ischemia; myocardial infarctions in 15; recurrent fetal loss in 24; thrombocytopenia (TCP) in 32; 10 had a positive Coombs' test; Evans' syndrome in 7; antinuclear antibody (ANA) in 32, but less than 1:160 in 29; and antimitochondrial antibody (AMA) in approximately 24. (McNeil et al., supra.). Estimates vary but in about 5% of all stroke patients, aPL antibodies are thought to be an important contributing factor.

Transient aPL antibodies, such as those detected in a VDRL test, occur during many infections. Approximately 30% of patients possessing persistent aPL antibodies have suffered a thrombic event. The presence of aPL antibodies defines a group of patients within SLE who display a syndrome of clinical features consisting of one or more of thrombosis, TCP, and fetal loss. The risk of this syndrome in SLE overall is around 25%; this risk increases to 40% in the presence of aPL antibodies and decreases to 15% in their absence. Because aPL antibodies were thought to be directed at phospholipids in plasma membranes, it has been postulated that they may exert direct pathogenic effects in vivo by interfering with hemostatic processes that take place on the phospholipid membranes of cells such as platelets or endothelium. In patients with PAPS, the fact that aPL antibodies appear to be the only risk factor present is further evidence that these antibodies have a direct pathogenic role. Induction of PAPS by immunizing mice with human anticardiolipin antibodies is the best evidence yet that aPL antibodies are directly pathogenic (Bakimer et al. 1992 *J. Clin. Invest.* 89:1558–1563; Blank et al. 1991 *Proc. Natl. Acad. Sci.* 88:3069–3073).

Measurement of aPL antibodies in the clinical environment is still an imperfect art. A commercially available set of standard antisera (APL Diagnostics, Inc., Louisville, Ky.) allow generation of a standard curve for comparison of assays performed in various laboratories. A great deal of inconsistency exists, however, between the results obtained at these laboratories regarding the exact GPL and MPL, the unit of measurement for IgG and IgM antiphospholipid antibodies, respectively, ratings for given sera and the levels of GPL and MPL that are categorized as high, medium or low titer. The available commercial kits vary greatly in the values assigned to the commercially available standards (Reber et al. (1995) *Thrombosis and Haemostat.* 73:444–452). In spite of these limitations, there is general agreement that the epitopes recognized by antibodies in APS, PAPS and other aPL antibody-mediated diseases including recurrent stroke and recurrent fetal loss are located in the 5th domain of $\beta_2$-GPI and are exposed to the antibody following binding of $\beta_2$-GPI to cardiolipin.

It is now generally accepted that aPL antibodies recognize an antigenic complex comprised of $\beta_2$-glycoprotein I ($\beta_2$-GPI) and negatively-charged phospholipid, e.g., cardiolipin (McNeil et al. (1990) *Proc. Natl. Acad. Sci.* 87:4120–4124; Galli et al. (1990) *Lancet* I:1544–1547) (hereinafter "aPL immunogen"). $\beta_2$-GPI is a minor plasma glycoprotein found free and in association with lipoprotein lipids where it is also known as apolipoprotein H (apo H). It consists of five independently folding domains referred to as Sushi or short consensus repeat domains that resemble similar domains in other proteins. $\beta_2$-GPI has been reported to undergo antigenic and conformational changes upon binding phospholipid (Wagenkneckt et al. (1993) *Thromb. Haemostas.* 69:361–365; Jones et al. (1992) *Proc. 5th Intl. Symp. Antiphospholipid Antibodies* (Abstract S5)). The fifth domain contains the putative sites of lipid binding and aPL antibody binding (Hunt J. and S. Krilis, (1994) *J. Immunol.* 152:653–659; Lauer et al. (1993) *Immunol.* 80:22–28). The pathological mechanism for aPL is unknown (McNeil et al., supra). Most explanations invoke endothelial cell function or platelet involvement (Haselaar et al. (1990) *Thromb. Haemostas.* 63:169–173). These explanations suggest that following blood vessel endothelial cell injury or platelet activation, the exposure or transbilayer migration of anionic phospholipid to the plasma-exposed surface may lead to $\beta_2$-GPI-binding and trigger aPL antibody formation.

aPL antibodies may be directly prothrombotic by reducing prostacyclin formation (Vermylen, J. and J. Amout (1992) *J. Clin. Lab. Med.* 120:10–12); by direct interference with the action of coagulation proteins; or by blocking the ability of $\beta_2$-GPI to inhibit the intrinsic blood coagulation pathway, platelet prothrombinase activity, and ADP-mediated platelet aggregation (Arvieux et al. (1993) *Thromb. Haemostas.* 60:336–341).

A major new tool in medicinal chemistry in the search for lead compounds has been the advent of combinatorial libraries providing vast molecular diversity. Molecular diversity may arise from chemical synthesis or from biological systems (Scott., J. K. RATIONAL DRUG DESIGN (CRC Press, Weiner, D. B. and W. V. Williams, eds., Boca, Raton, Fla., 1994); Moos et al. (1993) *Ann. Reports Med. Chem.* 28:315–324). By displaying random peptides on the surface of filamentous phage, epitope libraries containing hundreds of millions of clones for probing by clinically significant antibodies have been created (Scott, J. K. and G. P. Smith (1990) *Science* 249:286–390; Cesareni, G. (1992) *FEBS Lett.* 307:66–70). Such phage libraries are prepared by incorporating randomized oligonucleotide sequences into the phage genome, usually the pIII gene, which encode unique peptide sequences on the surface of each phage. Following sequential rounds of affinity purification and amplification, those phage that bind antibody are propagated in *E. coli* and the binding peptides identified by sequencing the corresponding coding region of viral DNA. In most cases, subsequent study will involve corresponding synthetic peptides after establishing their ability to bind antibody. Phage-based libraries have been used to mimic discontinuous epitopes (Luzzago et al. (1993) *Gene* 128:51–57; BaLass et al. (1993) *Proc. Natl. Acad. Sci.* 90:10638–10642). The potential plasma instability of peptide-based drugs has been successfullly overcome by N-terminal blocking or by the judicious use of amino acid analogs (Powell, M. F. (1993) *Ann. Reports Med. Chem.* 28:285–293).

At present there is no selective, immunospecific therapy for patients showing high titers of aPL antibodies. In many cases use of drugs such as aspirin, steroids, and warfarin has proven to be largely inadequate (PHOSPHOLIPID-BINDING ANTIBODIES (Harris et al., eds., CRC Press, Boca Raton, Fla., 1991); McNeil et al., supra). Synthetic mimetic peptides, characterized by (i) the inability to activate T cells while (ii) retaining the ability to bind immune B cells, are used to tolerize B cells in an antigen-specific manner. This technology is disclosed in co-owned, co-pending U.S. patent application, Ser. No. 08/118,055, filed Sep. 8, 1993, and U.S. Pat. No. 5,268,454, which are incorporated by reference herein in their entirety. As disclosed in the application and patent cited above, B cell tolerance entails administering such peptides conjugated to multivalent, stable, non-immunogenic valency platforms in order to abrogate antibody production via B cell anergy or clonal deletion after cross-linking surface immunoglobulin.

Although the exact molecular nature of the target epitopes recognized by aPL antibodies is unknown, the use of peptides derived from epitope libraries will allow for the construction of successful tolerogens. B cell tolerogens for the treatment of human systemic lupus erythematosus-related nephritis have also been disclosed in co-owned U.S. Pat. Nos. 5,276,013 and 5,162,515 which are incorporated by reference herein in their entirety.

DISCLOSURE OF THE INVENTION

This invention resides in the discovery of a method for identifying analogs of key epitopes recognized by aPL antibodies in patients suffering from PAPS, APS and other aPL antibody-mediated diseases, such as recurrent stroke and recurrent fetal loss, using random peptide phage libraries.

Accordingly, one aspect of the invention is an improved method for screening random peptide phage libraries in order to identify the peptide sequences which best mimic the epitopes recognized by aPL antibodies. This method comprises the steps of: (a) biopanning the library using methods modified from those known in the art; (b) eliminating very weakly-binding phage by micropanning the phage screened from step (a) by (i) incubating the phage in microplate wells coated with aPL antibody bound to Protein G, (ii) washing the microplate wells to remove unbound phage, (iii) eluting the bound phage, and (iv) infecting a microorganism such as *E. coli* with the eluted phage and counting the number of infected microorganisms by plating on agar; (c) determining the strongest-binding clones recovered in (b) by evaluation via phage-capture ELISA by (i) coating the wells of a microplate with aPL antibody, (ii) incubating the strongest-binding clones identified by micropanning in (b) in the coated wells and washing away unbound phage, (iii) quantitating the number of phage bound to the antibody using an enzyme-conjugated goat anti-phage antibody in a colorimetric ELISA assay and, if several equivalent strongly-binding clones are identified, an additional round of (d) phage-ELISA on the strongest-binding phage-capture-ELISA clone.

In this regard, the invention encompasses a method for identifying analogs of epitopes which specifically bind aPL antibodies isolated from humans suffering from an aPL antibody-mediated disease comprising: (a) preparing phage random peptide libraries; (b) screening said libraries with aPL antibodies to identify aPL mimetic epitopes, wherein said screening comprises (i) screening said libraries by biopanning; (ii) further screening phage isolated by biopanning in (i) by micropanning; and (iii) identifying phage containing aPL antibody high-affinity binding peptides recovered in (ii) by immunoassay.

The invention also encompasses a method of biopanning phage random peptide libraries to identify and isolate peptides which bind to aPL antibody comprising: (a) reacting affinity-purified aPL antibody with phage bearing random peptide inserts; (b) recovering phage bearing random peptide inserts which bind to the aPL antibody; (c) infecting a microorganism with phage recovered in (b); and (d) culturing the infected microorganism in an antibiotic-containing medium in order to isolate the phage.

The invention further encompasses a method of micropanning phage random peptide libraries to identify and isolate peptides having a high binding affinity to aPL antibodies comprising: (a) isolating phage bearing random peptide inserts by biopanning; (b) incubating the phage recovered in step (a) in microplate wells coated with aPL antibody bound to Protein G; (c) washing the microplate wells to remove unbound phage; (d) eluting bound phage; and (e) infecting a microorganism with phage recovered in (d); and (f) culturing the infected microorganism in an antibiotic-containing medium in order to isolate the phage.

The invention also encompasses the above method described wherein the immunoassay is a phage-capture ELISA comprising: (a) incubating phage bearing random peptide inserts isolated by micropanning in the microplate wells coated with aPL antibody; (b) washing away unbound phage;(c) incubating an enzyme-labeled anti-phage antibody to the wells; (d) washing away unbound enzyme-labeled anti-phage antibody; (e) adding a colorimetric substrate; and (f) measuring the absorbance of the substrate to identify high affinity-binding phage.

Also encompassed by the invention is the method described above and further comprising performing an additional phage-capture ELISA assay of the high affinity-binding phage comprising: (a) coating a uniform amount of the phage on microplate wells; (b) incubating aPL antibody in the wells; (c) washing away unbound antibody; (e) incubating an enzyme-labelled anti-aPL antibody with the bound aPL antibody; (f) washing away unbound enzyme-labelled anti-aPL antibody; (g) adding a colorimetric substrate to the wells; and (h) measuring the absorbance of the substrate to measure the relative binding affinity of the phage.

The invention also encompasses the method described above wherein the immunoassay is a colony-blot immunoassay comprising: (a) culturing a microorganism infected with phage bearing random peptide inserts on a nitrocellulose membrane atop an agar-containing culture medium; (b) replicate transferring the microorganism cultured in (a) by blotting the microorganism on a second nitrocellulose membrane atop an agar-containing culture medium; (c) incubating the transferred microorganism; (d) lysing the microorganism; (e) digesting the microorganism with lysozyme; (f) blocking the membrane with a gelatin solution; (g) incubating the membrane with aPL antibody; (h) washing away unbound aPL antibody; (i) incubating a enzyme-labelled anti-aPL antibody with the nitrocellulose membrane; (j) washing away unbound enzyme-labelled anti-aPL antibody; (k) adding a colorimetric substrate; and (l) measuring the absorbance of the substrate to identify high affinity-binding phage.

A method for assaying and ranking, for affinity-binding characteristics, epitopes which specifically bind aPL antibodies isolated from humans suffering from an aPL antibody-mediated disease is also encompassed, the method comprising: (a) coating wells of a microtitration plate with cardiolipin; (b) adding adult bovine or human serum as a source of $\beta_2$-GPI to bind to the cardiolipin and to prevent non-specific binding to the wells of the plate; (c) incubating a solution of monomeric analog and a high-titered aPL antibody for a pre-determined time; (d) adding the aPL antibody/analog mixture to wells of the microtitration plate and incubating for a pre-determined time; (e) washing the wells to wash away unbound aPL antibody; (f) adding anti-human IgG conjugated with a label (e.g., an enzyme) to the wells of the plate and incubating for a pre-determined time; (g) washing the wells to wash away unbound anti-human IgG conjugate; (h) adding a substrate for the labeled conjugate and developing the substrate/label reaction for a pre-determined time; (i) measuring the end-product of the substrate/label reaction to quantitate the amount of aPL antibody bound to the well; (j) calculating the percentage inhibition, if any, of binding of the aPL antibody to determine the affinity of the analog to the aPL antibody.

The invention also encompasses a diagnostic immunoassay for determining the presence of aPL antibody in body fluids taken from subjects suspected of suffering from an aPL antibody-mediated disease comprising contacting a sample of a body fluid with an analog of an epitope which specifically binds aPL antibodies and determining by methods well known in the art whether aPL antibodies are present in the body fluid and, if present, quantitating the amount of aPL antibodies present in the fluid. One such immunoassay comprises: (a) coating wells of a microtitration plate with an analog of an epitope which specifically binds aPL antibodies; (b) washing the wells to wash away unbound analog; (c) adding a test sample of a body fluid to the wells wash away unbound analog; (c) adding a test sample of a body fluid to the wells and incubating for a pre-determined time; (d) washing the wells to remove unbound test sample; (e) adding anti-human IgG conjugated with a label to the wells of the plate and incubating for a pre-determined time; (f) washing the wells to wash away unbound anti-human IgG conjugate; (g) adding a substrate for the labeled conjugate and developing the substrate/label reaction for a pre-determined time; (h) measuring the end-product of the substrate/label reaction to determine the presence of anti-aPL antibody in the test sample. A diagnostic immunoassay as described above wherein the immunoassay is quantitative is also encompassed.

The phage-ELISA assay consists of (i) coating a uniform amount of different clones on wells of a microtitration plate followed by (ii) identifying the peptide inserts which most strongly bind aPL antibody by adding antibody to the wells and developing the reaction with an enzyme-labeled anti-human IgG conjugate. The random peptides displayed by the phage which have a high binding affinity to aPL antibody as measured by phage-ELISA, colony blot or phage-capture-ELISA represent the analogs of the aPL-specific epitope. These peptides are then synthesized and ranked for strength of binding using competition assays.

Another aspect of the invention is aPL antibody-binding analogs that bind specifically to B cells to which an aPL epitope binds. Optimized analogs lack T cell epitope(s).

Yet another aspect of the invention is a composition for inducing specific B cell tolerance to an aPL immunogen comprising a conjugate of a nonimmunogenic valency platform molecule and an aPL antibody-binding analog that (a) binds specifically to B cells to which an aPL immunogen binds and (b) lacks T cell epitope(s).

MODES FOR CARRYING OUT THE INVENTION

A. Definitions

Figure 1:
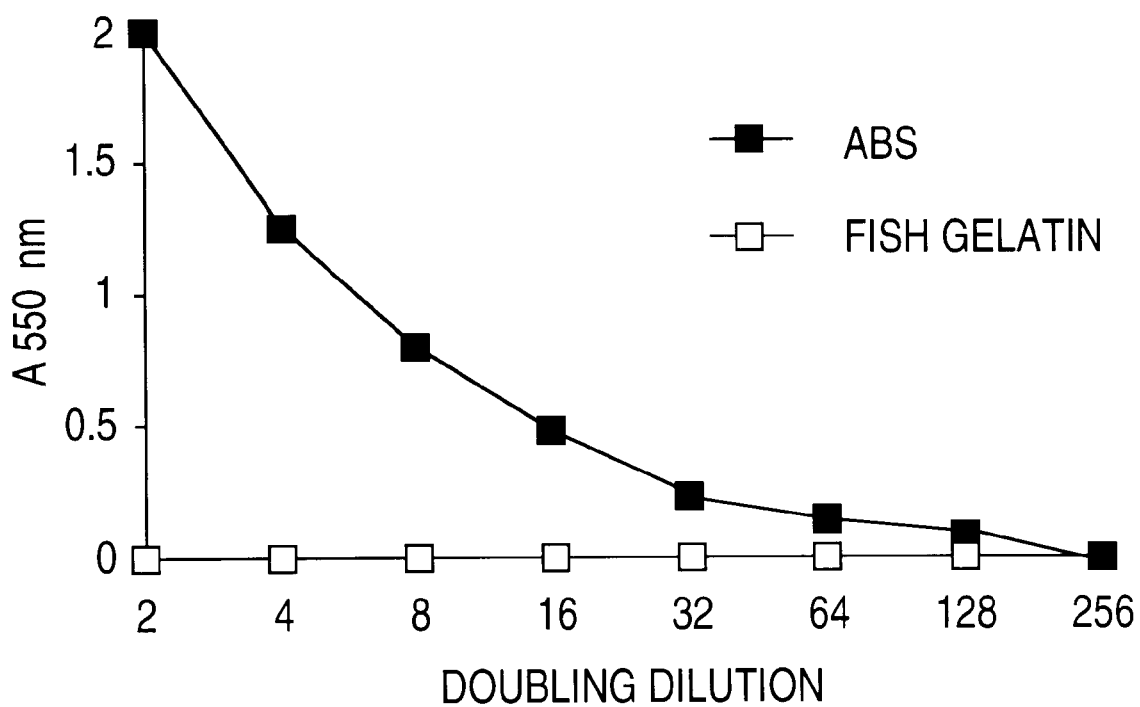
FIG. 1 shows that the substitution of fish gelatin for adult bovine serum abolished all anticardiolipin (ACA) activity in an ELISA assay of a commercial aPL antibody standard. This result supported the findings of McNeil et al., supra, and Galli et al., supra, concerning the importance of $\beta_2$-glycoprotein I ($\beta_2$-GPI) in defining the target epitope(s) of ACA.

As used herein the term "aPL antibody" means any antibody which specifically binds β2-GPI that mediates disease.

As used herein the term "B cell anergy" intends unresponsiveness of those B cells requiring T cell help to produce and secrete antibody and includes, without limitation, clonal deletion of immature and/or mature B cells and/or the inability of B cells to produce antibody.

"Unresponsiveness" means a therapeutically effective reduction in the humoral response to an immunogen. Quantitatively the reduction (as measured by reduction in antibody production) is at least 50%, preferably at least 75%, and most preferably 100%.

"Antibody" means those antibodies which are T cell dependent.

As used herein the term "immunogen" means an entity that elicits a humoral immune response comprising aPL antibodies. Immunogens have both B cell epitopes and T cell epitopes. aPL immunogens that are involved in aPL antibody-mediated pathologies may be external (foreign to the individual) immunogens such as drugs, including native biological substances foreign to the individual such as therapeutic proteins, peptides and antibodies, and the like or self-immunogens (autoimmunogens) such as those associated with antibody-mediated hypercoagulability (stroke).

The term "analog" of an immunogen intends a molecule that (a) binds specifically to an antibody to which the immunogen binds specifically and (b) lacks T cell epitopes. Although the analog will normally be a fragment or derivative of the immunogen and thus be of the same chemical class as the immunogen (e.g., the immunogen is a polypeptide and the analog is a polypeptide), chemical similarity is not essential. Accordingly, the analog may be of a different chemical class than the immunogen (e.g., the immunogen is a carbohydrate and the analog is a polypeptide) as long as it has the functional characteristics (a) and (b) above. The analog may be a peptide, carbohydrate, lipid, lipopolysaccharide, nucleic acid or other biochemical entity. Further, the chemical structure of neither the immunogen nor the analog need be defined for the purposes of this invention.

The term "analog" of an immunogen also encompasses the term "mimotope." The term "mimotope" intends a molecule which competitively inhibits the antibody from binding the immunogen. Because it, specifically binds the antibody, the mimotope is considered to mimic the antigenic determinants of the immunogen.

As used herein "valency platform molecule" means a nonimmunogenic molecule containing sites which facilitate the attachment of a discrete number of analogs of immunogens.

"Nonimmunogenic" is used to describe the valency platform molecule and means that the valency platform molecule elicits substantially no immune response when it is administered by itself to an individual.

As used herein "individual" denotes a member of the mammalian species and includes humans, primates, mice and domestic animals such as cattle and sheep, sports animals such as horses, and pets such as dogs and cats.

As used herein "pharmacophore" means the three dimensional orientation and chemical properties of key groups involved in binding of an aPL analog to the antibody target.

B. Identification of aPL Antibody-binding Analogs aPL antibody-binding analogs may be identified by screening candidate molecules to determine whether or not they (a) bind specifically to aPL antibodies and (b) lack T cell epitopes. Specific binding to aPL antibodies may be determined using conventional immunoassays such as the ELISA assays described in the examples below and the presence or absence of T cell epitopes may be determined by conventional T cell activation assays also described in the examples. In this regard, an analog which "binds specifically" to serum antibodies to the immunogen exhibits a reasonable affinity thereto, e.g., $10^7$ $M^{-1}$. The presence or absence of T cell epitopes may be determined using a tritiated thymidine incorporation assay disclosed in Ser. No. 08/118,055. The presence of T cell epitopes can also be determined by measuring secretion of T cell-derived lymphokines by methods well known in the art. Analogs that fail to induce statistically significant incorporation of thymidine above background are deemed to lack T cell epitopes. It will be appreciated that the quantitative amount of thymidine incorporation may vary with the immunogen. Typically a stimulation index below about 2–3, more usually about 1–2, is indicative of a lack of T cell epitopes.

C. Preparation of Conjugates

The aPL antibody-binding analogs are coupled to a nonimmunogenic valency platform molecule to prepare the conjugates of the invention. Preferred valency platform molecules are biologically stabilized, i.e., they exhibit an in vivo excretion half-life often of hours to days to months to confer therapeutic efficacy, and are preferably composed of a synthetic single chain of defined composition. They will normally have a molecular weight in the range of about 200 to about 200,000, usually about 200 to about 20,000. Examples of valency platform molecules within the present invention are polymers such as polyethylene glycol (PEG), poly-D-lysine, polyvinyl alcohol and polyvinylpyrrollidone. Preferred polymers are based on polyethylene glycols (PEGs) having a molecular weight of about 200 to about 8,000.

Other valency platform molecules suitable for use within the present invention are the chemically-defined, non-polymeric valency platform molecules disclosed in co-owned, co-pending U.S. patent application Ser. No. 08/152,506, filed Nov. 15, 1993 now U.S. Pat. No. 5,552, 391, which is incorporated by reference herein in its entirety. Particularly preferred homogeneous chemically-defined valency platform molecules suitable for use within the present invention are derivatized 2,2'-ethylenedioxydiethylamine (EDDA) and triethylene glycol (TEG).

Additional suitable valency platform molecules include tetraaminobenzene, heptaaminobetacyclodextrin, tetraaminopentaerythritol, 1,4,8,11-tetraazacyclotetradecane and 1,4,7,10-tetraazacyclododecane (CYCLEN®).

Conjugation of the aPL antibody-binding analog to the valency platform molecule may be effected in any number of ways, typically involving one or more crosslinking agents and functional groups on the analog and valency platform molecule.

Polypeptide analogs will contain amino acid sidechain moieties containing functional groups such as amino, carboxyl, or sulfhydryl groups that will serve as sites for coupling the analog to the carrier. Residues that have such functional groups may be added to the analog if the analog does not already contain these groups. Such residues may be incorporated by solid phase synthesis techniques or recombinant techniques, both of which are well known in the peptide synthesis arts. In the case of carbohydrate or lipid analogs, functional amino and sulfhydryl groups may be incorporated therein by conventional chemistry. For instance, primary amino groups may be incorporated by reaction with ethylenediamine in the presence of sodium cyanoborohydride and sulfhydryls may be introduced by reaction of cysteamine dihydrochloride followed by reduction with a standard disulfide reducing agent. In a similar fashion, the valency platform molecule may also be derivatized to contain functional groups if it does not already possess appropriate functional groups.

Hydrophilic linkers of variable lengths are useful for connecting peptides or other bioactive molecules to valency platform molecules. Suitable linkers include linear oligomers or polymers of ethyleneglycol. Such linkers include linkers with the formula $R^1S(CH_2CH_2O)_nCH_2CH_2O(CH_2)_mCO_2R^2$ wherein n=0–200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloacyl, maleiamide, etc., via a thioether to a second molecule which contains an amino group via an amide bond. These linkers are flexible with regard to the order of attachment, i.e., the thioether can be formed first or last.

The conjugates will normally be formulated for administration by injection (e.g., intraperitoneally, intravenously, subcutaneously, intramuscularly, etc.). Accordingly, they will typically be combined with pharmaceutically acceptable vehicles such as saline, Ringer's solution, dextrose solution, and the like. The conjugate will normally constitute about 0.01% to 10% by weight of the formulation. The conjugate is administered to an individual in a "therapeutically effective amount", i.e., an amount sufficient to produce B cell anergy to the involved immunogen and effect prophylaxis, improvement or elimination of the antibody-mediated condition being addressed. The particular dosage regimen, i.e., dose, timing and repetition, will depend on the particular individual and that individual's medical history. Normally, a dose of about 1 μg to about 100 mg conjugate/kg body weight, preferably about 100 μg to about 10 mg/kg body weight, will be given weekly. Other appropriate dosing schedules would be as frequent as daily or 3 doses per week, or one dose per week, or one dose every two to four weeks, or one dose on a monthly or less frequent schedule depending on the individual or the disease state. Repetitive administrations, normally timed according to B cell turnover rates, may be required to achieve and/or maintain a state of humoral anergy. Such repetitive administrations will typically involve treatments of about 1 μg to about 10 mg/kg body weight or higher every 30 to 60 days, or sooner, if an increase in antibody titer is detected. Alternatively, sustained continuous release formulations of the conjugates may be indicated for some pathologies. Various formulations and devices for achieving sustained release are known in the art.

Anti-helper T cell treatments may be administered together with the conjugates. Such treatments usually employ agents that suppress T cells such as steroids or cyclosporin.

D. Nature of the Antigen for aPL Antibodies

Initial studies on aPL antibodies by the inventors coincided with the publication of reports questioning the nature of the antigenic site recognized by these antibodies. Initially these antibodies were thought to recognize the cardiolipin molecule much like those antibodies detected in a VDRL test. As shown in FIG. 1, substitution of fish gelatin for adult bovine serum in the anticardiolipin antibody (ACA) solid phase ELISA essentially abolished all ACA activity of an antibody preparation obtained commercially as an ACA standard. This finding indicated the ACA antibodies recognized a determinant on a serum protein as proposed by McNeil et al., supra and Galli et al., supra, rather than cardiolipin itself. This protein was shown by these authors to be $\beta_2$-GPI and, thus, the terms "ACA" or "anti-cardiolipin antibodies" are really misnomers but are still used today to refer to these antibodies.

The majority of autoimmune, IgG aPL antibodies recognize determinants on the $\beta_2$-GPI molecule. These epitopes may be formed or exposed on $\beta_2$-GPI only upon its binding to cardiolipin (a neo epitope). Alternatively, the epitope on $\beta_2$-GPI may exist in a single copy per $\beta_2$-GPI molecule and may have low affinity for aPL antibodies. Sufficient avidity to maintain an antibody-antigen interaction might be reached only with the alignment of two of these sites on adjacent $\beta_2$-GPI molecules by their binding to cardiolipin.

Additional insight into the β2-GPI epitope structure has been gained by nuclear magnetic resonance (NMR) analysis of aPL analogs within the present invention which mimic the native epitope(s) of β2-GPI. For, example, a comparison of the NMR solution structure of two peptide aPL analogs that are highly cross-reactive with aPL antibodies showed that both peptides have turns at approximately the same positions in the peptide sequence (see FIGS. 18 and 19).

E. ACA ELISA

The necessity of large-scale testing in connection with GPL scoring of clinical samples and chromatographic purifications of research antibodies and $\beta_2$-GPI led to the development of an ELISA assay for aPL antibodies with performance in close agreement with a commercial kit and similar to the design found to have the best reproducibility (Reber et al., supra).

F. Immunoaffinity Purification of aPL Antibodies

In order to isolate the aPL antibodies, multilamellar, cardiolipin-containing dispersions (liposomes; also containing cholesterol and dicetylphosphate) are incubated with aPL plasma (or serum). These liposomes are pelleted from the serum by centrifugation. After washing, the liposome mixture is disrupted by 2% octylglucoside detergent and applied to a protein A-agarose column. Following extensive washings to first remove lipids and then to remove non-IgG components, IgG aPL antibody is eluted from protein A with mild acid, neutralized, buffer-exchanged, and tested in the ACA ELISA. This procedure yields aPL antibody enriched up to 10,000-fold that is devoid of any contaminating $\beta_2$-GPI as shown by western blotting with rabbit IgG anti-human $\beta_2$-GPI antisera.

G. Construction of Filamentous Phage Random Peptide Libraries

Eleven different fUSE 5 filamentous phage random peptide libraries on the p-III protein (five copies of p-III with peptide per phage) are constructed. These libraries provide a vast array of shapes and structures for the discovery of mimetic epitopes. Four libraries, designated "x" libraries, have peptide inserts that are 8, 10, 12, and 15 residues in length, respectively, and are flanked by proline residues on both the amino and carboxyl ends. The purpose of these proline residues is to disrupt any contribution to secondary structure that might arise from the native p-III protein and to project the insert into the solvent. The "y'" libraries contain cysteine-bounded inserts that are 6, 7, 8, 9, 11, and 13 amino acids long. The "y" library is the same as the "y'" library except that it lacks the 6 and 8 amino acid inserts. These peptide inserts for both "y" and "y'" libraries are flanked by cysteine residues at both the amino and carboxyl ends to form cyclic, more rigid structures. Proline residues are incorporated outside these cysteine residues for reasons similar to those for the "x" libraries above. The "x," "y'", and "y" libraries are located five residues from the amino terminus of the native p-III protein. The "z" library consists of random eight amino acid inserts located at the amino terminus of the p-III protein and do not contain any flanking proline or cysteine residues. A combination of the "x,""y'" and "z" libraries represents eleven different libraries each with approximately one hundred million different peptide inserts.

These libraries are constructed by incorporation of random oligonucleotide sequences of the length appropriate to give the desired length insert into the p-III gene of fUSE 5 using standard molecular biology techniques. Following restriction endonuclease digestion of the fUSE 5 DNA, an excess of kinased oligonucleotides provided as gapped duplexes is added and ligated. The DNA is then electroporated into *E. coli* and inserts are selected by culturing in tetracycline-containing media. The phage from this culture (which contain the peptide insert) are isolated from the supernatant, washed and resuspended in buffer. Typically libraries are shown to have $7 \times 10^8$ independent clones at $8 \times 10^{12}$ transducing units per mL.

H. Phage-screening Methodology

The essence of screening phage display peptide libraries lies in the ability to collapse billions of potential candidate phage to a relative few with outstanding properties. The original screening protocols recommended by Scott, J. K. and G. P. Smith, (1990) *Science* 249:315–324 are significantly modified to facilitate the selection of the best epitopes for various aPL antibodies. These procedures are designed to apply greater stringency of selection as the screen progressed until a point is reached where a useful number of clones representing the best sequences can be thoroughly investigated. With some antibodies, the library does not appear to have sequences which bind very tightly and if a method with a high degree of stringency is applied to the screen, no clones survive that are specific. On the other hand, the library frequently yields many clones that represent good analogs of the antigen and it is necessary to employ a method with a high degree of stringency to identify the best epitopes. For that reason, assays were developed with varying degrees of stringency in order to identify the best epitopes from an epitope library screen. The assays are listed here in order of increasing stringency: Biopanning<Micropanning<Phage-Capture ELISA<Phage ELISA=Colony Blot=Peptide ELISA.

(i) Biopanning

"Biopanning" describes the technique wherein affinity-purified aPL antibody and phage bearing random peptide inserts are allowed to mix, following which antibody-specific recovery captures the bound phage. The phage confer tetracycline resistance to *E. coli* that are propagated in a tetracycline-containing medium and then isolated. Multiple rounds of biopanning enrich the number of immuno-specific phage in a sample. Phage are always recovered at the end of three to five rounds of selection but may represent only sequences that are nonspecifically bound at low affinities for the selecting antibodies. A method for further evaluating these phage (micropanning) is required.

(ii) Micropanning

An estimation of the relative strength of binding of the phage to the aPL antibody can be determined by "micropanning." Micropanning is carried out following three or more rounds of biopanning and uses the same antibody as employed in the biopanning method. The method consists of dilution of the phage from the last round of biopanning and analyzing fifty or more of these clones by micropanning. Micropanning is accomplished by growing each clone to a similar density and then incubating dilute phage at an optimal single concentration in microtitration wells previously coated with a constant amount of antibody. The optimal single concentration of phage is that concentration most likely to reveal the widest range of micropanning scores (from 0 to 4+) and, thus, permit the greatest discrimination among the clones being tested. It is based on the micropanning behavior of six randomly selected clones where the score is determined at each of several concentrations of phage obtained by serial dilution. Following the incubation with antibody, the unbound phage are washed away and the amount of bound phage is used as an indication of the affinity of the phage insert for the antibody. The amount of bound phage is determined by elution with mild acid followed by neutralization and infection of *E. coli*. The number of infected *E. coli* are then quantitated by plating the microorganisms on agar plates containing tetracycline and then determining colony densities achieved by each clone.

(iii) Phage-Capture ELISA

The phage-capture ELISA test was developed to provide an intermediate level assay to bridge the gap between the relatively low stringency of the micropanning assay and the high stringency of the phage- or peptide-ELISA assays. Preliminary studies show that some antibody preparations give too many positive clones by micropanning but none by phage-ELISA or peptide-ELISA. The limitation of the phage-ELISA described below is that only five copies of p-III are located on each phage and even with a large number of phage coated on a well, few copies of the insert are represented and detection requires that the antibody have a very high affinity for the insert. With the phage-capture ELISA, the signal is amplified many times which facilitates the detection of lower affinity, stable interactions between the antibody and the insert.

The phage-capture ELISA consists of the following steps. Microtitration wells are coated with aPL antibody and phage clones are added as in the micropanning assay. Unbound phage are washed away and the amount of bound phage is quantitated using an enzyme-conjugated goat antiserum which binds the major coat protein of the phage. Phage screened using phage-capture ELISA react with many aPL antibodies and provide a strong signal in subsequent ELISA assays. This intermediate level of sensitivity allows for greater efficiency in the peptide synthesis effort since few micropanning-positive phage are phage-capture ELISA positive. As a result, peptides synthesized from positive phage-capture ELISA phage are generally immunoreactive.

(iv) Phage-ELISA

This method of selecting phage requires very tight binding of the insert to the screening antibody. Phage are directly coated onto wells of a microtitration plate and incubated with the screening antibody. Following washes to remove unbound antibody, an anti-human IgG alkaline phosphatase conjugate is added to bind any aPL antibodies bound to the phage. APL antibodies are then detected by adding a colorimetric substrate to the well which will react with alkaline phosphatase according to methods well known in the art.

(v) Colony Blot

This assay allows large-scale colony screening of *E. coli* infected by biopanned phage. This procedure is an alternative to phage-ELISA for identifying immunoreactive clones and exhibits a comparable level of sensitivity without requiring culturing of individual phage clones prior to testing. In this assay, *E. coli* infected with phage from a round of biopanning are spread on a large diameter nitrocellulose (NC) membrane and cultured overnight on the surface of an agar plate containing tetracycline (Barbas et al. (1991) *Proc. Natl. Acad. Sci. USA* 88:7978–7982). Each colony results from infection by phage containing identical sequences. Several replicate transfer blots on NC are made using this NC "master" and are allowed to grow on the surface of an agar plate. Following the chemical and enzymatic disruption of phage-infected colonies on the blots, the phage may be probed by the techniques commonly used in Western blotting, i.e., staining or immunoblotting. Blots that have been blocked may be incubated with the screening aPL antibody. Following washes to remove unbound antibody, an anti-human IgG horseradish peroxidase conjugate is added to bind to any aPL-antibody that is bound to phage. The addition of a colorimetric substrate allows one to localize the discrete colonies in the master plate which represent immunospecific phage that may be cloned for further study.

(vi) Peptide-ELISA

Following DNA sequencing to determine the peptide insert sequences of the best-reacting phage in the assays described above, the corresponding peptides are made using standard Fmoc peptide chemistry as is well known in the art. For the peptide-ELISA assay, the peptides can be made, for example, as branched tetravalent molecules, i.e., each molecule has four copies of the insert. Such a molecule can coat the well of a microtitration plate and still have epitopes exposed to the solution to allow binding by an antibody. The tetravalent peptides are synthesized by incorporating lysines as branch points at the first two couplings analogous to the methods used for Multiple Antigenic Peptides (MAPS) (Posnett et al. (1988) *J. Biol. Chem.* 263:1719–1725). A spacer consisting of glycine-serine-glycine-serine (SEQ ID NO:8) is added on each arm after the lysines and then the insert, including the framework amino acids found in the phage, proline-glycine at the carboxyl terminus and alanine-glycine-proline at the amino terminus. All amino acids in this synthesis are added one at a time using standard Fmoc methods.

These peptides are then assayed by ELISA which is carried out by coating the peptides on microtitration wells and then assaying their reactivity with aPL antibody in a standard ELISA format. In practice, the peptides usually bind very strongly to the original screening antibody and show some cross-reactivity with other aPL antibodies. Controls of non-aPL antibodies are included to eliminate non-specific binding peptides.

(vii) Competitive Binding Peptide-ELISA

Once ELISA-positive peptides are identified, it is necessary to quantitate their relative binding affinity to the aPL antibodies and to determine whether or not two peptides bind the same population of antibodies in a given patient serum via a peptide-competition ELISA assay. In this assay, various monomeric peptides compete with tetravalent peptides coated on a microtitration plate well. To perform the assay, the peptides to be evaluated are synthesized as monomers, i.e., without the lysine branches employed in the synthesis of the tetravalent peptides, using standard Fmoc chemistry. The monomeric peptides are then purified and dissolved at known concentrations. Wells of a microtitration plate are coated with a tetravalent peptide known to bind to the aPL antibody. Serial dilutions of the monomeric peptides are incubated with a constant dilution of the aPL antibody. The dilution of the aPL antibody was previously determined by titering the antibody against the tetravalent peptide and selecting a dilution on the downslope of the titration curve. After incubating the antibody and monomeric peptides for one hour, the antibody/peptide solutions are added to the microtitration wells and a standard calorimetric ELISA is performed. The concentration of each monomeric peptide that decreases binding of the aPL antibody with the tetravalent peptide is determined by plotting the colorimetric readings obtained for each well. The 50% inhibition point is used as the measure of the relative strength of binding for the monomeric peptides.

A variation of this assay uses microtitration plates coated with human β2-glycoprotein I/cardiolipin (β2-GPI/CL) instead of tetravalent peptide and tests the ability of monomeric peptides to block the binding of aPL antibody to the epitope(s) on β2-GPI/CL. In this assay, IgG-depleted human serum at an optimized concentration is used as a source of β2-GPI. The monomeric peptides at several concentrations are incubated with an optimized concentration of aPL antibody in a manner analogous to the assay which employs tetravalent peptide as a plate substrate. Following the incubation of aPL/peptide in (β2-GPI/CL) plates, antibody binding and the peptide concentration required for 50% inhibition is determined at half-maximal absorbance as in the tetravalent assay.

(viii) Evaluation of amino acid contributions to binding by substitution and deletion synthesis The desired epitope for tolerance induction should have as strong an interaction with as many of the aPL antibodies as possible but not contain any unnecessary residues. In order to deduce the minimum constitution of an epitope, analogs of each peptide are made (i) that lack given residues, for example, the framework residues at the carboxyl and/or amino termini are deleted, or (ii) in which amino acid substitutions have been made which differ from sequences found in the epitope library screen. These amino acid substitutions may be either natural, e.g., isoleucine for leucine, or unnatural, e.g., alpha methyl proline for proline. The effect of these deletions and/or substitutions are then measured via peptide-competition ELISA.

(ix) Grouping of aPL Sera Specificities by Mutagenesis of the 5th domain of $\beta_2$-GPI For a tolerogen to be generally effective, it must bind a major portion of the aPL antibodies in the majority of patients. It is important to determine if several antibodies from different patients bind identical residues within the eighty-four amino acid 5th domain of $\beta_2$-GPI which has been suggested by others to contain the target epitope. If several antibodies bind identical residues, a single mimotope derived from the structural data of the peptides can be constructed which will react with all the antibodies. On the other hand, if the antibodies bind to different residues, a unique tolerogen would be required for each antibody. Site-directed mutagenesis was performed to identify if key residues involved in aPL antibody binding reside in the 5th domain of $\beta_2$-GPI. The resulting mutant $\beta_2$-GPIs were assayed for reactivity with several aPL antibodies. The results were inconclusive. A fusion protein comprising the 5th domain of $\beta_2$-GPI and glutathionine S transferase (GST) was obtained from A. Steinkasserer and expressed in *E. coli* (Steinkasserer et al. (1992) *FEBS Lett*. 313:193–197). This fusion protein was successfully substituted for native $\beta_2$-GPI in the ACA ELISA. Amino acid substitutions are engineered using standard site-directed mutagenesis.

I. Isolation of Synthetic aPL Epitopes

Antibody ACA-6501, from a patient with a GPL score of 151 (high titer) and a history of recurrent stroke, fetal loss, lupus and three aortic valve replacements was immunoaffinity purified on cardiolipin liposomes. The antibody was used in four separate phage library screens, using the xy, the xyz, the xy'z, and a special pro/cys-bounded 7-mer library where, based on the previous screens, Arg was fixed at the seventh position. As shown in Table 1, 36 sequences were obtained in phage that micropanned (out of 140 tested). These appear quite homologous and the conserved DR residues at positions 6 and 7 are notably striking. The consensus sequence is CLLLAPDRC (SEQ ID NO:9). Despite this homology, only seven phage (see Table 2) were positive after phage-ELISA colorimetric testing. Screening the xy'z phage with affinity purified ACA-6626 (from a patient with a high, but lower than ACA-6501, titer) yielded five unique sequences that were phage-ELISA tested. None were color positive but two were positive when the ELISA immunoconjugate was developed with a chemiluminescent substrate. The sequence motif associated with ACA-6626 appears related but is different from that seen with ACA-6501 (see Table 3). Both antibodies preferred the cys-bounded (probably cyclized and constrained) epitopes over the open pro-bounded sequences.

TABLE 1

ACA-6501 Phage Library Sequences

| Clone | Sequence | Clone | Sequence |
|---|---|---|---|
| xy Library | | | |
| 2101 (SEQ ID NO:10) | CNILVLDRC | | |
| xyz Library | | | |
| 5A12 (SEQ ID NO:11) | CLILAPDRC | 3C10 (SEQ ID NO:17) | CILLAKNRC |
| 2D7 (SEQ ID NO:12) | CLLLAPDRC | 3C5 (SEQ ID NO:18) | CIVLVPDRC |
| 3B6 (SEQ ID NO:13) | CLVLALDRC | 2F4 (SEQ ID NO:19) | CLVIALDRC |
| 3E4 (SEQ ID NO:14) | CLFVALDRC | 5B1 (SEQ ID NO:20) | CWFRSQSSC |
| 3E7 (SEQ ID NO:15) | CILLAHDRC | 3E11 (SEQ ID NO:21) | CSPILRGNC |
| 2H1 (SEQ ID NO:16) | CIILAPGRC | 3E8 (SEQ ID NO:22) | CHKFFWLTC |
| xy'z Library | | | |
| 2A10 (SEQ ID NO:23) | CTILAPDRC | 2D12 (SEQ ID NO:28) | CLVLAADRC |
| 2G12 (SEQ ID NO:24) | CLLITPDRC | 3B10 (SEQ ID NO:29) | CLLLAPDRC |
| 2G11 (SEQ ID NO:25) | CLLITHDRC | 3F2 (SEQ ID NO:30) | CFFHFDHSC |
| 2F10 (SEQ ID NO:26) | CNILVLDRC | 2D3 (SEQ ID NO:31) | CPLHTHHTC |
| 2E3 (SEQ ID NO:27) | CPLITHDRC | | |
| Custom $(X)_6$R Library | | | |
| G11 (SEQ ID NO:32) | CTILTPDRC | 1A4 (SEQ ID NO:40) | CNLLALDRC |
| 2H5 (SEQ ID NO:33) | CTILTPDRC | 2H6 (SEQ ID NO:41) | CNLLAIDRC |
| 2H2 (SEQ ID NO:34) | CTILTLDRC | 1C3 (SEQ ID NO:42) | CLLLAIDRC |
| 2H10 (SEQ ID NO:35) | CTLLTPDRC | 1D10 (SEQ ID NO:43) | CTIITQDRC |
| 2E10 (SEQ ID NO:36) | CIQLTPDRC | 2H4 (SEQ ID NO:44) | CNIITRDRC |
| 1B7 (SEQ ID NO:37) | CHLLTPDRC | 2G12 (SEQ ID NO:45) | CILHAAHRC |

TABLE 1-continued

ACA-6501 Phage Library Sequences

| Clone | | Sequence | Clone | | Sequence |
|---|---|---|---|---|---|
| 2H1 | (SEQ ID NO:38) | CLILTPDRC | 1A9 | (SEQ ID NO:46) | CSSKSYWRC |
| 2H12 | (SEQ ID NO:39) | CSILAPDRC | | | |

TABLE 2

ACA-6501 Colorimetric ELISA-positive Phage

| Clone | | Sequence | Clone | | Sequence |
|---|---|---|---|---|---|
| 5A12 | (SEQ ID NO:11) | CLILAPDRC | 3B6 | (SEQ ID NO:13) | CLVLALDRC |
| 2H1 | (SEQ ID NO:38) | CLILTPDRC | 2G11 | (SEQ ID NO:32) | CTILTPDRC |
| 3B10 | (SEQ ID NO:29) | CLLLAPDRC* | 3E7 | (SEQ ID NO:15) | CILLAHDRC |
| 2H2 | (SEQ ID NO:34) | CTILTLDRC | | | |

*Corresponds to consensus or average sequence

TABLE 3

ACA-6626 xy'z Phage Library Sequences

| Clone | | Sequence | Clone | | Sequence |
|---|---|---|---|---|---|
| 4B11 | (SEQ ID NO:47) | CGNAADARC | 4G7 | (SEQ ID NO:50) | CTNLTDSRC |
| 4D3 | (SEQ ID NO:48) | CTNWADPRC | 4A2 | (SEQ ID NO:51) | CGNPTDVRC |
| 4C7 | (SEQ ID NO:49) | CGNIADPRC | | | |

ACA-6644 is another high-titered aPL antibody that was used to screen the pooled p-III phage libraries according to methods described herein. The following sequences were discovered:

| | | |
|---|---|---|
| ACA-6644/CBc | GILLNEFA | (SEQ ID NO:52) |
| ACA-6644/CBd | GILTIDNL | (SEQ ID NO:53) |
| ACA-6644/CBf | GILALDYV | (SEQ ID NO:54) |

These sequences all were derived from the component "z" epitope library that lacks phage framework residues at the N-terminus. When synthesized as peptides the sequences were immunoreactive with several ACA sera including ACA-6644 and ACA-6501. Analysis revealed unsuspected homologies with the sequences previously obtained with ACA-6501 as illustrated in Table 4.

TABLE 4

| ACA-6644/CBd | | G | ILTID | N | L | (SEQ ID NO:53) |
|---|---|---|---|---|---|---|
| ACA-6501/2H2 | C | T | ILTLD | R | C | (SEQ ID NO:34) |
| ACA-6644/CBf | | G | ILALD | Y | V | (SEQ ID NO:54) |
| ACA-6501/2F10 | C | N | ILVLD | R | C | (SEQ ID NO:10) |

TABLE 4-continued

| ACA-6644/CBc | | G | ILLNE | F | A | (SEQ ID NO:52) |
|---|---|---|---|---|---|---|
| ACA-6501/1D10 | C | T | IITQDR | C | C | (SEQ ID NO:43) |

The convergent sequence homology from two very dissimilar source libraries screened by these two aPL antibodies suggests that the sequences may mimic a major, perhaps immunodominant, region in the native target antigen.

Screening of the p-III libraries with ACA-6701 yielded two unique sequences with a high degree of internal homology but unlike others previously obtained with other aPL antibody. The sequences are as shown:

| | |
|---|---|
| ACA-6701/3B1 LSDPGYVRNIFH | (SEQ ID NO:55) |
| ACA-6701/3E1 LTDPRYTRDISNFTD | (SEQ ID NO:56) |

As resin-bound peptides, the sequences were strongly immunoreactive with the parent serum (ACA-6701) but were minimally cross-reactive with other aPL antibodies.

Continued screening of random pIII phage libraries with affinity purified ACA antibody resulted in the discovery of a peptide that displayed significant crossreactivity with all nine affinity purified ACA antibodies against which it was initially tested. Subsequent testing determined that this peptide, ACA-6641/3G3 having the sequence AGP-CLGVLGKLC-PG (SEQ ID NO:55)(LJP 688) was the most highly cross-reactive peptide of any peptide previously discovered. When tested against 65 high titer ACA antisera, 6641/3G3 (LJP 688) or truncated versions thereof were highly cross-reactive with 93.8% of the sera, 3.1% moderately cross-reactive and was not cross-reactive with 3.1%. Chemical optimization of this peptide was pursued by truncation, systematic amino acid substitution, and non-disulfide cyclization studies.

The motifs of several peptides selected from the random phage library screening is set forth below.

TABLE 5

| ACA Antibody | | Phage Insert Sequence |
|---|---|---|
| 6501 | (SEQ ID NO:29) | C L L L A P D R C (3B10) |
| 6626 | (SEQ ID NO:48) | C T N W A D P R C |
| 6641 | (SEQ ID NO:58) | C L G V L G K L C (3G3) |
| 6644 | (SEQ ID NO:54) | G I L A L D Y V |
| 6701 | (SEQ ID NO:56) | L T D P R Y T R D I S N F T D |
| 6707 | (SEQ ID NO:59) | C A H P D W D R C |

Figure 2:
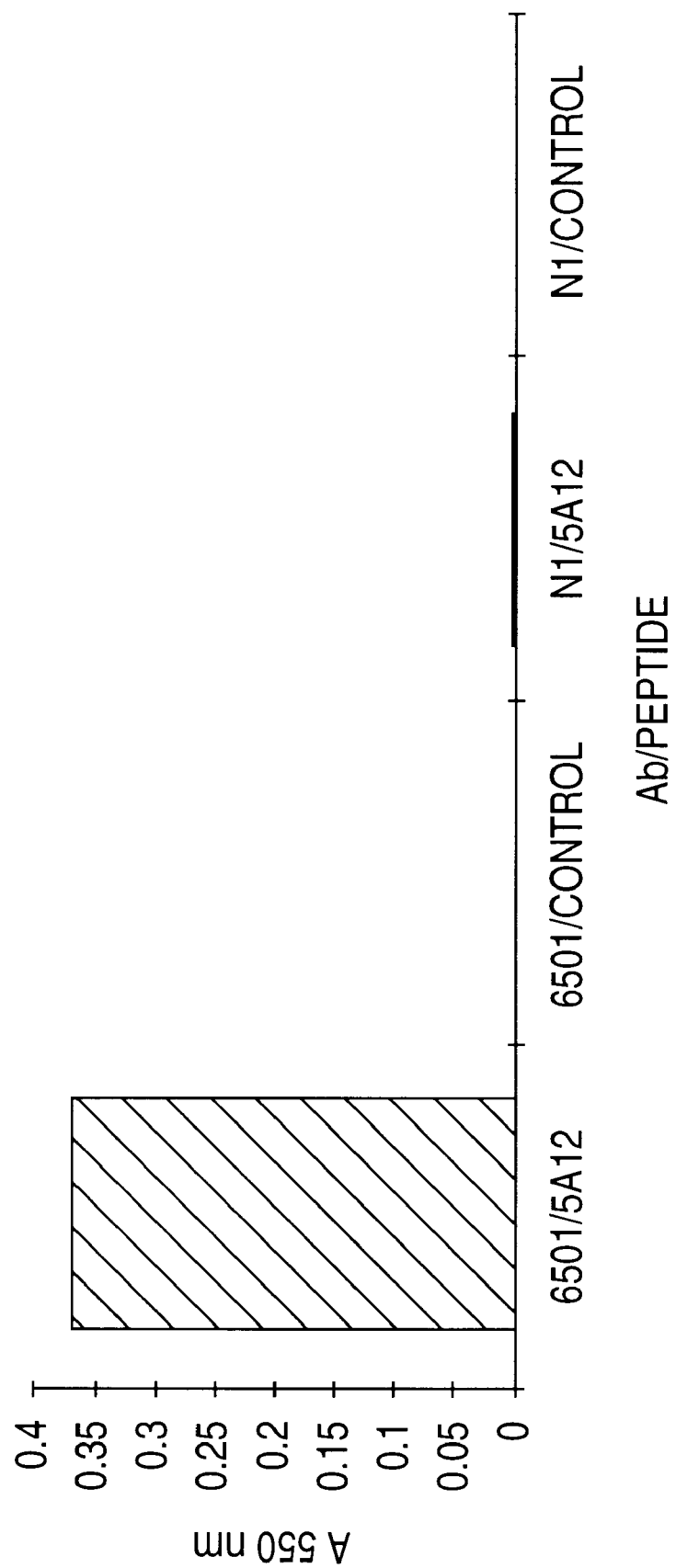
FIG. 2 shows that resin-bound analog 5A12 immunospecifically binds to affinity-purified IgG designated ACA-6501.

J. Immunoreactivity of aPL-related Peptides with Affinity Purified IgG aPL Antibody Phage sequences obtained with affinity-purified ACA-6501 and found to be phage-ELISA-positive were synthesized on a solid support recently developed for combinatorial synthetic peptide libraries. This support, a Rapp resin, has a high peptide density and uses a hydrophilic polyethyleneglycol spacer before the first amino acid is coupled. The synthesis resulted in resin-bound peptide that was ideally suited for antibody binding studies. As shown in FIG. 2, peptide 5A12 (sequence CLILAPDRC)(SEQ ID NO:11) dramatically outperformed an unrelated control peptide while not significantly binding normal IgG. Similar results were obtained with the other phage-ELISA-positive peptides tested. In the experiment shown, resin peptide-bound affinity-purified ACA-6501 aPL antibody was detected by an immunoconjugate color reaction.

K. aPL Serum Antibody Reactivity with Synthetic Peptides

Figure 3:
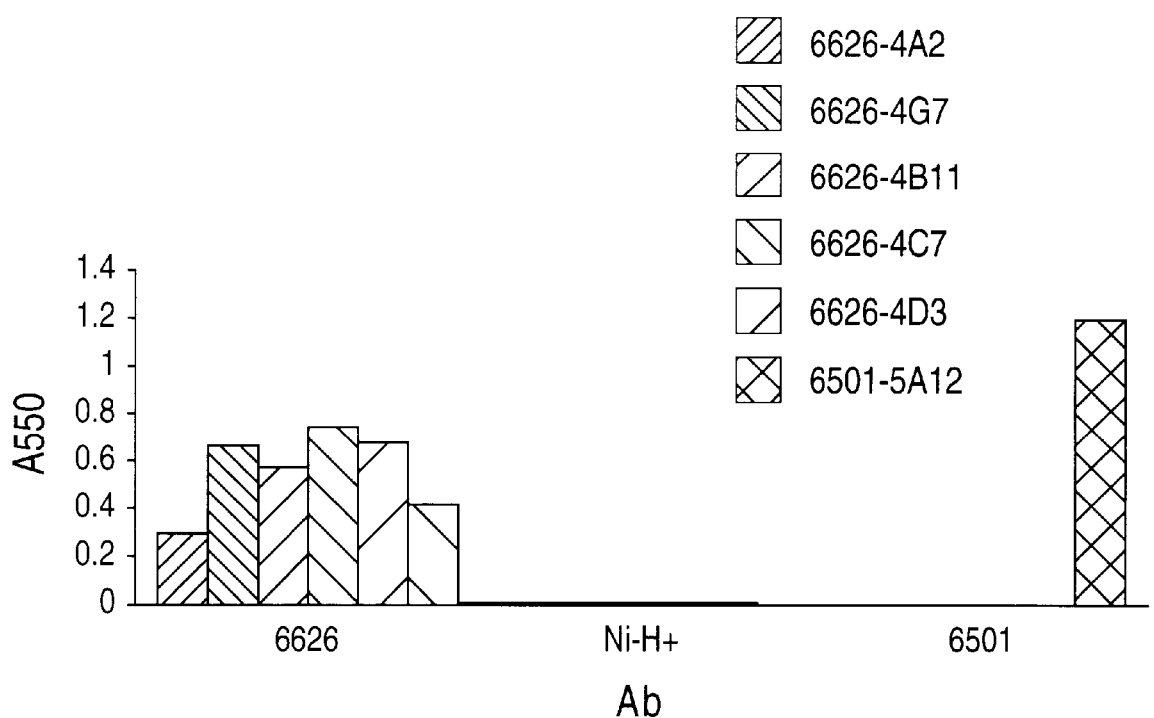
FIG. 3 illustrates that the aPL antibody-binding analogs derived from screening with ACA-6626 bound aPL antisera but did not bind normal sera.

The discovery that resin-bound peptides could bind aPL immunospecifically using serum significantly enhanced the ability to test aPL antibodies. As shown in FIG. 3, the peptide derived from screening with ACA-6626 bound aPL antiserum but did not demonstrate significant binding of normal serum. FIG. 3 also illustrates the immunospecific-binding behavior of ACA6501-5A12 peptide towards aPL serum. Binding of normal serum to peptide 5A12 was nil in data not shown.

Figure 4:
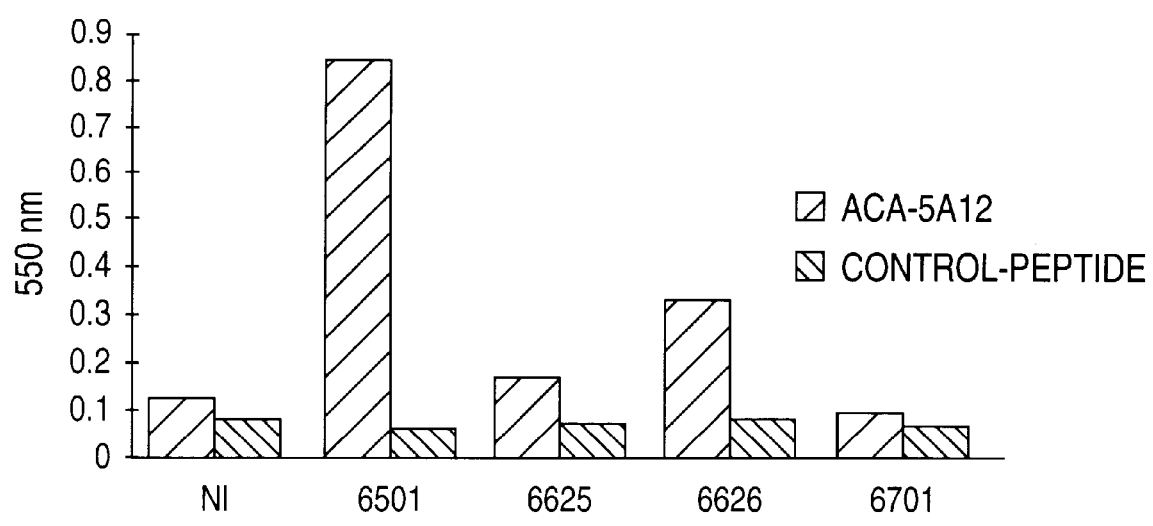
FIG. 4 also illustrates that the ACA6501/5A12 analog immunospecifically binds ACA-6501 antiserum and is crossreactive with ACA-6626.
Figure 5:
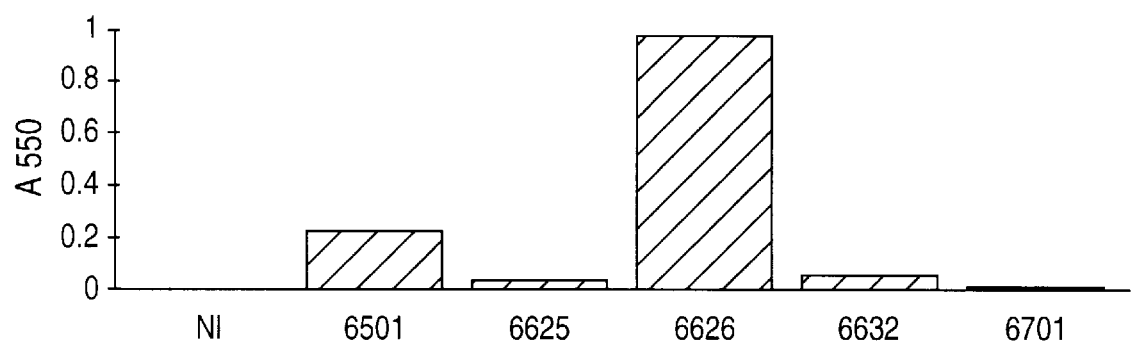
FIG. 5 illustrate that while the ACA6501/5A12 and ACA6626/4D3 aPL antibody-binding analogs derived from screening with methods within the instant invention bind preferentially with the screening antibody, a significant degree of crossreactivity was detected.
Figure 6A:
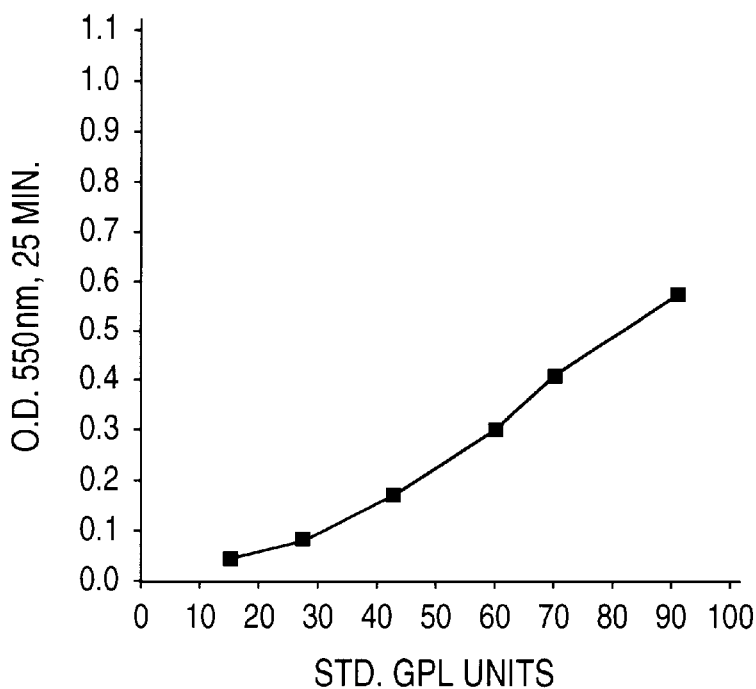
FIG. 6 illustrates method for calculating the GPL value for ACA-6501 aPL antibody.
Figure 6B:
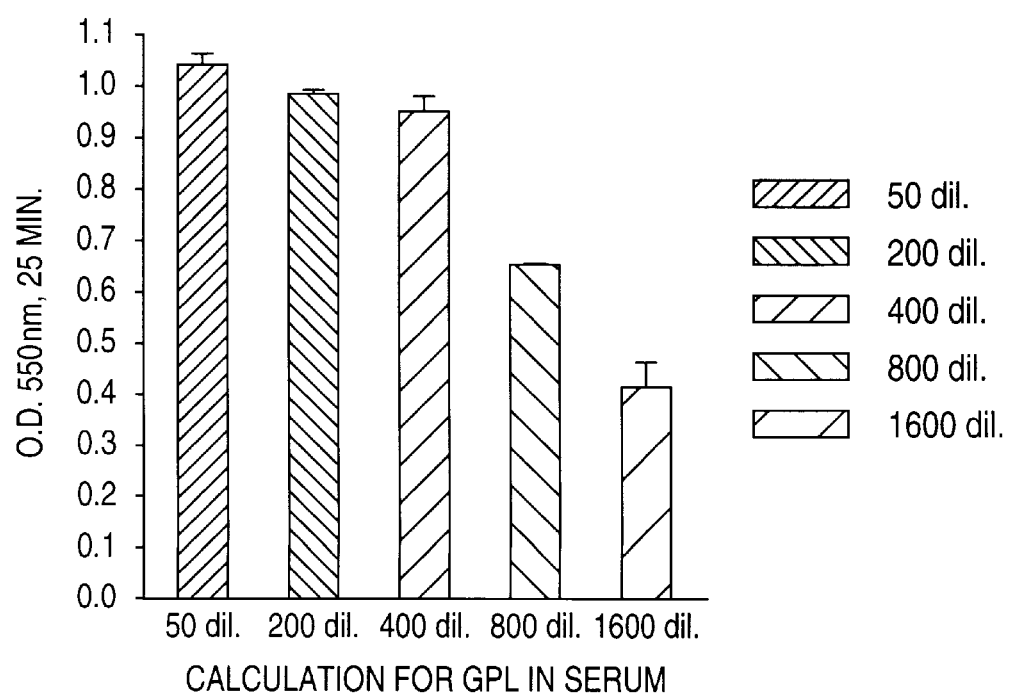
Figure 7:
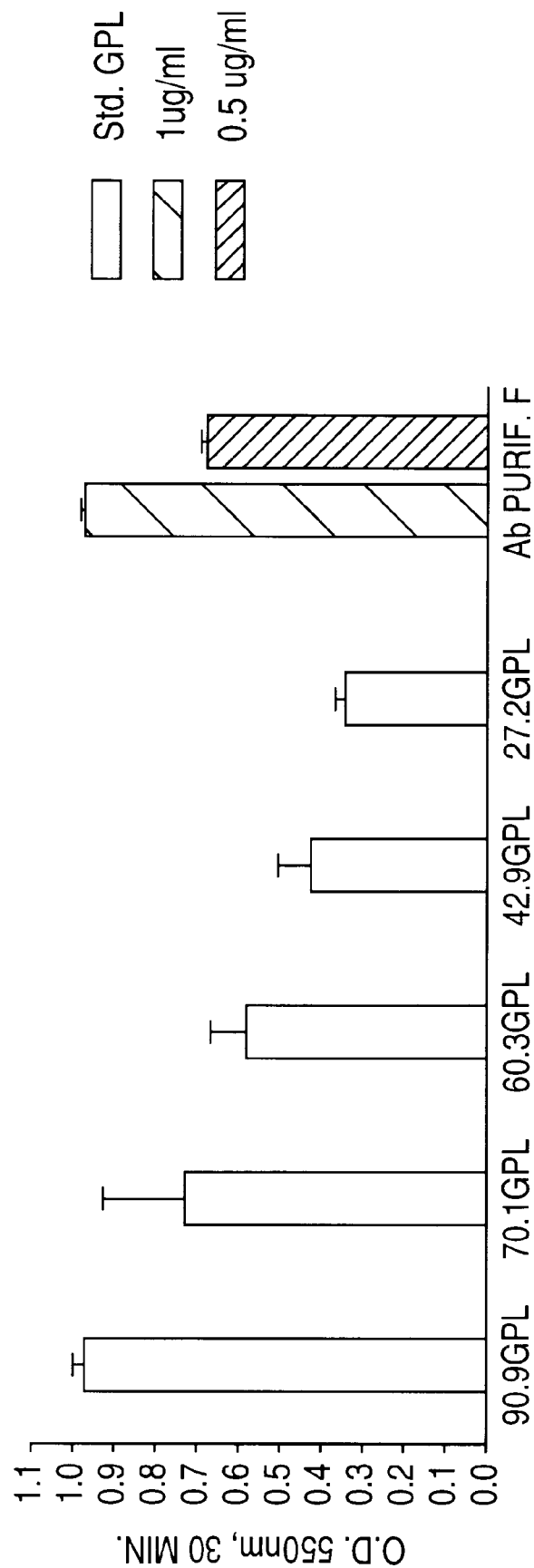
FIG. 7 shows the activity of affinity-isolated ACA-6501 compared to GPL standard sera.

L. Crossreactivity of Synthetic Peptides Towards aPL Antiserum that was not the Source of the Library Screening Antibody Two peptides were selected for aPL sera testing, one (5A12) representing the ACA-6501 screen and another one (4D3) representing the ACA-6626 screen. As shown in FIGS. 4 and 5, each of the peptides reacted preferentially with the parent serum of the screening antibody. However, a significant degree of crossreactivity was detectable especially between ACA-6501 and ACA-6626. A survey of 19 patient sera with low or no GPL score and of 13 pathologic sera with moderate to high GPL carried out with the 5A12 resin-bound peptide showed 8 of the 13 pathologic samples with detectable peptide binding while only 2 out of 19 control samples showed low peptide binding. These results evidence that synthetic peptides are useful for diagnostic or prognostic assays in stroke patient care.

Figure 14:
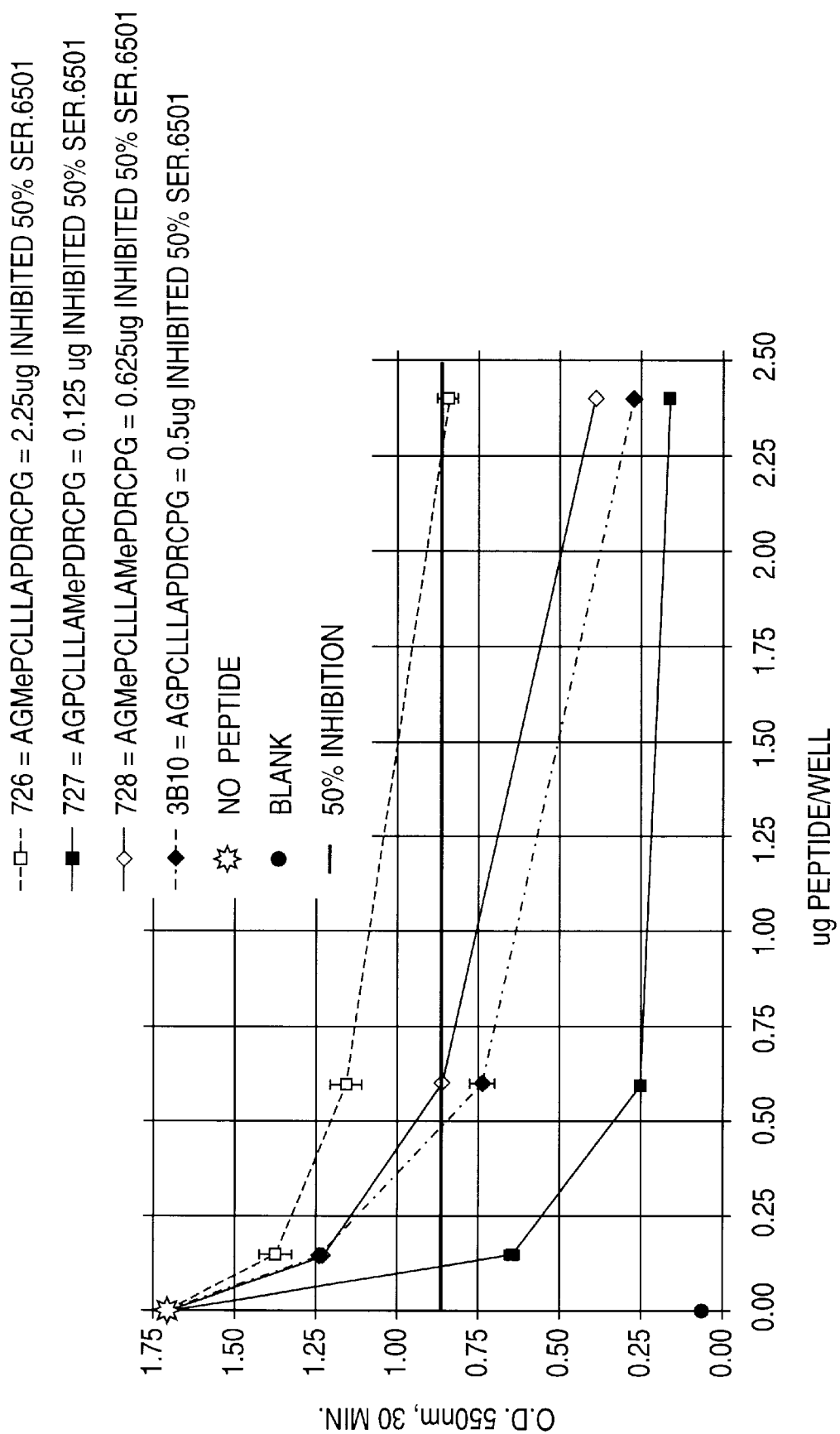
FIG. 14 (SEQ ID NO:4 through SEQ ID NO:7) illustrates the effects of substituting α-Me-Pro at positions 3, 9 and both 3 and 9 in peptide 3B10. Substitution of α-Me-Pro at position 9 increased activity of the peptide four-fold compared to the "native" peptide.
Figure 15:
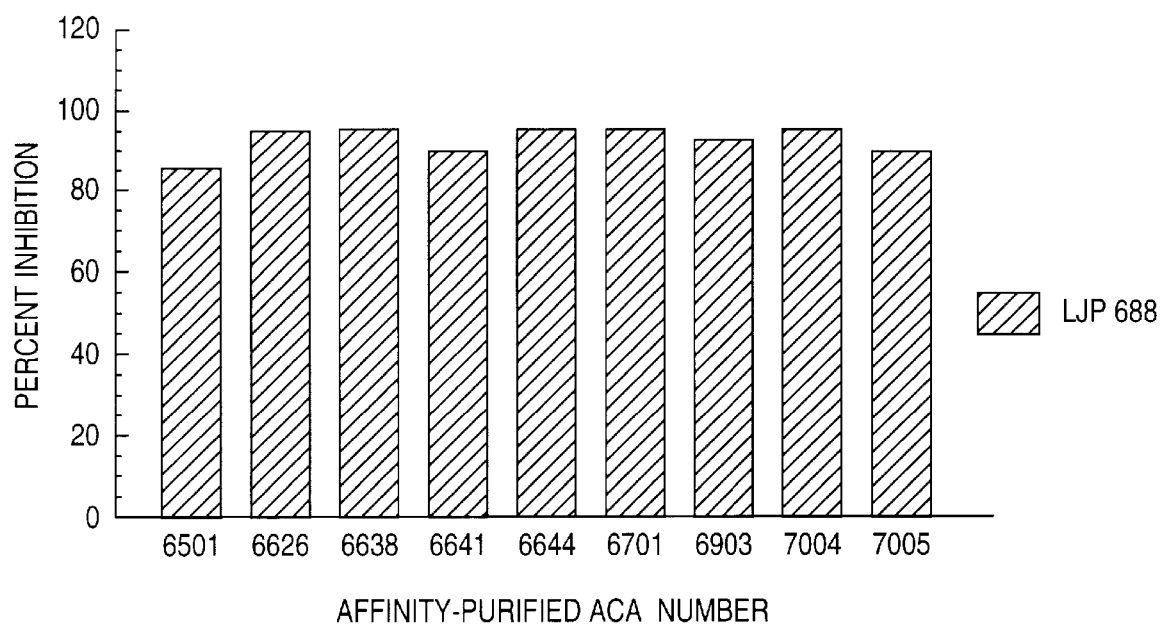
FIG. 15 shows that peptide 6641/3G3 (LJP 688) is highly cross-reactive with nine affinity-purified ACA antibodies.

As noted in Section I above, one synthetic peptide, 6641/3G3 was tested against several high titer ACA antisera. This peptide was found to be crossreactive with the vast majority of ACA antisera tested as illustrated in FIG. 14. 6641/3G3 demonstrated dose-dependent cross-reactivity with 10 of 10 ACA antibodies with complete inhibition (>80%) at 1.8 mg/mL and was shown to be specific for ACA antibodies as demonstrated in Table 5 below.

TABLE 5

CROSSREACTIVITY DATA FOR
AGP-CLGVLGKLC-PG (LJP 688)
ACA SERA WITH CARDIOLIPIN/β2-GPI-COATED PLATES

| ACA Serum Nr. | IC50, mg/mL, for peptide LJP 688 |
|---|---|
| [1] 6501 RS, RFL | 0.89, 1.1 |
| [2] 6626 RS | 1.09 |
| [3] 6635 RS | 1 |
| [4] 6638 RS | 0.81 |
| [5] 6641 RS | 0.89, 0.51 |
| [6] 6644 RS | 0.76 |
| [7] 6701 RS | 1.07 |
| [8] 6903 RS | 0.8 |
| [9] 7004 RFL | 0.67 |
| [10] 7005 RFL | 0.75 |
| mean ± sd | 0.86 ± 0.16 |

RS = recurrent stroke
RFL = recurrent fetal loss

M. New Synthetic Peptide Methodologies

The identification of new candidate sequences by aPL library screening required testing of the new synthetic peptides for antibody binding. With Rapp resin of known peptide substitution, it is possible to carry out quantitative binding studies such as saturation binding analysis and equilibrium measurements using radiolabeled aPL IgG.

Peptide synthesis allows the molecular dissection of the mimotope by selective synthesis. This includes the modification of each amino acid along the chain with the goal of enhancing antibody binding. Selective synthesis reveals the relative importance of each amino acid in the sequence. If necessary, selective substitution at particular residue locations can be designed to maintain B cell reactivity while abolishing any T cell proliferative reactivity discovered during T cell assays.

Peptide 6641/3G3 (LJP 688) was subjected to a number of analyses. The analyses included truncation at both the N-terminus and the C-terminus, disulfide substitution, substitution of alanine and glycine for amino acids in positions 2 through 8, substitution of branched aliphatic amino acids in positions 2, 4, 5 and 8, substitution of amino acids affecting conformation of the peptide, including substitution of α-methyl amino acids, substitution of basic amino acids in position 7, substitution of D-amino acids in positions 2 through 9, and the substitution of N-α-methyl amino acids in positions 1 through 9. The results are shown below in Table 8. The structure/activity relationship of these substitutions and truncations is shown in Table 6.

TABLE 6

OPTIMIZATION OF PEPTIDE 3G3 — Total Peptides: 144

3/28/96

| Position Number | -2 | -1 | 0 | 1 | 2 | 3 | 4 | 5 | 6 | 7 | 8 | 9 | A | B | with ACA 6501 150, µg/mL | std |
|---|---|---|---|---|---|---|---|---|---|---|---|---|---|---|---|---|
| *Truncation analysis (SEQ ID NO: 60 through SEQ ID NO: 65)* | | | | | | | | | | | | | | | | |
| 1 | A | G | P | C | L | G | V | L | G | K | L | C | P | G | 850 | |
| 2 | | G | P | C | L | G | V | L | G | K | L | C | P | G | 180 | |
| 3 | | | P | C | L | G | V | L | G | K | L | C | P | G | 420 | |
| 4 | | | | C | L | G | V | L | G | K | L | C | P | G | 460 | |
| 5 | A | G | P | C | L | G | V | L | G | K | L | C | G | | 450 | |
| 6 | | | | C | L | G | V | L | G | K | L | C | | | 10 | #906 (LJP 690) |
| *Disulfide surrogates (SEQ ID NO: 66 thought SEQ ID NO: 69)* | | | | | | | | | | | | | | | | |
| 1 | | | | C | L | G | V | L | G | K | L | C | | | 110 | #952 = 100 |
| 2 | | | | Hc | L | G | V | L | G | K | L | C | | | 46 | |
| 3 | | | | C | L | G | V | L | G | K | L | Hc | | | 92 | |
| 4 | | | | Hc | L | G | V | L | G | K | L | Hc | | | 80 | |
| *Ala scan (SEQ ID NO: 70 through SEQ ID NO: 76)* | | | | | | | | | | | | | | | | |
| 1 | | | | C | A | G | V | L | G | K | L | C | | | 200 | #952 = 80 |
| 2 | | | | C | L | A | V | L | G | K | L | C | | | 170 | |
| 3 | | | | C | L | G | A | L | G | K | L | C | | | 260 | |
| 4 | | | | C | L | G | V | A | G | K | L | C | | | Inf. | |
| 5 | | | | C | L | G | V | L | A | K | L | C | | | 40 | |
| 6 | | | | C | L | G | V | L | G | A | L | C | | | Inf. | |
| 7 | | | | C | L | G | V | L | G | K | A | C | | | 360 | |
| *Gly scan (SEQ ID NO: 77 through SEQ ID NO: 81)* | | | | | | | | | | | | | | | | |
| 1 | | | | C | G | G | V | L | G | K | L | C | | | 310 | #952 = 120 |
| 2 | | | | C | L | G | G | L | G | K | L | C | | | Inf. | |
| 3 | | | | C | L | G | V | G | G | K | L | C | | | Inf. | |
| 4 | | | | C | L | G | V | L | G | G | L | C | | | Inf. | |
| 5 | | | | C | L | G | V | L | G | K | G | C | | | 500 | |
| *Sequence optim. Branched aliphatic amino acids (SEQ ID NO: 82 through SEQ ID NO: 109)* | | | | | | | | | | | | | | | | |
| 1 | | | | C | I | G | V | L | G | K | L | C | | | 60 | #910 = 40 |
| 2 | | | | C | V | G | V | L | G | K | L | C | | | 130 | |
| 3 | | | | C | M | G | V | L | G | K | L | C | | | | |
| 4 | | | | C | Cy | G | V | L | G | K | L | C | | | | |
| 5 | | | | C | tL | G | V | L | G | K | L | C | | | | |
| 6 | | | | C | mL | G | V | L | G | K | L | C | | | | |
| 7 | | | | C | Iv | G | V | L | G | K | L | C | | | | |
| 8 | | | | C | L | G | L | L | G | K | L | C | | | | |
| 9 | | | | C | L | G | I | L | G | K | L | C | | | | |
| 10 | | | | C | L | G | M | L | G | K | L | C | | | | |
| 11 | | | | C | L | G | Cy | L | G | K | L | C | | | | |
| 12 | | | | C | L | G | tL | L | G | K | L | C | | | | |
| 13 | | | | C | L | G | mL | L | G | K | L | C | | | | |
| 14 | | | | C | L | G | Iv | L | G | K | L | C | | | | |
| 15 | | | | C | L | G | V | I | G | K | L | C | | | | |
| 16 | | | | C | L | G | V | V | G | K | L | C | | | | |
| 17 | | | | C | L | G | V | M | G | K | L | C | | | | |
| 18 | | | | C | L | G | V | Cy | G | K | L | C | | | | |
| 19 | | | | C | L | G | V | tL | G | K | L | C | | | | |
| 20 | | | | C | L | G | V | mL | G | K | L | C | | | | |
| 21 | | | | C | L | G | V | Iv | G | K | L | C | | | | |
| 22 | | | | C | L | G | V | L | G | K | I | C | | | | |
| 23 | | | | C | L | G | V | L | G | K | V | C | | | | |
| 24 | | | | C | L | G | V | L | G | K | M | C | | | | |
| 25 | | | | C | L | G | V | L | G | K | Cy | C | | | | |
| 26 | | | | C | L | G | V | L | G | K | tL | C | | | | |
| 27 | | | | C | L | G | V | L | G | K | mL | C | | | | |
| 28 | | | | C | L | G | V | L | G | K | Iv | C | | | | |
| *Conformational scan amino acids (SEQ ID NO: 110 throught SEQ ID NO: 140)* | | | | | | | | | | | | | | | | |
| 1 | | | | C | L | P | V | L | G | K | L | C | | | | |
| 2 | | | | C | L | mP | V | L | G | K | L | C | | | | |
| 3 | | | | C | L | mA | V | L | G | K | L | C | | | | |
| 4 | | | | C | L | cG | V | L | G | K | L | C | | | | |
| 5 | | | | C | L | G | V | L | P | K | L | C | | | | |
| 6 | | | | C | L | G | V | L | mP | K | L | C | | | | |
| 7 | | | | C | L | G | V | L | mA | K | L | C | | | | |
| 8 | | | | C | L | G | V | L | cG | K | L | C | | | | |
| 9 | | | | C | L | dA | V | L | G | K | L | C | | | | |
| 10 | | | | C | L | G | V | L | dA | K | L | C | | | | |
| 11 | | | | C | P | G | V | L | G | K | L | C | | | 160 | #952 = 100 |
| 12 | | | | C | L | P | V | L | G | K | L | C | | | 340 | (Pro scan) |

TABLE 6-continued

|  |  | 1 | 2 | 3 | 4 | 5 | 6 | 7 | 8 | 9 |  |  |
|---|---|---|---|---|---|---|---|---|---|---|---|---|
|  | 13 | C | L | G | P | L | G | K | L | C | 180 |  |
|  | 14 | C | L | G | V | P | G | K | L | C | Inf. |  |
|  | 15 | C | L | G | V | L | P | K | L | C | 350 |  |
|  | 16 | C | L | G | V | L | G | P | L | C | 160 |  |
|  | 17 | C | L | G | V | L | G | K | P | C | 550 |  |
|  | 18 | C | pG | G | V | L | G | K | L | C | 130 | #910 = 40 |
|  | 19 | C | L | pG | V | L | G | K | L | C | 70 |  |
|  | 20 | C | L | G | pG | L | G | K | L | C | 70 |  |
|  | 21 | C | L | G | V | pG | G | K | L | C | 35 |  |
|  | 22 | C | L | G | V | L | pG | K | L | C | 30 | #910 = 5 |
|  | 23 | C | L | G | V | L | G | pG | L | C | 230 |  |
|  | 24 | C | L | G | V | L | G | K | pG | C | 80 |  |
| alpha Me AA | 25 | C | alB | G | V | L | G | K | L | C | 370 | 910 = 40 |
|  | 26 | C | L | alB | V | L | G | K | L | C | 80 |  |
|  | 27 | C | L | G | alB | L | G | K | L | C | 110 |  |
|  | 28 | C | L | G | V | alB | G | K | L | C | Inf. |  |
|  | 29 | C | L | G | V | L | alB | K | L | C | 110 |  |
|  | 30 | C | L | G | V | L | G | alB | L | C | 460 |  |
|  | 31 | C | L | G | V | L | G | K | alB | C | >470 |  |

Basic amino acid (SEQ ID NO:141 through SEQ ID NO:143)

|  |  | 1 | 2 | 3 | 4 | 5 | 6 | 7 | 8 | 9 |  |  |
|---|---|---|---|---|---|---|---|---|---|---|---|---|
|  | 1 | C | L | G | V | L | G | R | L | C | 160 | #952 = 120 |
|  | 2 | C | L | G | V | L | G | Or | L | C | 40 | 910 = 50 |
|  | 3 | C | L | G | V | L | G | mK | L | C |  |  |

D amino acids (lower case d) (SEQ ID NO:144 through SEQ ID NO:166)

|  |  | 1 | 2 | 3 | 4 | 5 | 6 | 7 | 8 | 9 |  |  |
|---|---|---|---|---|---|---|---|---|---|---|---|---|
|  | 1 | dP | C | L | G | V | L | G | K | L | C | 120 | #952 = 120 |
|  | 2 |  | C | dL | G | V | L | G | K | L | C | 180 | #952 = 30 |
|  | 3 |  | C | L | G | dV | L | G | K | L | C | 260 | #952 = 30 |
|  | 4 |  | C | L | G | V | dL | G | K | L | C | 230 | #952 = 30 |
|  | 5 |  | C | L | G | V | L | G | dK | L | C | 170 | #952 = 60 |
|  | 6 |  | C | L | G | V | L | G | K | dL | C | 140 | #952 = 30 |
|  | 7 |  | C | dL | G | dV | L | G | K | L | C |  |  |
|  | 8 |  | C | dV | G | dV | L | G | K | L | C |  |  |
|  | 9 |  | C | dL | G | dL | L | G | K | L | C |  |  |
|  | 10 |  | C | L | G | dV | dL | G | K | L | C | 50 | #952 = 30 |
|  | 11 |  | C | L | G | dV | dV | G | K | L | C |  |  |
|  | 12 |  | C | L | G | dV | dV | G | K | L | C |  |  |
|  | 13 |  | C | L | G | dL | dL | G | K | L | C |  |  |
|  | 14 |  | C | L | G | V | dL | G | dK | L | C |  |  |
|  | 15 |  | C | L | G | V | dK | G | dL | L | C |  |  |
|  | 16 |  | C | L | G | V | dL | G | dL | L | C |  |  |
|  | 17 |  | C | L | G | V | dK | G | dK | L | C |  |  |
|  | 18 |  | C | L | G | V | L | G | dK | dL | C | 150 | #952 = 50 |
|  | 19 |  | C | L | G | V | L | G | dL | dK | C |  |  |
|  | 20 |  | C | L | G | V | L | G | dK | dK | C |  |  |
|  | 21 |  | C | L | G | V | L | G | dL | dL | C |  |  |
|  | 22 |  | C | L | G | V | L | dA | K | L | C | 140 | #952 = 30 |
|  |  |  | C | L | G | V | L | G | K | L | dC | 140 | #952 = 50 |

N-Me amino acids (nAA) (SEQ ID NO: 167 through SEQ ID NO: 175)

|  |  | 1 | 2 | 3 | 4 | 5 | 6 | 7 | 8 | 9 |  |  |
|---|---|---|---|---|---|---|---|---|---|---|---|---|
|  | 1 | nC | L | G | V | L | G | K | L | C |  |  |
|  | 2 | C | nL | G | V | L | G | K | L | C |  |  |
|  | 3 | C | L | nG | V | L | G | K | L | C | 70 | #952 = 50 |
|  | 4 | C | L | G | nV | L | G | K | L | C | 220 |  |
|  | 5 | C | L | G | V | nL | G | K | L | C | 180 |  |
|  | 6 | C | L | G | V | L | nG | K | L | C | 550 |  |
|  | 7 | C | L | G | V | L | G | nK | L | C |  |  |
|  | 8 | C | L | G | V | L | G | K | nL | C | 240 | #952 = 50 |
|  | 9 | C | L | G | V | L | G | K | L | nC |  |  |

Others (SEQ ID NO: 176 through SEQ ID NO: 181)

|  |  |  | 1 | 2 | 3 | 4 | 5 | 6 | 7 | 8 | 9 |  |  |  |
|---|---|---|---|---|---|---|---|---|---|---|---|---|---|---|
|  | 1 | Y ATU | C | L | G | V | L | G | K | L | C | ATU-Y | 300 | #952 = 50 |
|  | 2 | Y ATU | C | L | G | V | L | G | K | L | C |  | 170 |  |
|  | 3 |  | C | L | G | V | L | G | K | L | C | TGR re | 500 |  |
|  | 4 |  | C | L | G | V | L | G | K | L | dC | TGR re | 620 |  |
|  | 5 |  | dC | L | G | V | L | G | K | L | C |  |  |  |
|  | 6 |  | dC | L | G | V | L | G | K | L | dC | TGR resin |  |  |

Thioethers: single deletion (SEQ ID NO: 182 through SEQ ID NO: 189)

|  |  | 1 | 2 | 3 | 4 | 5 | 6 | 7 | 8 | 9 |
|---|---|---|---|---|---|---|---|---|---|---|
|  | 1 | Hc | L | G | V | L | A | K | L | C |
|  | 2 | Hc |  | G | V | L | A | K | L | C |
|  | 3 | Hc | L |  | V | L | A | K | L | C |
|  | 4 | Hc | L | G |  | L | A | K | L | C |
|  | 5 | Hc | L | G | V |  | A | K | L | C |
|  | 6 | Hc | L | G | V | L |  | K | L | C |
|  | 7 | Hc | L | G | V | L | A |  | L | C |
|  | 8 | Hc | L | G | V | L | A | K |  | C |

TABLE 6-continued

| | | | | | | | | | | |
|---|---|---|---|---|---|---|---|---|---|---|
| shrink minization (SEQ ID NO: 190 through SEQ ID NO: 192) | | | | | | | | | | |
| 1 | Hc | | | V | L | A | K | L | C | |
| 2 | Hc | | | | L | A | K | L | C | |
| 3 | Hc | | | | L | A | K | | C | |
| branched (SEQ ID NO: 193 through SEQ ID NO: 197) | | | | | | | | | | |
| 1 | Hc | L | G | V | L | G | K | L | Pe | |
| 2 | Hc | L | G | V | L | G | K | L | dPe | |
| 3 | Pe | L | G | V | L | G | K | L | Hc | |
| 4 | dPe | L | G | V | L | G | K | L | Hc | |
| 5 | dPe | L | G | V | L | G | K | L | dPe | |
| D amino acids (SEQ ID NO: 198 through SEQ ID NO: 200) | | | | | | | | | | |
| 1 | dHc | L | G | V | L | G | K | L | C | |
| 2 | dHc | L | G | V | L | G | K | L | dC | |
| 3 | Hc | L | G | V | L | G | K | L | dC | |
| Des amino (SEQ ID NO: 2 through SEQ ID NO: 204 | | | | | | | | | | |
| 1 | By | L | G | V | L | G | K | L | Hc | desamino HHTE |
| 2 | By | L | G | V | L | G | K | L | C | desamino HCTE |
| 3 | Pp | L | G | V | L | G | K | L | Hc | desamino CHTE |
| 4 | Pp | L | G | V | L | G | K | L | C | desamino CCTE |

Abbreviations
Hc homocysteine
Cy cyclohexyl alanine
tL tertiary leucine
mL alpha methyl leucine?
Iv alpha methyl, alpha amino butyric acid?
mP alpha methyl proline
mA alpha methyl alanine
aiB aminoisobutyric acid
pG phenylglycine
cG cyclopropyl glycine
dA D alanine
dP D proline
dL D leucine
dV D valine
dK D lysine
nC N alpha-methyl cysteine
nL N alpha-methyl leucine
nG N-methyl glycine
nV N alpha-methyl valine
nK N alpha-methyl lysine
mK N epsilon-methyl lysine
Pe penicillamine
By butyroyl
Pp proprionyl
Or ornithine

TABLE 7

Structure Activity Relationship of the Crossreactive ACA Epitope

| Structure | | | Relative Activity |
|---|---|---|---|
| AGPCLGVLGKLCPG (3G3) | (LJP 688) | (SEQ ID NO:60) | 100 |
| CLGVLGKLC | (LJP 690) | (SEQ ID NO:65) | 3.5 |
| CLGVLAKLC | | (SEQ ID NO:74) | 1.8 |
| CLGVL$_p$GKLC | | (SEQ ID NO:131) | 1.4 |
| CLG$_d$V$_d$LGKLC | | (SEQ ID NO:153) | 5.9 |
| HcLGVLGKLC (thioether) | | (SEQ ID NO:205) | 1.6 |
| SLGVLGKLS | | (SEQ ID NO:206) | ∞ |
| CLGVAGKLC | | (SEQ ID NO:207) | ∞ |
| CLGVLGALC | | (SEQ ID NO:208) | ∞ |

N. Use of α-methyl Amino Acids Substitutions to Enhance Peptide Immunoreactivity and Confer Resistance to Protease Attack Proline residues have a special significance due to their influence on the chain conformation of polypeptides. They often occur in reverse turns on the surface of globular proteins. In the phage epitope libraries of the present invention, all random peptide inserts are flanked by boundary prolines. In addition, most of the mimotopes discovered with ACA-6501 have a third proline which, based on computer-based predictions, likely exists as part of a β-turn. β-turn mimetics can be used to enhance the stability of reverse turn conformations in small peptides. Such a mimetic is (S)-α-methyl proline (α-MePro), a proline analog that, in addition to stabilizing turn conformations, confers resistance to protease degradation. Protease resistance is a desirable property for a potential drug designed to act in the plasma. Peptide ACA-6501/3B10 AGPCLLLAPDRCPG (SEQ ID NO:7) (insert highlighted) is a consensus peptide. It has a sequence featuring the most prevalent residue at each position based on a comparison with 35 other homologous sequences. Due to its representative character, the sequence was subjected to a number of systematic modifications and deletions and its activity subsequently evaluated by aPL antibody binding. Among the most important findings was the discovery that the prolines at the 3 and 9 positions are important for activity. Proline-3 is derived from the phage framework and is not part of the random insert. The most dramatic effect was obtained by the substitution of α-MePro for proline at the 9-position. This substitution led to a six-fold enhancement in immunoreactivity.

The results of α-methyl and N-α-methyl amino acid substitution studies carried out on peptide 6641/3G3 are shown above in Table 6.

O. Preparation of Cyclic Thioether Analogs

The mimetic peptides identified by the methods of the instant invention can be further modified to contain thioether substitutions. Modification of cyclic disulfide analogs to cyclic thioether analogs will extend the plasma half-life of the analog conjugates and, therefore, require a lower dosage. Cyclic thioether analogs also eliminate the problem of disulfide bond exchange which often occurs with cyclic disulfide polypeptides. In addition, the cyclic thioether analogs may also interfere with MHC Class II presentation to T cells and, thus, facilitate induction of anergy. Finally, the cyclic thioether analogs are useful in the thiol-dependent conjugation reactions used in the production of valency platform molecule conjugates.

Four cyclic thioether analogs were prepared according to the methodology described in co-owned, co-pending patent application, U.S. Ser. No. 08/748,021 now U.S. Pat. No. 5,817,752, which is a continuation of U.S. Ser. No. 08/660,739, now abandoned, which is incorporated herein in its entirety. Using either a RINK™ amide 4-methyl benzhydrylamino resin or MBHA resin, full length peptide analogs of 6641/3G3 were prepared, converted into chloro-peptides, cleaved from a solid support and then cyclized. See Thioether Reaction Scheme below. Suitable cyclic thioether analogs include the analogs shown below.

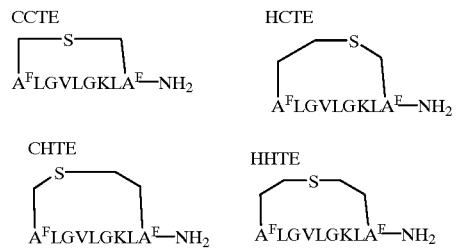

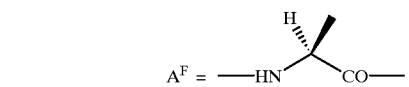

CYCLIC THIOETHER REACTION SCHEME 1

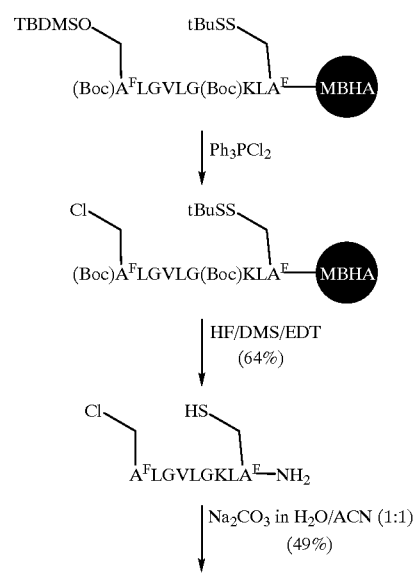

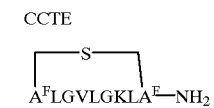

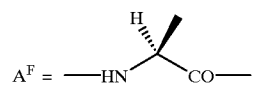

Alternatively, thioether analogs are prepared according to the reaction scheme below.

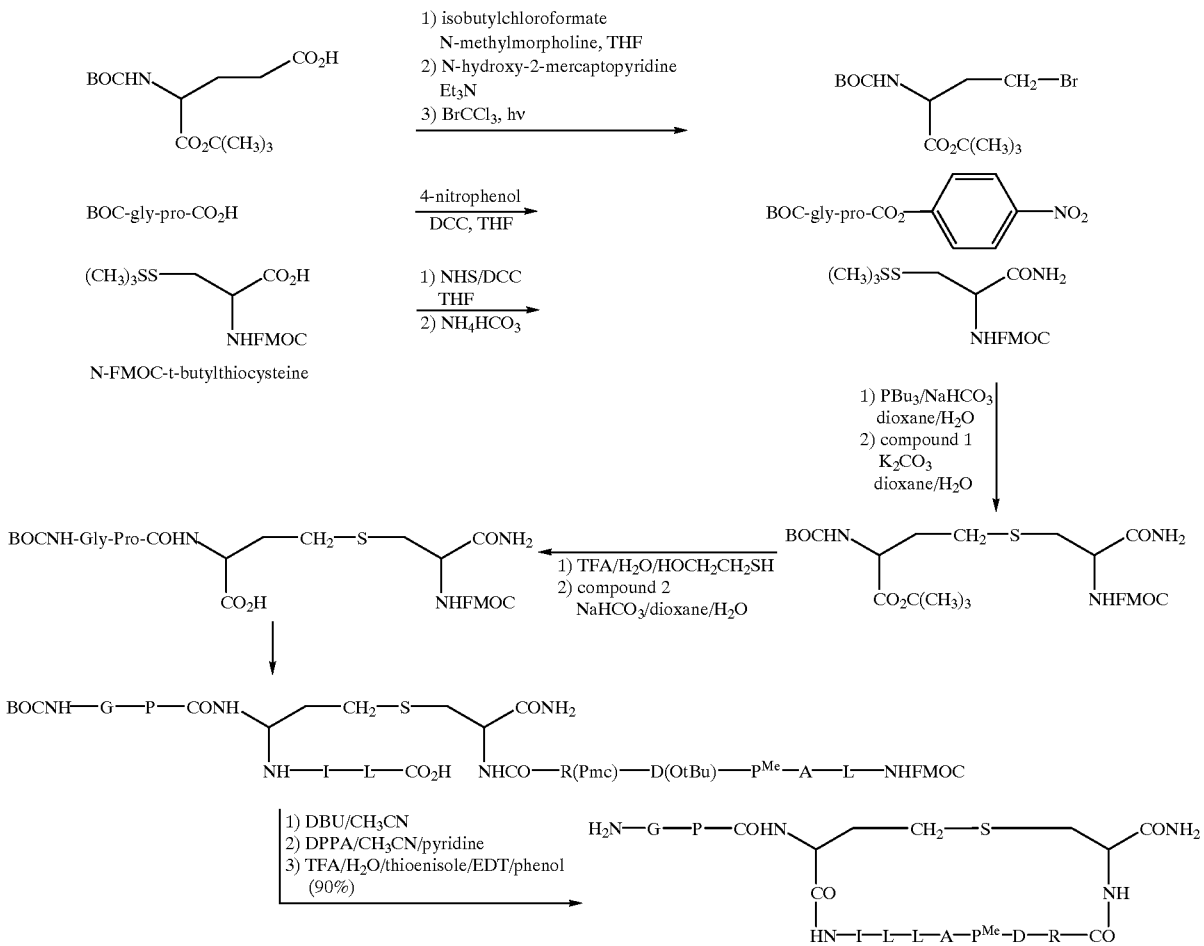

The following analogs are representative as analogs made according to cyclic thioether reaction scheme 2.

CTE A
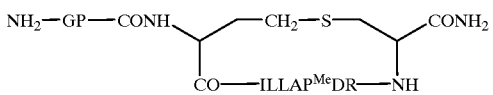

CTE B
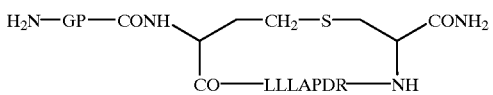

CTE C
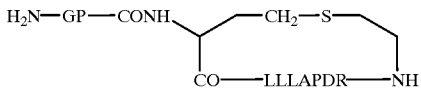

CTE D
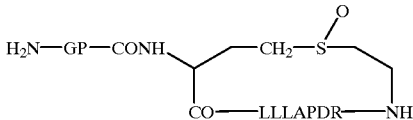

CTE E
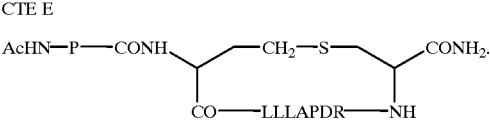

Exemplary cyclic thioether analogs were tested for activity against ACA antibodies ACA6501 and ACA6701. The results are shown in Table 8 below.

TABLE 8

| | IC50 Values ($\mu$g/0.1 mL) | |
|---|---|---|
| Thioether | ACA6501 | ACA6701 |
| CCTE, LJP 698 | 11.0 | 5.0 |
| HCTE, LJP 699 | 4.6 | 3.0 |
| CHTE, LJP 702 | 9.2 | 3.2 |
| HHTE, LJP 703 | 8.0 | 3.6 |
| LJP 690 | 10.0 | 4.0 |
| CTE A | 0.08 | |
| CTE B | 0.5 | |
| CTE C | 0.9 | |
| CTE D | 3.2 | |
| CTE E | 6.3 | |

The HCTE analog, LJP 699, outperformed the reference peptide, LJP 690, which is the truncated version, CLGVLGKLC (SEQ ID NO:65), of LJP 688, AGPCLGVLGKLCPG (SEQ ID NO:60).

All articles, patents and patent applications cited herein are incorporated by reference herein in their entirety. The following examples are intended to further illustrate the invention and its uniqueness. These examples are not intended to limit the scope of the invention in any manner.

EXAMPLES

Example 1

Measurement of Anticardiolipin Antibodies (ACA) in Serum 6501

Even numbered wells of an Immulon I microtitration plate (Dynatech Laboratories, Inc., Chantilly, Va.) were coated with 50 µg cardiolipin (Sigma Chemical, St. Louis, Mo.) in 30 µL ethanol per well. The plate was dried overnight at 4° C. and blocked with 200 µL of 10% adult bovine serum (ABS) (Irvine Scientific Co., Santa Ana, Calif.) in phosphate-buffered saline (ABS/PBS) for 2 hours at room temperature (RT). The plates were washed 5 times with Tris-buffered saline (TBS) prior to the addition of 10 µL of aPL standards and the test serum, ACA-6501. The aPL standards (APL Diagnostics, Inc., Louisville, Ky.) were reconstituted according to the manufacturer's instructions and diluted 1:50 with 10% ABS-PBS. The test serum, ACA-6501, diluted 1:50 to 1:2,000 in serial dilutions with 10% ABS-PBS, was added to selected duplicate wells and incubated for 2 hours at RT. The plate was washed five times with TBS and 100 µL of 1:1,000 goat-anti-human-IgG/alkaline phosphatase conjugate (Zymed, South San Francisco, Calif., Cat. No. 62,8422), in 10% ABS-PBS was added and incubated for 1 hour at RT. Again, the plate was washed five times with TBS and the assay was developed by adding 100 µL phenolphthalein monophosphate (PPMP) substrate solution (Sigma, Cat. No. P-5758), prepared from a stock solution of 0.13 M PPMP and 7.8 M 2-amino-2-methyl-1-propanol, adjusted to pH 10.15 with HCl, after a dilution of 1:26 with deionized water. After approximately 30 minutes, the reaction was stopped with 50 µL of 0.2 M dibasic sodium phosphate (Mallinckrodt, Analytical Reagent) added per well. The optical density was read at 550 nm in a microplate autoreader (Bio-Tek Instruments, Winooski, Vt., Model EL311). The optical density of the odd-numbered control wells (blank, without cardiolipin (CL)) was subtracted from the optical density of the even-numbered wells. The absorbance readings of the aPL standards were plotted using Graph Pad Prizm (Graph Pad Software, Inc., San Diego, Calif.) to generate the GPL (IgG phospholipid) standard curve. The diluted 6501 test serum absorbance readings were used to calculate GPL scores based on the GPL standard curve.

Example 2

Anticardiolipin Antibody (ACA) Purification from Serum 6501

In a 25 mL round-bottom flask (Kontes Scientific Co., Vineland, N.J.) a mixture of 1.2 mL cardiolipin (Sigma Chemical, St. Louis, Mo., #C-1649), 0.464 mL cholesterol (Sigma Diag., St. Louis, Mo., #965–25), 0.088 mL of 5 mg dicetylphosphate (Sigma Chemical, St. Louis, Mo., D-2631) per mL chloroform was dried for approximately 5 minutes in a Rotavap (Buchi, Switzerland). Following the removal of solvent, 2 mL of 0.96% (wt./vol.) NaCl (J. T. Baker, Inc., Phillipsburg, N.J.) Baker analyzed reagent) was added and mixed in a Vortex Genie Mixer (Scientific Industries, Inc., Bohemia, N.Y.) for 1 minute. The liposome suspension was incubated for 1 hour at 37° C. Meanwhile, serum 6501 was spun at 600×g in a Sorvall RT 6000 centrifuge (Dupont Co. Wilmington, Del.) for 10 minutes at 8° C. Four mL of the supernatant was placed in a 25 mL round-bottom flask with 1 mL of the prepared liposome suspension and the mixture was incubated with agitation at medium speed in an orbital shaker, Tektator V (Scientific Products, McGraw Park, Ill.) for 48 hours at 4° C., and an additional 2 hours at 37° C. Twenty mL of cold TBS was added and the mixture was transferred into a 50 mL polycarbonate centrifuge tube (Nalge Co., Rochester, N.Y.) and centrifuged at 27,000×g for 15 minutes at 4° C. in an RC3 centrifuge in a SS-34 rotor (Sorvall-Dupont, Wilmington, Del.). The precipitate was washed 3 times with 25 mL of cold 0.96% NaCl using the RC3 centrifuge. The pellet was dissolved in 1 mL of 2% (wt/vol) solution of n-octyl-β-D-glucopyranoside (Calbiochem, La Jolla, Calif.) in TBS and applied to a 0.6 mL protein A/cross-linked agarose (Repligen Corporation, Cambridge, Mass.) column which had been pre-washed with 15 times bed volume of 1 M acetic acid and equilibrated with 15 times bed volumes of TBS. The antibody-protein A/agarose column was washed with 40 times bed volume of 2% octylglucopyranoside to remove lipids, followed by extensive washings with TBS until the optical density of the eluate at 280 nm approached the baseline. The bound antibody was eluted with 1 M acetic acid. One mL fractions were collected, neutralized immediately with 0.34 mL 3 M Tris (Bio-Rad, electrophoresis grade reagent) per fraction and kept in an ice bath. The optical density of each fraction was determined at 280 nm in a spectrophotometer (Hewlett-Packard, 8452A Diode Array Spectrophotometer, Palo Alto, Calif.). Fractions containing antibody were pooled, concentrated and washed 4 times with TBS in Centricon-30 concentrators (Amicon Division, W.R. Grace & Co., Beverly, Mass.) per manufacturer's protocol. The final yield of purified antibody from 4 mL of serum 6501 was determined by reading the optical density at 280 nm of an aliquot from the concentration, where 1 mg=1.34 $OD_{280}$. The average yield obtained was 750 µg antibody from 4 mL of serum 6501. The purified antibody was tested for ACA activity and checked for purity with Laemmli SDS-PAGE.

Example 3

Construction of a p-III Library Vector Preparation fUSE 5 (Scott, J. K. and G. Smith, supra) was used as the vector for the construction of p-III libraries, and a variation of the method of Holmes, D. S. and M. Quigley (1981), Anal. Biochem. 144:193) was employed to generate the double-stranded replicative form (RF). Briefly, an 800 mL culture of E. coli K802, harboring fUSE 5, was grown in 2YT medium (Difco Labs, Ann Arbor, Mich.) containing 20 micrograms/mL tetracycline for 18 hours at 37 degrees with vigorous shaking. Cells were collected by centrifugation and resuspended in 75 mL STET. STET consists of 8% sucrose in 50 mM Tris/HCl pH 8.0, 50 mM EDTA and contains 0.5% Triton X-100. Lysozyme, 10 mg/mL in STET, was added to a final concentration or 1 mg/mL. After 5 minutes at RT, three equal aliquots were placed in a boiling water bath with occasional shaking for 3.5 minutes. The viscous slurry was centrifuged for 30 minutes at 18000×G and an equal volume of isopropanol was added to the supernatant. The solution was cooled to −20° C. and the nucleic acids were collected by centrifugation. The RF was isolated from a CsCl gradient as described by Sambrook et al. MOLECULAR CLONING: A LABORATORY MANUAL (Cold Spring Harbor Laboratory Press, Cold Spring Harbor, N.Y., 2d ed., 1989).

Preparation of the Random Insert

The DNA for insertion was generated by the "gapped duplex" method described by Cwirla et al. (1990) *Proc. Natl. Acad Sci. USA* 87:6378–6382. In this method, an oligonucleotide containing a degenerate region in the middle is surrounded by short constant regions on each end of the oligonucleotide. Two shorter, complementary oligonucleotides are annealed to form a "gapped duplex" possessing overhangs that are complementary to the sticky ends produced by the restriction endonuclease used to digest the vector. In this case, the longer degenerate oligonucleotide has the sequence: 5' GGGCTGGACCC(NNK)$_x$CCGGGGGCTGCTG 3' (SEQ ID NO:209) where N=A or C or G or T, K=G or T, and x is the number of codons in the random regions. EpiGS2 was designed to base pair to the 5' end of the degenerate oligonucleotide and has the sequence 5' GGGTCCAGCCCCGT 3' (SEQ ID NO:210). Similarly EpiGS3 was designed to anneal to the 3' end of the degenerate oligonucleotide and has the sequence 5' CAGCCCCCGG 3' (SEQ ID NO:211). When correctly annealed, the three oligonucleotides form a "gapped duplex" which, when inserted into fUSE 5 digested with Sfi1, restores the reading frame of p-III with the random insert near the 5' end.

Oligonucleotides described above were prepared by excision from polyacrylamide gels. One nanomole of EpiGS2, EpiGS3, and 50 picomoles of the degenerate oligonucleotide were kinased separately in 66 microliter volumes. The three oligonucleotides were then pooled, NaCl was added to 50 mM and the mixture was heated to 65° C. for 5 minutes followed by slow cooling to RT. The annealed oligonucleotides were then cooled on ice and used immediately in the ligation reaction with fUSE 5. The ligation reaction consisted of 10 micrograms of fUSE 5 DNA digested to completion with Sfi1, 30 μL of the "gapped duplex" solution and 1000 U of T4 ligase in a total volume of 450 microliters. The ligation was incubated for 18 hours at 16° C. The mixture was then phenol-chloroform extracted, precipitated with ethanol and the precipitate dissolved in 20 μL of water.

Generating and Amplifying the Library

The ligated DNA was introduced into *E. coli* by electroporation (Dower et al. (1988) *Nucleic Acid Res.* 16:6127–6145). Frozen electrocompetent MC1061 cells (0.1 mL) were mixed with 4 μL of ligated DNA in a cold 2 mm cuvette and subjected to 2.5 kV, 5.2 mS pulse by a BTX electroporation device (BTX Corp., San Diego, Calif.). Immediately after the pulse, 1 mL of SOC, a cell growth medium (see Dower et al., supra) was added. Five separate electroporations were carried out, pooled, and incubated at 37° C. for 1 hour. At that time, samples were removed and diluted to determine the total number of clones generated. The balance of the mixture was diluted in 1L of 2YT (1.6% Peptone, 140, 1% Yeast Extract, and 0.5% NaCl, Difco Labs, Ann Arbor, Mich.) containing 20 micrograms per mL of tetracycline and grown for 18 hours at 37° C. while shaken at 275 rpm. Phage were purified by 2 rounds of PEG/NaCl precipitation and resuspension in 1.2 mL TBS containing 0.02% sodium azide. Particle number was estimated by absorbance at 269 nm. The titer of the phage was determined by mixing 10 μL of dilutions of phage with 10 microliters of starved *E. coli*.

Example 4

Screening a p-III Library with aPL Antibody

Affinity-purified ACA-6501 (affACA-6501, 10 μg; 7 μl of 1.44 mg/mL stock solution) was incubated for 2 hours at RT in siliconized 1.4 mL microfuge polypropylene tubes with pooled phage from the x, y and z libraries (epi$^{xyz}$) [11 μL+8.5 μL+2 μL, respectively; total volume=21.5 μL,~$10^{10}$ clones] in a final volume of 100 μL TBS, pH 7.4, with 0.5% bovine serum albumin (BSA). During this incubation, the final steps in preparing freshly starved *E. coli*, strain K-91, were carried out. A suspension of *E. coli* freshly grown in 2YT medium for about 5 hours with 250 rpm shaking at 37° C. was spun at 1000×g for 10 minutes at RT in 50 mL polypropylene tubes. Twenty mL of 80 mM NaCl was added to the packed *E. coli* pellet and then incubated for 45 minutes at 37° C. at 100 rpm. Following centrifugation as above, the starved *E. coli* pellet was suspended in 1 mL of 50 mM ammonium phosphate/80 mM NaCl and used later for phage amplification. Protein G-agarose beads were washed 2× in TBS/BSA and 2 times in TBS/0.5% Tween-20 and stored at 4° C. as a 50% suspension in TBS/Tween.

Two hundred μL of the protein G-agarose bead suspension was then added to the ACA-6501/phage mixture and incubation continued for an additional 1 hour at RT. At this point, the mixture was chilled and washed 3 times with cold TBS/Tween and the precipitate was collected in a microfuge in a cold room. The washed beads were transferred to new microfuge tubes prewashed with TBS/BSA and TBS/Tween to prevent non-specific adherence. After three additional washes with TBS/Tween, the beads with bound ACA-6501-bearing phage were eluted with 300 μL 0.2 N HCl/glycine, pH 2.1 by tumbling for 10 minutes at RT. Following centrifugation at 16,000×g, the acidic eluate supernatant was collected and an additional 100 μL of elution solution was added to the bead pellet and the procedure repeated. After 10 minutes, the phage-containing eluates (representing the unamplified first round phage) were pooled (~400 μL) and placed in a sterile 17×100 mm polypropylene cell culture tube to which was added 50 μL 0.5 M NaCl followed by pH neutralization with 2.5 M Tris base (usually ~25–35 μL). An equal volume of the starved *E. coli* suspension was added immediately and then incubated for 10 minutes at 37° C. at 100 rpm. The mixture was then transferred to a 250 mL sterile culture flask containing 25 mL 2YT with 20 μg/mL tetracycline (Tet) and incubated overnight at 37° C. at 250 rpm.

To isolate amplified phage from overnight cultures, the suspension was centrifuged at 12,000×g for 10 minutes in polycarbonate tubes and the pellet discarded. After heating the supernatant at 70° C. for 30 minutes in polypropylene tubes, the material was spun again in polycarbonate tubes and the supernatant saved. To the supernatant, ¼ volume of 20% (w/v) polyethylene glycol, molecular weight 8000 (PEG 8000) was added to precipitate phage. The solution was mixed by inversion 100 times and then incubated at 4° C. for 2 hours. After centrifugation at 35,000×g for 30 minutes at 4° C., the phage-containing pellet was resuspended in ~0.5 mL of TBS/BSA and transferred to a 1.4 mL microfuge tube. After a 1 minute spin in a microfuge at 16,000×g, the supernatant was transferred to a clean tube and labeled first round amplified phage.

During second, third and fourth rounds of biopanning, 75 μL of amplified phage from the preceding round was incubated with 7 μL affACA-6501 in a final volume of 100 μL. For fifth round phage, affACA-6501 was diluted first at 1:1000, then treated as described for the other rounds. All subsequent steps were carried out as described for the first round. Phage from five rounds of biopanning were spot-titered on 2YT/Tet plates to determine phage concentration. The spot titer of amplified phage requires an initial phage dilution of 1×$10^6$ in TBS/BSA or 2YT media. For each round, 10 µL of the dilute phage was incubated with 40 µL of starved *E. coli* for 10 minutes at 37° C. with no shaking. Following the addition of 950 µL of 2YT/dilute Tet (0.2 µg/mL), the mixture was incubated for 30–45 minutes at 37° C. with 250 rpm shaking. Ten µL aliquots of neat and diluted phage solutions, 1:10, 1:100, and 1:1000, were spotted in 2YT/dilute Tet using agar plates containing 20 µg/mL Tet.

Micropanning

Immulon type 2 plates were coated with protein G. Protein G was prepared at 10 µg/mL in 0.1 M $NaHCO_3$ and 100 µL per well was added to the wells of microtitration plates and incubated overnight at 4° C. After discarding excess protein G solution from plates, each well was blocked with 250–300 µL 2YT for 1 hour at RT with agitation on an oscillating platform. Tris-buffered saline, pH 7.4/0.5% Tween 20 (TBS/Tween), was used with an automatic plate washer to wash the wells 4 times with 200 µL. One hundred µL affACA-6501 (or control normal IgG), diluted to 2.5 µg/mL with 2YT, was added to washed wells. The plate was transferred to a cold room rotator near the end of a 1 hour incubation at RT on a rotating platform.

Phage to be tested by micropanning were obtained from the agar plates generated by biopanning. Each clone to be tested was transferred using sterile toothpicks to a separate well of a round-bottom 96-well microtitration plate (Corning, Corning, N.Y.) containing 250 µL 2YT/Tet per well and cultured overnight at 37° C. Clone designations are based on the screening antibody, the biopanning round of origin, and the location of the clone in the overnight culture plate, e.g., ACA-6501/3B10 refers to the clone isolated by ACA-6501 in the third round located in the well designated B10 on the microtitration plate. Following overnight incubation, phage cultures were centrifuged using a microtitration plate holder at 1300×g for 10 minutes at RT. Supernatants constituted the source of "neat" phage.

Figure 8:
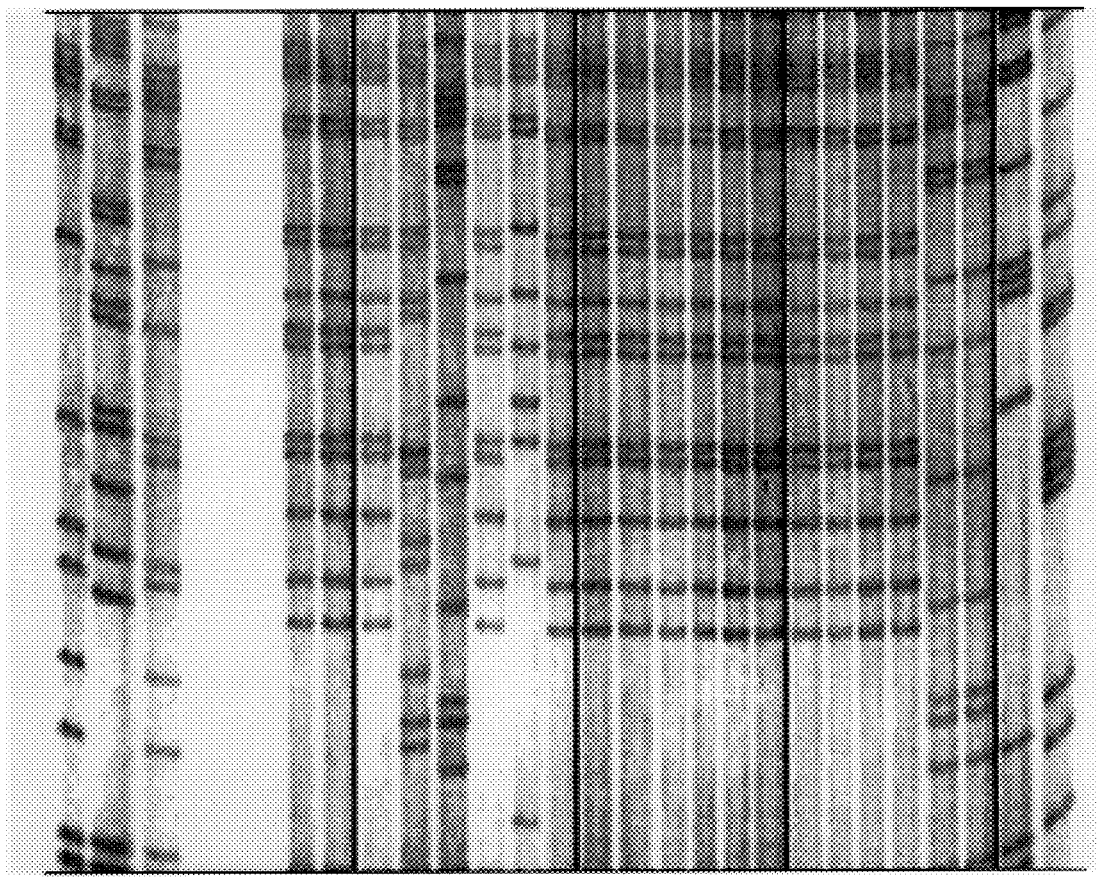
FIG. 8 illustrates the dramatic drop in sequence diversity of the isolated clones by the fourth round of biopanning.

Initial micropanning was restricted to six clones which were tested at dilutions expanded by factors from 1:10 to $1:10^6$. The results from these pilot clones were used to suggest the appropriate single dilution that would yield gradable results for clones in the source plate for each round. Plates representing cultured, randomly chosen clones from the 3rd, 4th, and 5th rounds of biopanning were diluted to 1:100,000 from the "neat" solution using 2YT in microtitration plates with a final volume per well of 250 µL. From the last plate representing the desired dilution, 100 µL was added to the plate containing protein G-bound ACA-6501 and normal IgG prepared as described above. The incubation of dilute phage with aPL antibody or control IgG was carried out for 2 hours at 4° C. on a flat rotator. After 9 washes with TBS/Tween in an automated plate washer, the IgG-bound phage was eluted with 20 µL of 0.2 N HCl-glycine/0.1% BSA, pH 2.2. The elution incubation continued for 10 minutes at RT, during which time a new Corning microtitration plate was prepared containing 20 µL of freshly starved *E. coli* per well and kept chilled. One hundred forty µL of 29 mM Tris was added to the plate containing the phage eluates in order to neutralize the pH, following which 20 µL of phage suspension was transferred from each well to the corresponding well in the plate containing starved *E. coli*. After a 10 minute incubation at 37° C., 200 µL 2YT/dil Tet was added and incubation carried out an additional 30 minutes at 37° C. Using multichannel pipettors, 10 µL from each well was spotted on a large 2YT/Tet agar plate while retaining the original 8×12 well pattern and orientation from the last microtitration plate. After allowing the spots to dry for 30 minutes, the plate was incubated overnight at 37° C. The following day, colonies were semiquantitatively scored from 0 to 4+, with 0 symbolizing <10 colonies; +/−, 10–20; 1+, 20–50; 2+, 50–70% confluent; 3+, 70–90% confluent; and 4+ representing >90% confluent colonies. Of the 94 clones that were examined at a dilution of $1:10^5$ [representing 81 third, 6 fourth, and 7 fifth round clones], six clones had micropanning scores of zero, three scored 1+, 14 scored 2+, 62 scored 3+, and 9 scored 4+. A survey of random clones from the plates representing the second through fifth rounds of biopanning was carried out by G-track DNA sequencing as described below. The results showed a dramatic drop in sequence diversity by the fourth round of biopanning (see FIG. 8), therefore, a second plate was micropanned using phage at a dilution of $1:3\times10^5$, this time including clones from an earlier (second) round. A total of 94 clones were tested, including 29 which had scored high at $1\times10^5$ dilution [26 from the 3rd round, 1 from the 4th found, and 2 from the 5th round] plus 65 clones from the 2nd round that had not been previously tested. Of the 94 clones tested at a dilution of $1:3\times10^5$, 26 scored zero, 11 scored +/−, 10 scored 1+, 13 scored 2+, 34 scored 3+, and zero scored 4+.

G-track DNA Sequencing

Single-stranded viral DNA was isolated from cultures incubated overnight at 37° C. To prepare cultures, 2YT/Tet, either as 2 mL in tubes or 250 µL in microtitration plate round-bottom wells, was inoculated with individual phage from spread plates of previously grown cultures in microtitration plates. The purification of phage by 20% PEG/2.5 M NaCl precipitation of culture supernatants as well as the isolation or release of virion DNA by phenol-chloroform extraction or by alkali denaturation was performed as described in Smith, G. P. and J. K. Scott, "Libraries of peptides and proteins displayed on filamentous phage" (1993) *Meth. Enzymol.* 217:228–257 for cultures in tubes and as described in Haas, S. J. and G. P. Smith G. P., "Rapid sequencing of viral DNA from filamentous phage" (1993) *BioTechniques* 15:422–431 for phage in microtitration plates. The dideoxy nucleotide chain termination DNA sequencing technique of Sanger et al. (Sanger et al., "DNA sequencing with chain terminating inhibitors" (1970) *Proc. Natl. Acad. Sci.* 74:5463–5467) was carried out using a commercial Sequenase kit (U.S. Biochemical/Amersham, Arlington Heights, Ill.) as described by Smith and Scott, supra, for tube culture phage DNA and as in Haas and Smith, supra, for phage DNA from microtitration plates. By using only the ddCTP termination mixture, G tracking or the sequence pattern suggested by a single base (G) was obtained following electrophoresis on 7% polyacrylamide/urea sequencing gels and exposure by autoradiography. Standard gel electrophoresis and autoradiography procedures were followed (Sambrook et al., supra).

G-tracking of 76 clones from the micropanning plate tested at a phage dilution of $1:1\times10^5$ from the ACA-6501 library screen revealed 11 unique sequences, while 64 clones from the second micropanning plate tested at a phage dilution of $1:3\times10^5$ showed 30 unique sequences. Conventional DNA sequencing using all four dideoxynucleotide triphosphates was applied to the phage clones with the highest micropanning scores and unique sequences and resulted in the 12 sequences shown in Table 1 for the xyz library.

Phage-Capture ELISA

Figure 9:
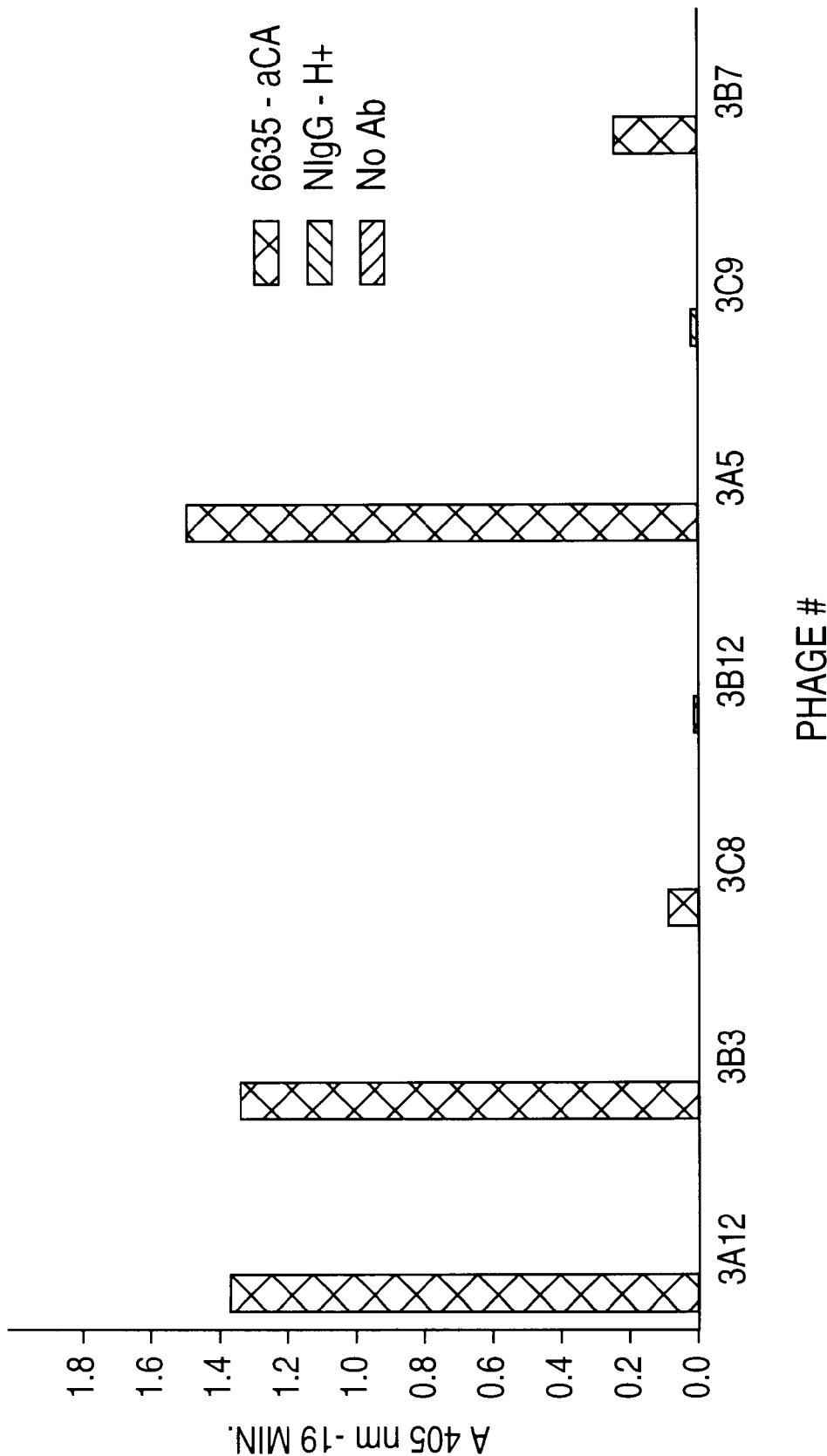
FIG. 9 illustrates that three clones (3A12, 3B3 and 3A5) exhibited a very strong immunospecific signal in the phage-capture ELISA using ACA-6635 whereas all clones tested were unreactive with normal IgG.

Clones ACA-6635/3A12, 3B3, 3C8, 3A5, 3C9, and 3B7 were grown as 3 mL cultures. Affinity purified ACA-6635 was diluted to 2.5 µg/mL in phosphate-buffered saline, pH 7.2, and 100 µL added to Immulon-2 microtitration plate wells. After 2 hours, the plates were washed 3 times with TBS/Tween in an automated plate washer with no shaking. The plate was then blocked with 150 μL 0.1% BSA (globulin-free) in PBS per well. After 1 hour at 4° C., the plate was washed 3 times as previously described. After centrifuging each phage culture 3 minutes at 17,000×g, each supernatant was diluted 1:10 in 0.1% BSA/PBS and 100 μL added to each of the wells coated with affinity purified ACA-6635 and then incubated for 2 hours at 4° C. Plates were then washed with TBS/Tween as before. Horseradish peroxidase-conjugated sheep IgG anti-M13 phage antibody (Pharmacia, Inc., Piscataway, N.J.) was diluted 1:5,000 in 0.1% BSA/PBS and 100 μL applied to each well. Following incubation for 1 hour at 4° C., the plate was washed 4 times as before. One hundred μL of substrate prepared according to the conjugate manufacturer's instructions was added to each well. After 19 minutes, the absorbance at 405 nm of each well was read in the automated microplate absorbance reader (Biotek, Winooski, Vt.) The seven clones tested from the ACA-6635 phage library screen were selected because of their high micropanning scores and negative phage-ELISA scores (see below). As shown in FIG. 9, three clones (3A12, 3B3, and 3A5) out of the seven tested exhibited a very strong immunospecific signal in the phage-capture ELISA.

Phage-ELISA

Figure 10:
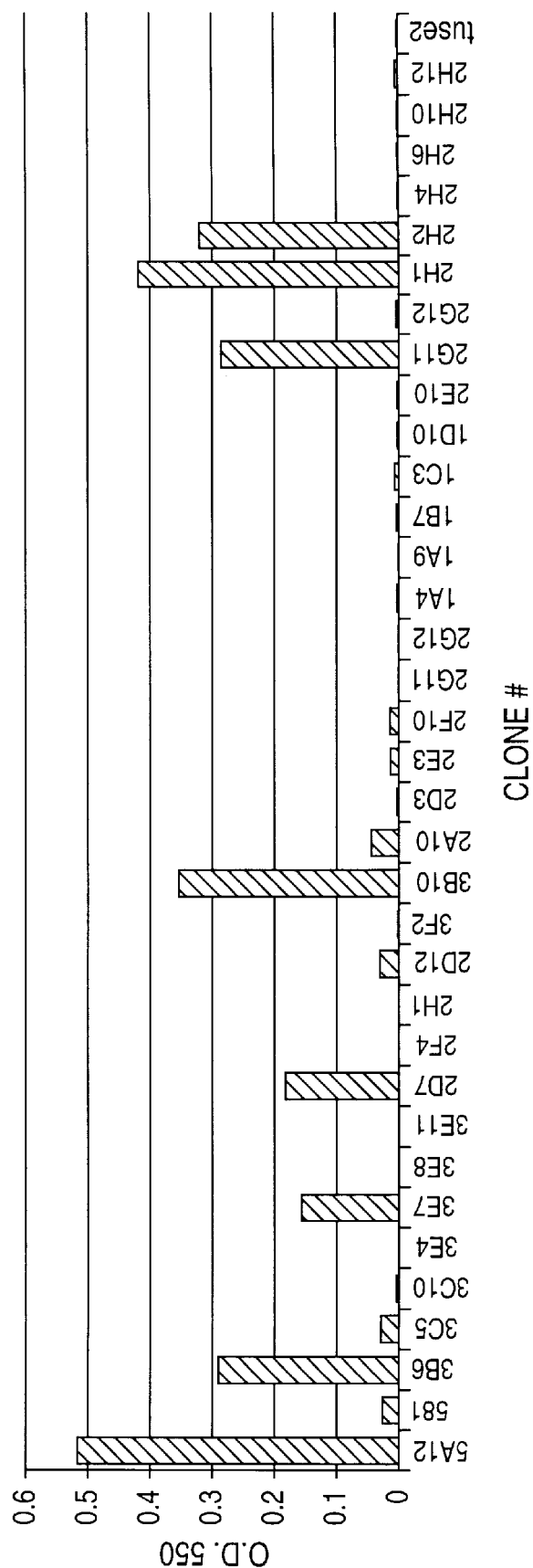
FIG. 10 shows the strong signal exhibited by seven clones in a phage-ELISA using ACA-6501.

Three mL cultures were prepared from 35 clones previously isolated with affinity purified ACA-6501 in several phage library screens as well as one fUSE 2 phage clone lacking a peptide insert which was used as a control. After centrifugation for 3 minutes at 17,000×g, 100 μL from each phage supernatant (adjusted to ~2×10$^{11}$ particles/mL, based on absorbance) was added to microtitration plate wells (Falcon, Becton-Dickinson Labware, Lincoln Park, N.Y.) and allowed to incubate overnight at 4° C. Following four washes with TBS 7.4, the plate was blocked with 125 μL of 0.5% BSA/TBS for 1 hour at RT. After another four TBS washes, 100 μL of affACA-6501 previously diluted to 2.5 μg/mL in TBS/BSA was added to each well and allowed to incubate 1 hour at 37° C. Following an additional four washes, 100 μL anti-human IgG diluted 1:1000 in TBS/0.5% Tween was added to each well. After 1 hour at RT, enzyme substrate was added and the incubation allowed to proceed for 2 hours. Following the addition of 50 μL 0.2 M Na$_2$HPO$_4$ to stop the reaction, absorbance was measured at 550 nm in the automated plate absorbance reader. As shown in FIG. 10, seven of the clones had significant signals in the phage-ELISA with ACA-6501: 5A12, 3B6, 3E7, 3B10 (same sequence as 2D7), 2G11, 2H1, and 2H2. The sequences for these clones are shown in Table 2.

Peptide-ELISA

In the standard protocol, stock solutions of tetrameric peptide in dimethylformamide were diluted 1000 times to 10 μg/mL in pH 9.5 carbonate buffer. Each microtitration plate well was coated overnight at 4° C. with 100 μL of dilute peptide followed by blocking with buffered albumin. Peptide-coated microtitration plates were incubated 1–2 hours at room temperature with aPL sera at several dilutions starting at 1:50. Following washes, the presence of peptide-bound human IgG was determined with enzyme-conjugated anti-human IgG according to standard ELISA procedures.

Competitive Binding Peptide-ELISA (A) Each well of an Immulon II plate (Dynatech Laboratories, Inc., Chantilly Va.) was coated with 100 μL of a solution containing 10 μg tetravalent peptide ACA 6501/3B10 in 50 mM sodium carbonate, pH 9.5, containing 35 mM sodium bicarbonate (Fisher Scientific, Pittsburgh, Pa., reagent grade) for at least 1 hour at RT, except for three wells used as blank controls. The liquid was then removed from the wells and 200 μL of 0.5% (wt/vol) BSA (Sigma Chemical, St. Louis, Mo., #A7638) in TBS was added per well including the blank wells for blocking and incubated for at least 1 hour at RT. Four 1.5 mL microfuge tubes were numbered 1 to 4. The following reagents were mixed in the first microfuge tube (Brinkman Instruments, Westbury, N.Y.): 30 μL of 5% BSA; 284 μL TBS; 8 μL of a stock solution of approximately 400–500 μg/mL of monomeric peptide (ACA-5A12 or -CB2 or -3B10 or scrambled -3B10 as negative control) in TBS; and 8.2 μL of 1:10 diluted serum 6501 in 0.5% BSA-TBS. The following reagents were mixed in the second microfuge tube: 30 μL of 5% BSA; 290 μL TBS; 2 μL of a stock solution of approximately 400–500 μg/mL of monomeric peptide (ACA-5A12 or -CB2 or -3B10 or scrambled -3B10 as negative control) in TBS; and 8.2 μL of 1:10 diluted serum 6501 in 0.5% BSA-TBS. The following reagents were mixed in the third microfuge tube: 30 μL of 5% BSA, 287 μL of a 1:10 dilution of approximately 400–500 μg/mL of monomeric peptides (5A12, CB2, 3B10, or scrambled sequence 3B10 control), and 8.2 μL of ACA-6501 serum previously diluted 1:10 in 0.5% BSA-TBS. The following reagents were mixed in the fourth Eppendorf microfuge tube: 60 μL 5% BSA; 584 μL TBS and 16.5 μL of 1:10 diluted serum 6501 in 0.5% BSA-TBS. The blocked plate was washed 5 times with TBS. The solution in the first microfuge tube was added to triplicate wells, 100 μL per well. Identical amounts of the solutions in the second, third and fourth microfuge tubes were also added to triplicate wells. An aliquot of 100 μL of the solution in the fourth microflige tube was added to each of the three blocked blank wells of the microtitration plate. The plate was incubated for 1 hour at RT with agitation at 40 rpm in an orbital shaker (American Dade, Miami, Fla., Rotator V) and then washed 5 times with TBS. An aliquot of 100 μL of 1:1000 diluted goat-anti-human-IgG/alkaline phosphatase conjugate (Zymed, South San Francisco, Calif., Cat. no. 62-8422) in 0.5% BSA-TBS was added and incubated for 1 hour at RT. The plate was then washed 5 times with TBS and the assay was developed by adding 100 μL PPMP diluted substrate solution as described in Example 1. After 20 minutes, the reaction was stopped by adding 50 μL of 0.2 M Na$_2$HPO$_4$ (Mallinckrodt, St. Louis, Mo., reagent grade) per well. The optical density was read at 550 nm in a microplate reader (Bio-Tek Instruments, Winooski, Vt., Model EL 311). The optical density at 550 nm versus the amount of the peptide per well was plotted in Graph Pad Prizm (Graph Pad Software, Inc., San Diego, Calif.). The amount of peptide required for 50% inhibition of binding of serum 6501 to tetravalent 3B10 was calculated from the graph.

(B) Immulon I® 96-well, flat-bottom, polystyrene microtitration plates (Dynatech Laboratories, Inc., Chantilly, Va.) were coated with 30 μL/well of cardiolipin (CL, 50 μg; Sigma Chemical Co., St. Louis, Mo.) in ethanol. Two control wells received 30 μL ethanol only. After overnight evaporation at 4° C., each well was blocked with 200 μL of 5% (w/v) fish gelatin in PBS for 2 hours at RT. The CL-coated, blocked plate was washed 5 times with TBS and then to each well was added β2-GPI as 100 μL of 2.3% (v/v in PBS) IgG-depleted human serum (Sigma Chemical Co., St. Louis, Mo.) and incubated 2 hours at RT.

During this incubation, variable amounts of each of six peptides were mixed with 22 μL ACA6501 serum diluted with 3% fish gelatin in 1:1 TBS/PBS (final dilution of 1:400) in a final volume of 220 μL using Eppendorf microcentrifuge tubes. Specifically, in tube #1 were mixed 181.3 μL of 3% fish gelatin in TBS-PBS, 16.7 μL of peptide stock solution plus 22 μL of ACA6501 serum diluted 40 times in 3% fish gelatin/TBS-PBS. Stock solutions ranged from 450–800 µg/mL for peptides #951 (diserine non-cyclized negative control), #952 (a lot of LJP 690), and thioethers CCTE-3G3, CHTE-3G3, HCTE-3G3 and HHTE-3G3. To tube #2 the following were added: 148 µL fish gelatin/TBS-PBS, 50 µL of peptide stock solution, plus 22 µL of 40 times diluted ACA6501 serum. Tube #3 contained 48 µL fish gelatin/TBS-PBS, 50 µL of peptide stock solution, plus 22 µL of 40 times diluted ACA6501 serum. The control tube #4 received 396 µL fish gelatin/TBS-PBS and 44 µL of 40 times diluted ACA6501 serum (no peptide). Each of the tubes incubated for approximately 1 hour at RT.

Figure 12:
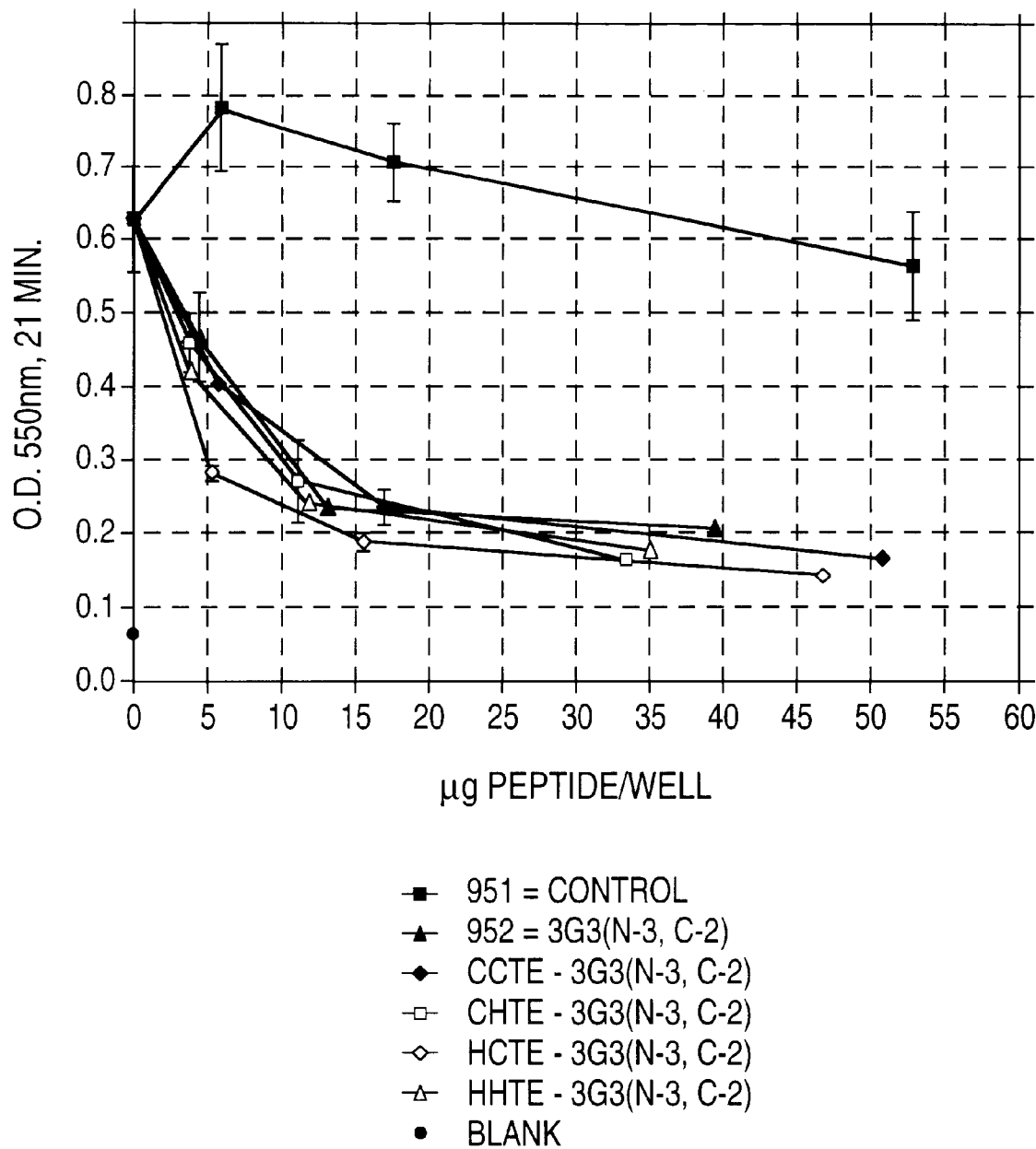
FIG. 12 illustrates the comparative activity of modified ACA6641/3G3 analogs.

The CL/β2-GPI microtitration plate was washed 5 times with TBS and 100 µL aliquots in duplicate from Eppendorf tubes #1, 2, 3, and 4 containing the antibody-peptide (or no peptide mixtures) were added to the wells. A volume of 100 µL from tube #4 was added to the duplicate control wells containing no cardiolipin. The microtitration plate was incubated for 1 hour at RT with agitation at 40 rpm in an orbital shaker (American Scientific, Rotator V), washed 5 times with TBS and then 100 µL of 1:1000 goat anti-human IgG alkaline phosphatase conjugate (Zymed, Cat No. 62-8422) in 0.5% (w/v) BSA-TBS was added. Following incubation for 1 hour at RT, the microtitration plate was again washed 5 times with TBS and the calorimetric enzyme detection developed by adding 100 µL of PMPP solution (7.8 g phenolphthalein monophosphate plus 69.5 g of 2-amino-2-methyl-1-propanol in 100 mL water stock solution diluted 1:26 with water). After 21 minutes, the reaction was stopped by adding 50 µL of 0.2 M $Na_2HPO_4$ (Mallinckrodt) to each well. Absorbance at 550 nm was read in a microplate reader (Bio-Tek Instruments, Model EL 311). Absorbance vs. peptide added was plotted on Graph Pad Prism (Graph Pad Software, Inc.) as shown in FIG. 12. The amount of peptide that inhibited ACA6501 binding by 50%, the $IC_{50}$, was calculated from the graph at the intersection of half-maximal absorbance with amount of peptide added.

Example 5

Truncation Experiments of Peptide 3B10 and the Resulting Peptide Competition ELISA Results Microtitration plates (96-well, flat bottom polystyrene, Immulon-2, Dynatech Laboratories, Inc., Chantilly, Va.) were coated with 100 µL/well for 1 hour at RT with tetrameric ACA-6501/3B10 peptide at 10 µg/ML in carbonate buffer, pH 9.6 (15 mM $Na_2CO_3$/35 mM $NaHCO_3$). After the liquid from the wells was removed, each well was blocked for 1 hour at RT with 200 µL 0.5% (wt/vol) BSA (globulin-free, cat. no. A7638, Sigma Chemical Co., St. Louis, Mo.) in TBS. Three wells on the plate were left uncoated by tetravalent peptide to serve as blank control wells.

During the blocking step, each soluble, monomer peptide to be tested was set up in three test tubes (Eppendorf micro test tubes, Brinkmann Instruments, Westbury, N.Y.) each containing 30 µL 5% BSA/TBS, 8.2 µL ACA-6501 serum (at 1:10 dilution with 0.5% BSA/TBS), plus a variable volume of the peptide/TBS stock and the necessary volume of TBS buffer to yield a final volume of 330 µL. The 330 µL volume was sufficient to generate triplicate 100 µL samples for each peptide concentration that was tested for its ability to block ACA-6501 binding to the tetravalent peptide-coated plate. For peptide 139, which was truncated at the amino terminus and lacks the framework ala-gly contribution normally tested, the concentration of the stock solution was approximately 340–400 µg/mL TBS and aliquots of 19 µL, 75 µL, and 292 µL were removed to prepare the three peptide concentration tubes. For peptide 142 (lacking only the N-terminal ala) and peptide 143 (not truncated), stock solution concentrations were 400–500 µg/mL in TBS. Aliquots from each stock solution of 1 µL, 4 µL, and 16 µL were removed to set up the three concentration tubes for each peptide. For the peptide monomer control tube (lacking peptide), a tube with a final volume of 660 µL was prepared containing 60 µL 5% BSA, 16.5 µL of a 1:10 dilution of ACA-6501 and 583.5 µL TBS, i.e., the same final concentrations (0.5% BSA and ACA-6501 serum at 1:400) as the 330 µL tubes but with twice the volume and without peptide.

Figure 11:
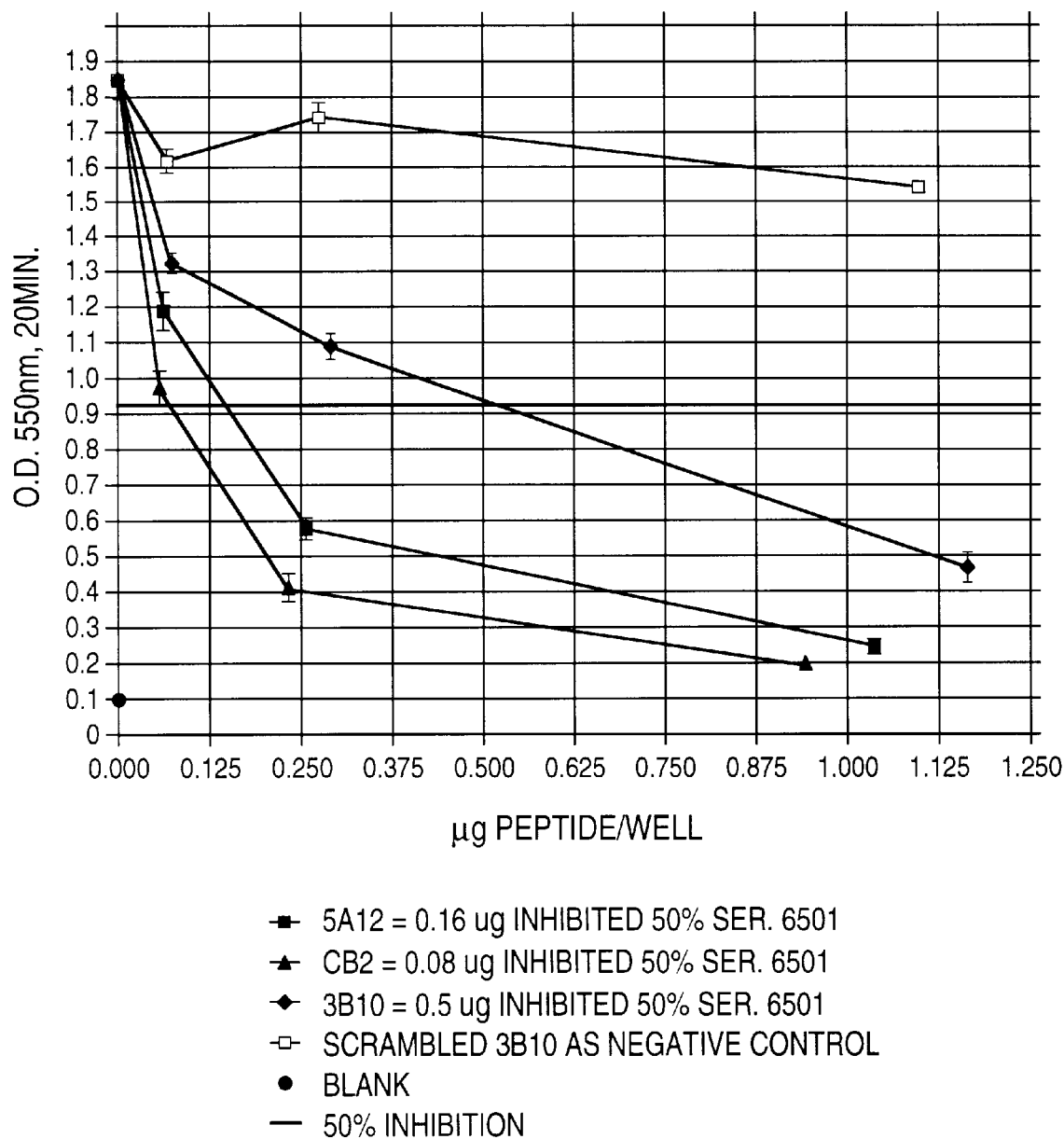
FIG. 11 shows the results of a competitive-binding ELISA obtained with peptides 5A12, CB2 and 3B10 using ACA-6501. 0.16 μg of Peptide 5A12 produced 50% inhibition of binding of ACA6501 aPL antibody to tetravalent peptide ACA6501/3B10 bound to polystyrene microplate wells, whereas 0.08 μg of CB2 and 0.5 μg of 3B10 were required to produce 50% inhibition.

Following the blocking incubation, the plate coated with tetravalent peptide was washed 5 times with TBS. From each 330 µL tube containing peptides 139, 142 and 143 at different concentrations, 100 µL was added to coated triplicate wells. Three 100 µL aliquots from the 660 µL control tube without peptide were each added to coated wells and three additional 100 µL aliquots were each added to uncoated blank wells. The plate was incubated at 40 rev/min on a rotary orbital shaker (Rotator V, American Dade, Miami, Fla.) for 1 hour at RT and then washed 5 times with TBS. One hundred µL/well of goat antihuman IgG/alkaline phosphatase conjugate (Cat. no. 62-8422, Zymed, South San Francisco, Calif.) diluted 1:1000 in BSA/TBS was added to the microplate. After incubation for 1 hour at RT, the plate again was washed 5 times with TBS. Color development followed the addition of 100 µL/well of freshly prepared dilute PPMP substrate solution. A dilute solution of PPMP (phenolphthalein monophosphate, cat. no. P-5758, Sigma Chemical Co., St. Louis, Mo.) was prepared by making a 1:26 dilution with water of the PPMP stock solution (0.13 M PPMP, 7.8 M amino-2-methyl-1-propanol adjusted to pH 10.15 with HCl). After 30 minutes, the reaction was stopped by adding 50 µL/well of 0.2M $Na_2HPO_3$ (reagent grade, Mallinckrodt, St. Louis, Mo.). Absorbance measurements at 550 nm were carried out on a microplate reader (Bio-Tek Instruments, Winooski, Vt.) and the $A_{550nm}$ vs. peptide added per well results plotted using Graph Pad Prizm (Graph Pad Software, Inc., San Diego, Calif.). As shown on FIG. 11, a horizontal line has been drawn corresponding to half-maximal the binding reaction obtained in the absence of monomer peptide competitive inhibition. The amount of peptide necessary for 50% inhibition can be read at the intersection of this line with the plot for each peptide tested. The 50% inhibition values are shown on FIG. 12. The results indicate that while the loss of the N-terminal Ala had no negative consequences, the additional loss of Gly increased by about 8-fold the concentration necessary to achieve 50% inhibition.

Example 6

Substitution of Alpha Methyl Proline into 3310 and the Resulting ELISAs

Testing of peptides ACA-6501/3B10 and analogs in which prolines at the 3 and 9 position were replaced by α-Me-Pro was carried out using the methodology described in Example 5. Peptides 3B10, 726 (αMe-Pro substituted at the 3 position), 727 (αMe-Pro substituted at the 9 position), and 728 (αEMe-Pro substituted at both the 3 and 9 positions) were tested as soluble monomer peptides in a competitive-binding ELISA using tetramer peptide 3B10-coated microtitration plates and ACA-6501 serum.

Microtitration plates were coated with tetramer 3B10 peptide as described for Example 5. For each of the four peptides tested, three peptide concentrations were prepared in tubes. As in Example 5, these twelve tubes had final concentrations of 0.5% BSA/TBS and ACA-6501 serum at a final dilution of 1:400 in a final volume of 330 µL. All peptide stock solutions were at 400–500 µg/mL TBS. To tubes containing 30 µL of 5% BSA/TBS and 8.2 µL of ACA-6501 serum (diluted 1:10 with 0.5% BSA/TBS), aliquots of 1 µL, 4 µL, or 16 µL of each of the four peptide stock solutions were added in addition to an appropriate volume of TBS to achieve a final volume of 330 µL. A control tube with no competitor peptide present was prepared with a final volume of 660 µL as described in Example 5.

Figure 13:
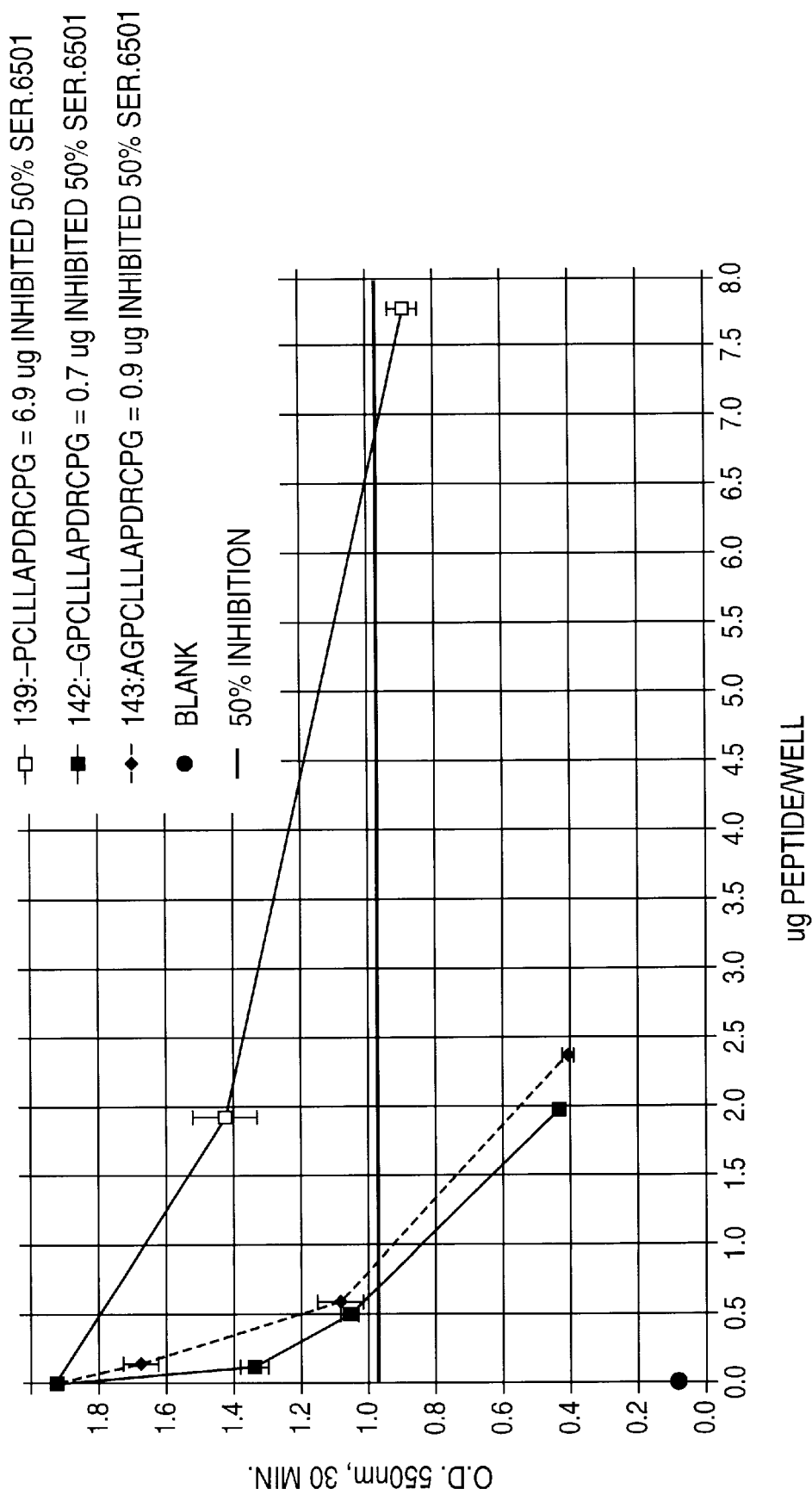
FIG. 13 (SEQ ID NO:1 through SEQ ID NO:3) illustrates that the 50% inhibition values for peptides 139, 142 and 143 in a competitive-binding ELISA using ACA-6501 aPL antibody were 6.9, 0.7 and 0.9 μg, respectively.

Following the blocking incubation of the tetravalent peptide-coated plate, three 100 µL aliquots from each of the peptide concentration tubes for each of the four peptides as well as the control tube containing no peptide and blank controls were tested as described in Example 5. The microtitration plate ELISA procedures as well as the data handling were performed as described in Example 5. As shown in FIG. 13, peptide 727, where α-Me-Pro was substituted at the 9 position, was significantly more active than unmodified peptide 3B10 or the analog with both prolines changed (peptide 728). Peptide 726, which was substituted at position 3, lost activity as a result of the substitution.

Example 7

Abbreviated Description of Screen with 6626 Antibody and the Corresponding Sequences Affinity purified ACA-6626 (AffACA-6626) was isolated by affinity purification from 8 mL of ACA-6626 plasma as previously described. AffACA-6626 (10 µg) was incubated with the epitope xy'z phage library consisting of a pool of all p-III component libraries in a final volume of 100 µL as previously described for ACA-6501 biopanning. Following three rounds of biopanning, randomly selected phage from the second and third rounds were tested by micropanning. Only a few clones were weakly immunopositive at a 1:1000 dilution. An additional 4th round of biopanning was carried out. Micropanning of 94 fourth round clones revealed 43 immunopositives, some at phage dilutions as high as 1:100,000. G-Tracking DNA sequencing of the 43 immunopositive clones carried out as previously described for ACA-6501 revealed 5 unique sequences. After conventional four base DNA sequencing, the translated amino acid sequences of Table 3 were obtained.

Example 8

Identification of Sequences Specific for the ACA from Patient 6644

The epi$^{x'y'z}$ phage display library was screened using methods similar to those in Example 4 with ACA affinity purified antibody from patient number 6644. A colony blot assay as described previously was employed as the final identification step prior to peptide synthesis. Approximately 150 colonies were plated on the original nitrocellulose membrane and assayed. Antibody from patient 6644 was used at a concentration of 1 µg/mL. Of the 150 colonies plated on the nitrocellular membrane and assayed, only 4 were strongly positive and 2 weakly positive in this screen. Sequencing of the inserts of the six positive phage selected by this screen revealed that the inserts were all derived from the 8-mer library with a free amino-termninus (epi$^z$):

Gly-Ile-Leu-Ala-Leu-Asp-Tyr-Val-Gly-Gly (SEQ ID NO:212) (3 inserts)

Gly-Ile Leu-Thr-Ile-Asp-Asn-Leu-Gly-Gly (SEQ ID NO:213) (1 insert)

Gly-Ile-Leu-Leu-Asn-Glu-Phe-Ala-Gly-Gly (SEQ ID NO:214) (2 inserts)

Example 9

Summary of Phage Library Screen with ACA-6641

AffACA-6641 was isolated from 4 mL of plasma taken from patient number 6641. AffACA-6641 (10 µg) was incubated with the pooled p-III phage libraries in a final volume of 100 µL as described previously. Following four rounds of biopanning, 45 clones from the 3rd and 4th rounds were tested by micropanning. Of the 45, 23 scored negative. The 3rd round phage yielded two clones that scored 4+, two that scored 3+ and two that scored 2+. From the 4th round, one clone scored 4+, one scored 3+ and three scored 2+. G-tracking DNA sequencing revealed six unique sequences. Only one, clone 3G3, was strongly positive in the phage-capture ELISA. Four base DNA sequencing gave the following translated peptide sequence:

CLGVLGKLC (SEQ ID NO:58).

Example 10

Peptide Conjugation to Non-immunogenic, Multivalent Carriers

Several tetravalent platforms for the development of B cell tolerogens have been developed as described in co-owned and co-pending U.S. patent applications, Ser. Nos., 08/118,055, filed Sep. 8, 1993, 08/152,506, filed Nov. 15, 1993, and U.S. Pat. Nos. 5,268,454, 5,276,013 and 5,162,515 which are incorporated by reference herein in their entirety. Candidate peptides selected by aPL antibody screens of epitope libraries are conjugated and tested for modifications of immunochemical behavior such as antibody binding.

Non-immunogenic multivalent platforms with amine groups are synthesized as shown in the following scheme.

Amine on Platform—Carboxyl on Peptide

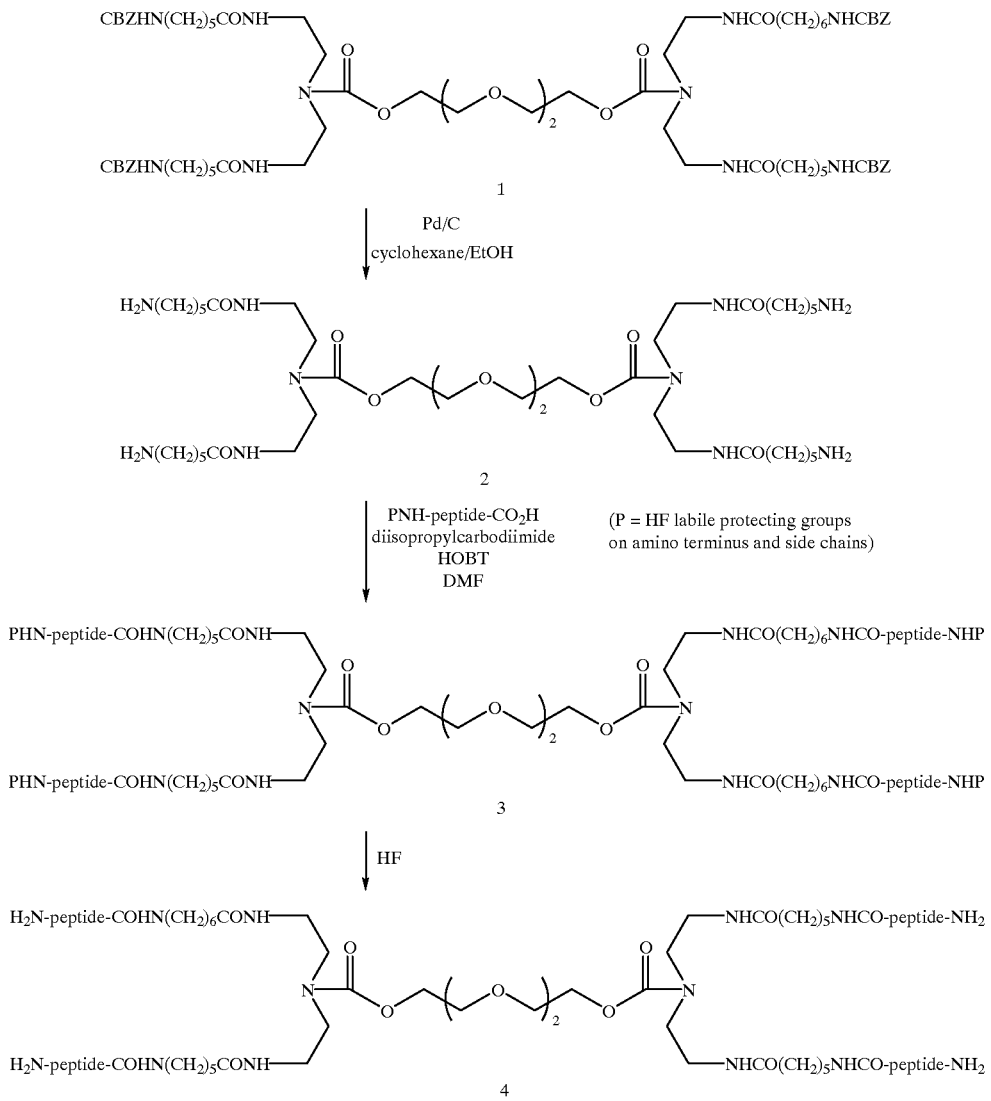

Compound 2: A solution of 8.0 g (5.7 mmol) of 1 in 50 mL of absolute EtOH and 35 mL of cyclohexene was placed under nitrogen, and 500 mg of 10% Pd on carbon was added. The mixture was refluxed with stirring for two hours. When cool, the mixture was filtered through Celite and concentrated to give 5.0 g of 2 as an oil. $^1$H NMR (50/50 CDCl$_3$/CD$_3$OD) d 1.21 (m, 8H), 1.49 (m, 8H), 1.62 (m, 8H), 2.19 (t, J=7.4 Hz, 8H), 2.67 (t, J=7.4 Hz, 8H), 3.36 (bd s, 16H), 3.67 (s, 4H), 3.71 (m, 4H), 4.21 (m, 4H).

Protected Peptide with Free Carboxyl (PHN-peptide-CO$_2$H

A peptide is synthesized with standard solid phase methods using FMOC chemistry on a Wang (p-alkoxybenzyl) resin, using trifluoroacetic acid (TFA) stable protecting groups (benzyl ester or cyclohexyl ester on carboxyl groups and carbobenzyloxy (CBZ) on amino groups). Amino acid residues are added sequentially to the amino terminus. The peptide is removed from the resin with TFA to provide a peptide with one free carboxyl group at the carboxy terminus and all the other carboxyls and amines blocked. The protected peptide is purified by reverse phase HPLC.

Peptide—Platform Conjugate, 4

The protected peptide (0.3 mmol) is dissolved in 1 mL of dimethylformamide (DMF), and to the solution is added 0.3 mmol of diisopropylcarbodiimide and 0.3 mmol of 1-hydroxybenzotriazole hydrate (HOBT). The solution is added to a solution of 0.025 mmol tetraamino platform, 2 in 1 mL of DMF. When complete, the DMF is removed under vacuum to yield a crude fully protected conjugate 3. The conjugate, 3, is treated with hydrofluoric acid (HF) in the presence of anisole for 1 hour at 0° to give conjugate 4. Purification is accomplished by preparative reverse phase HPLC.

The following scheme shows the attachment of an amino group of a peptide to a carboxy group on a platform.

Carboxyl on Platform—Amine on Ligand

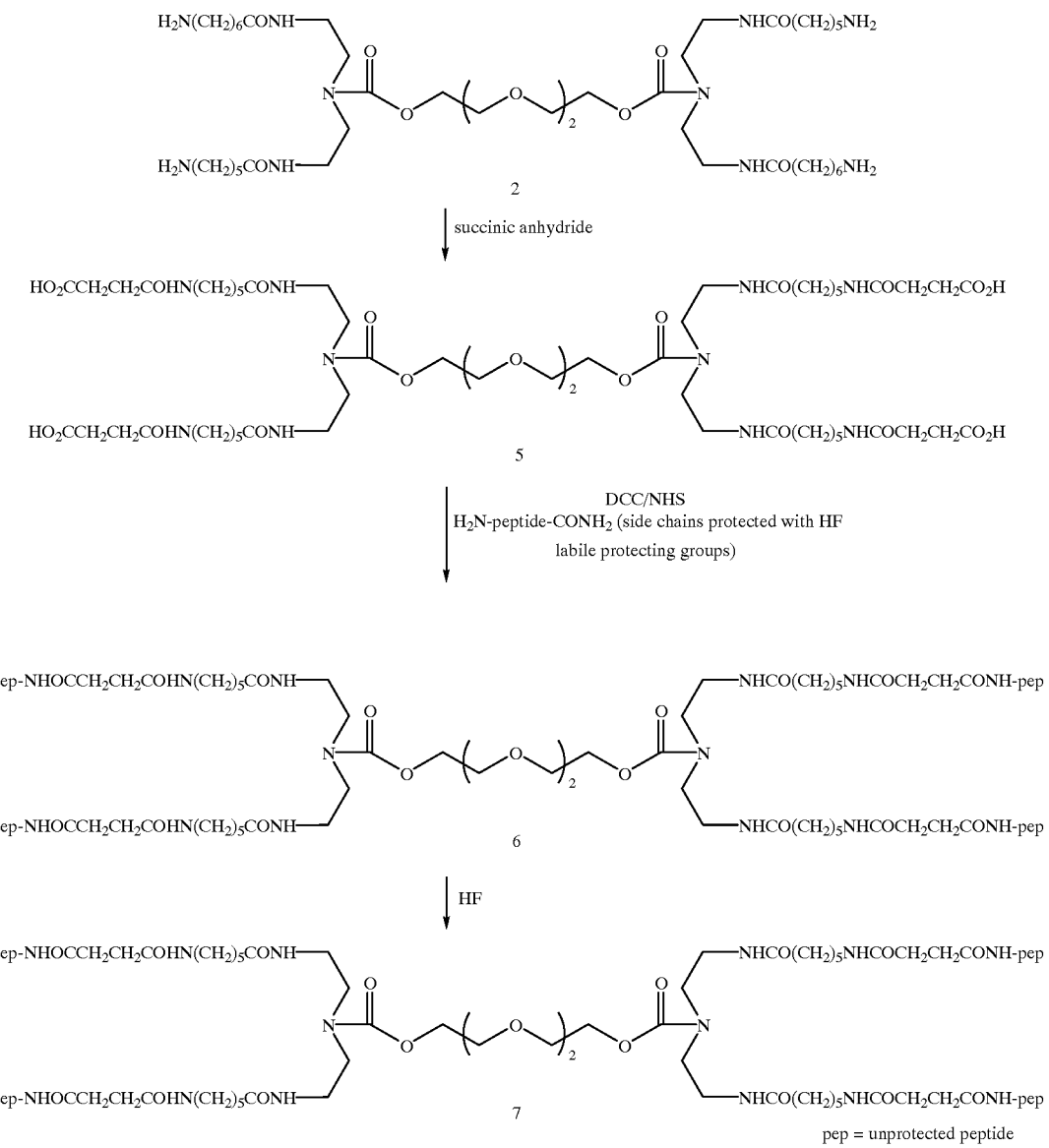

Compound 5—Platform with Four Carboxylic Acid Groups

Succinic anhydride (1.0 g, 10 mmol) is added to a solution of 861 mg (1.0 mmol) of 2 and 252 mg (3.0 mmol) of NaHCO$_3$ in 20 mL of 1/1 dioxane/H$_2$O, and the mixture is stirred for 16 hours at RT. The mixture is acidified with 1N HCl and concentrated. The concentrate is purified by silica gel chromatography to provide 5.

Protected Peptide with Free Amine (H$_2$N-peptide-CONH$_2$)

A peptide is synthesized with standard solid phase methods on an amide resin, which resulted in a carboxy terminal amide after cleavage from the resin, using TFA stable protecting groups (benzyl ester or cyclohexyl ester on carboxyl groups and CBZ on amino groups). Amino acid residues are added sequentially to the amino terminus using standard FMOC chemistry. The peptide is removed from the resin with trifluoroacetic acid to provide a protected peptide with a free amine linker. The protected peptide is purified by reverse phase HPLC.

Peptide—Platform Conjugate, 7

A solution of 0.05 mmol of protected peptide with free amine, (H$_2$N-peptide-CONH$_2$), 0.1 mmol of diisopropylethyl amine, and 0.01 mmol of 5 in 1 mL of DMF is prepared. BOP reagent (benzotriazol-1-yloxy-tris (dimethylamino)phosphonium hexafluorophosphate) (0.1 mmol) is added, and the mixture is stirred until the reaction is complete as evidenced by analytical HPLC. The peptide protecting groups are removed by treatment with HF in the presence of anisole at 0° to give conjugate with protecting groups removed, 7. Compound 7 is purified by preparative reverse phase HPLC.

The following scheme shows how to attach a sulfhydryl linker to the amino terminus of a peptide and, in turn, attach the peptide/linker to a tetrabromoacetylated platform to give compound 13.

Haloacetyl on Platform and Sulfhydryl on Peptide

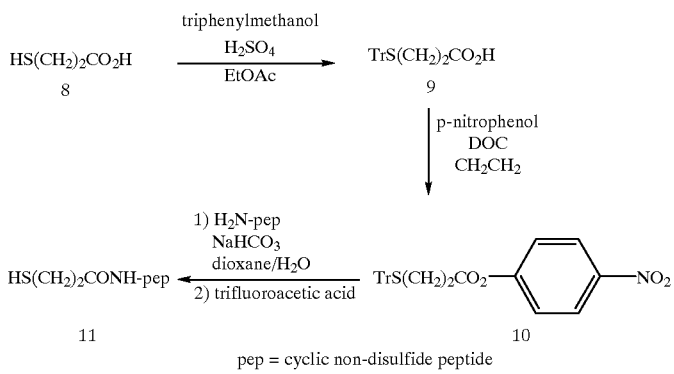

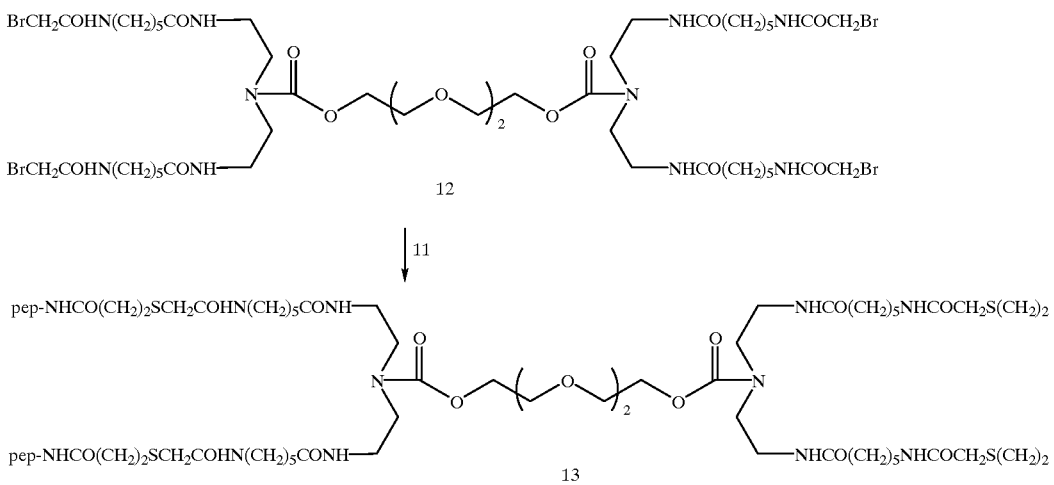

Compound 9

Concentrated sulfuric acid (100 uL) was added to a 60° C. solution of 4.48 g (17.2 mmol) of triphenyl methanol and 1.62 g (15.3 mmol, 1.3 mL) of 3-mercaptopropionic acid in 35 mL of EtOAc. The mixture was stirred at 60° C. for 10 minutes, allowed to cool to room temperature (RT), and placed on ice for 1 hour. The resulting white solid was collected by filtration to give 4.52 g (75%) of 9.

Compound 10

Dicyclohexyl carbodiimide (DCC) (2.41 g, 11.7 mmol) was added to a 0° C. solution of 2.72 g (7.8 mmol) of 2 and 1.08 g (7.8 mmol) of p-nitrophenol in 41 mL of $CH_2Cl_2$. The mixture was stirred for 16 hours allowing it to come to RT. The mixture was filtered to remove N,N-dicyclohexylurea (DCU), and the filtrate was concentrated. The residue was crystallized from hexane/$CH_2Cl_2$ to give 3.17 g (86%) of 10 as pale yellow crystals.

Compound 11—cyclic Thioether Peptide with Mercaptopropionyl Linker Attached

A solution of a cyclic thioether peptide (an analogue of a disulfide cyclized peptide in which one sulfuir was replaced with a $CH_2$) and sodium bicarbonate in water and dioxane was treated with p-nitrophenyl ester 10. If the peptide contains lysine, it must be appropriately blocked. The resulting modified peptide was treated with trifluoroacetic acid to provide thiol linker modified peptide 11.

Compound 13—conjugate of Cyclic Thioether Peptide and Bromoacetylated Platform

To a He sparged solution of 0.10 mmol of thiol modified peptide 11 in 100 mM sodium borate pH 9, was added 0.025 of bromoacetylated platform 12 as a 40 mg/mL solution in 9/1 MeOH/$H_2O$). The solution was allowed to stir under $N_2$ atmosphere until conjugation was complete as evidenced by HPLC. The conjugate was purified by reverse phase HPLC.

Example 12

Synthesis of LJP 685

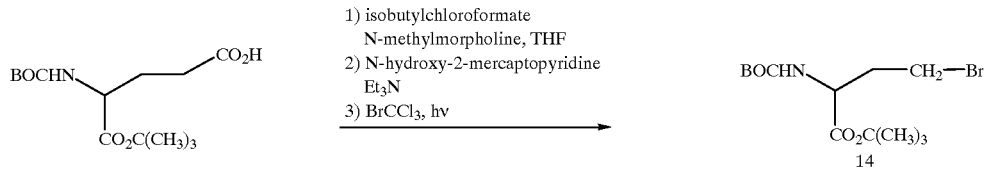

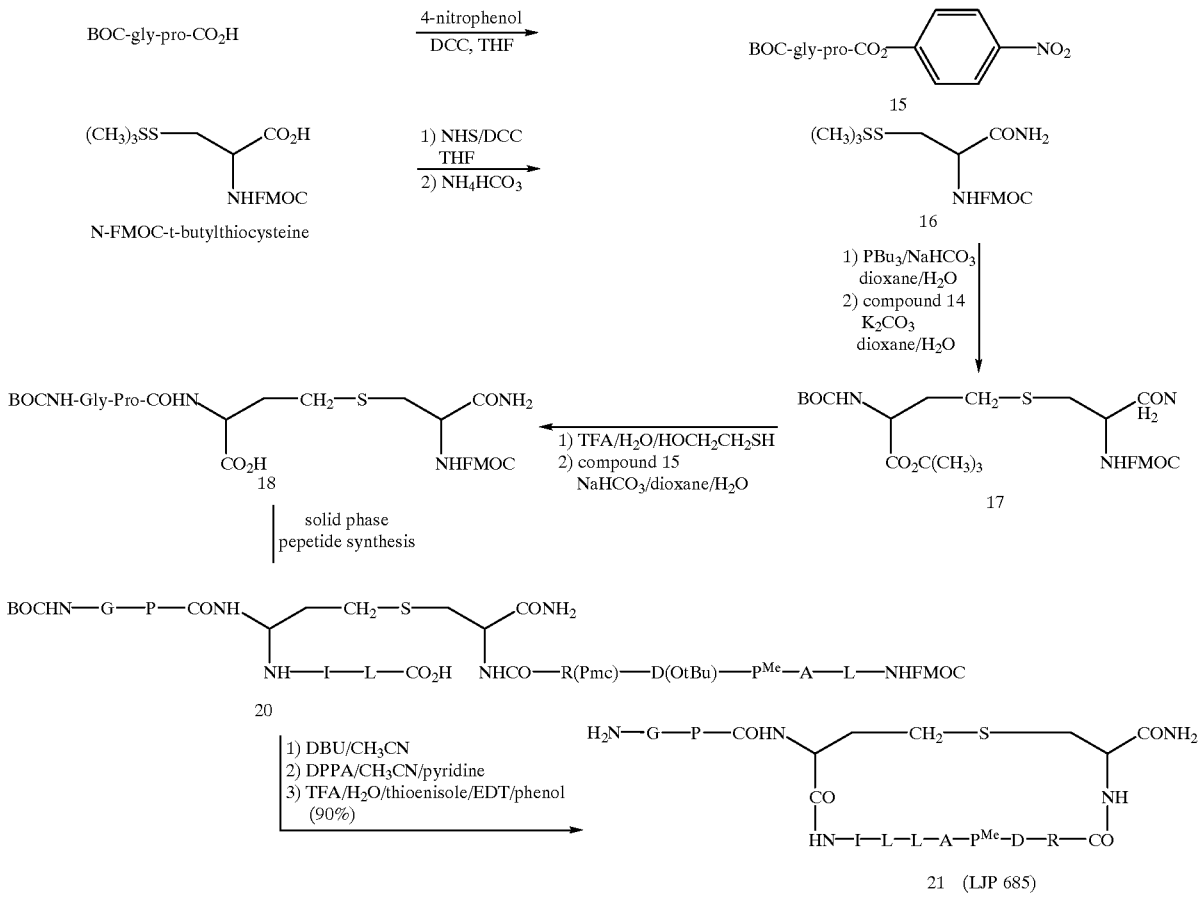

γ-bromo-N-BOC-α-aminobutryic Acid t-butyl Ester, Compound 14

A solution of 4.03 g (13.3 mmol) of N-BOC-glutamic acid-α-t-butyl ester and 1.61 mL (1.48 g, 14.6 mmol) of N-methylmorpholine in 40 mL of dry THF under N$_2$ atmosphere was cooled to 15°. Isobutylchloroformate (1.73 mL, 1.82 g, 13.3 mmol) was added to the mixture dropwise. The mixture was stirred for 10 minutes and a solution of 2.03 g (16.0 mmol) of N-hydroxy-2-mercaptopyridine in 8 mL of THF was added followed by 2.23 mL (1.62 g, 16.0 mmol) of Et$_3$N. The mixture was covered with foil to keep out light and allowed to stir at room temperature for 1 hour. The mixture was filtered and the filtrate was concentrated on the rotary evaporator taking care to minimize exposure to light. The concentrate was dissolved in 20 mL of BrCCl$_3$ and the solution was cooled to −70° C. The solid was placed under vacuum, then purged with N$_2$, allowed to come to room temperature, placed in a 20° water bath, and irradiated from above at close range with a 500W sunlamp for 5 minutes. The mixture was concentrated on the rotary evaporator and purified by silica gel chromatography (40 mm×150 mm, toluene was used as eluent until UV active material finished eluting, 2% EtOAc/toluene (500 mL), 5% EtOAc/toluene (500 mL). Impure fractions were repurified. Pure fractions by TLC (R$_f$ 0.23, 5% EtOAc/toluene) were combined and concentrated to give 3.23 g (72%) of compound 14 as a waxy solid.

N-BOC-glycylproline-4-nitrophenyl Ester, Compound 15

A solution of 3.0 g (11.6 mmol) of N-BOC-glycylproline and 1.93 g (13.9 mmol) of 4-nitrophenol in 82 mL of dry THF was cooled to 0° C. and 3.34 g (16.2 mmol) of DCC was added. The mixture was stirred at 0° C. for 1 hour, the ice bath was removed, and the mixture was stirred for 16 hours at room temperature. HOAc (579 μL) was added to the mixture and it was allowed to stir for 30 minutes. The mixture was kept in the freezer for 30 minutes and filtered under vacuum. The filtrate was concentrated and purified by silica gel chromatography (18×150 mm bed, 2.5% EtOAc/ 97.5% CH$_2$Cl$_2$/1% HOAc). Traces of acetic acid were removed by concentrating from dioxane several times on the rotary evaporator. The concentrate was triturated with 3/1 hexane Et$_2$O and the resulting white solid was collected by filtration to give 4.1 g (90%) of compound 15 as a white solid; TLC R$_f$ 0.09, 40/60/1 EtOAc/hexane/HOAc; $^1$H NMR (CDCl$_3$) δ 1.09–2.55 (m, 4H), 1.48 (s, 9H), 3.47–3.77 (m, 2H), 4.05 (m, 2H), 4.74 (m, 1H), 5.45 (bd s, 1H), 7.35 (d, 2H), 8.30 (d, 2H).

N-FMOC-S-t-butylthiocysteineamide, Compound 16

A solution of 5.0 g (11.6 mmol) of FMOC-S-t-butylthiocysteine and 1.33 g (11.6 mmol) of N-hydroxysuccinimide in 115 mL of THF was cooled to 0° C. To the solution was added 3.58 g (17.37 mmol) of DCC. The mixture was stirred at 0° C. for 1 hour and 42.9 mL of a solution of 1.6 g of (NH$_4$)HCO$_3$ in 50 mL of water was added. The mixture was stirred for 4.5 hours, allowing the ice bath to gradually warm to room temperature and concentrated on a rotary evaporator to remove THF and give an aqueous phase with white solid. The mixture was stirred with 200 mL of CH$_2$Cl$_2$ until most of the solid dissolved, then was shaken with 100 mL of 1N HCl solution. The CH₂Cl₂ layer was washed with 100 mL of saturated NaHCO₃ solution, dried (Na₂SO₄), and filtered. The filtrate was brought to a boil on a hot plate and crystallized from 300 mL of CH₂Cl₂/hexane to give 4.36 g (87%) of compound 16 as a white solid: mp 127°–129° C.; TLC R$_f$ 0.29, 95/5/1 CH₂Cl₂/CH₃CN/MeOH, ¹H NMR (CDCl₃) δ 1.36 (s, 9H), 3.06–3.24 (m, 2H), 4.25 (t, 1H), 4.55 (m, 3H), 5.56 (bd s, 1H), 5.70 (bd s, 1H), 6.23 (bd s, 1H); ¹³C NMR (CDCl₃) 29.8, 41.9, 47.1, 48.5, 54.2, 67.2, 120.0, 125.0, 127.1, 127.8, 141.3, 143.6, 156.1, 172.2.

Analysis, Calculated: C, 61.4%; H, 6.1%; N, 6.5%. Found: C, 61.5%; H, 6.0%; N, 6.5%.

Compound 17

Water (16.9 mL) was added to 2.91 g (6.75 mmol) of compound 16 in 33.8 mL of dioxane and the solution was sparged with nitrogen for 5–10 minutes. The mixture was kept under a nitrogen atmosphere and 1.13 g (13.5 mmol) of NaHCO₃ was added followed by 1.77 mL (1.44 g, 7.09 mmol) of PBu₃. The mixture was stirred at room temperature for 1 hour and partitioned between 1×100 mL of 1N HCl and 2×100 mL of CH₂Cl₂. The CH₂Cl₂ layers were combined and concentrated and the resulting white solid was partially dissolved in 33.8 mL of dioxane. Water (9 mL) was added and the mixture was purged with nitrogen for 5–10 minutes. The mixture was kept under nitrogen atmosphere and 2.17 g (16.9 mmol) of K₂CO₃ was added followed by 2.63 g (8.1 mmol) of compound 14. The mixture was stirred for 16 hours and partitioned between 1×100 mL of 1N HCl and 2×100 mL of 10% MeOH/CH₂Cl₂. The CH₂Cl₂ layers were combined, dried with NaSO₄, filtered and concentrated to a semisolid residue. Purification by silica gel chromatography (1/3 CH₃CN/CH₂Cl₂) gave 3.2 g (80%) of compound 17 as awhite solid; TLC R$_f$ 0.27, 1/3 CH₃CN/CH₂Cl₂. Further purification of an analytical sample was done by recrystallizing from hexane/EtOAc; mp 104–106.5° C.; ¹H NMR (CDCl₃) δ 1.47 (s, 9H), 1.49 (s, 9H), 1.96 (m, 1H), 2.11 (m, 1H), 2.69 (m, 2H), 2.88 (m, 1H), 3.03 (m, 1H), 4.29 (t, 1H), 4.36 (m, 2H), 4.50 (m, 2H), 5.21 (m, 1H), 5.49 (m, 1H), 5.81 (m, 1H), 6.54 (m, 1H), 7.34 (t, 2H), 7.42 (t, 2H), 7.61 (d, 2H), 7.80 (d, 2H); ¹³C NMR (MeOH) δ 26.1, 26.7, 28.2, 28.7, 34.8, 54.8, 55.7, 68.1, 80.5, 82.7, 120.9, 126.3, 128.2, 128.8, 142.6, 145.2, 160.0, 162.7, 173.4, 175.8.

Analysis, Calculated for C₃₁H₄₁N₃O₇S: C, 62.08; H, 6.89; N, 7.01. Found: C, 62.23; H, 7.12; N, 7.39.

Compound 18

A solution of 20/1/1 TFA/H₂O/mercaptoethanol (23.2 mL) was added to 1.27 g (2.11 mmol) of compound 17. The mixture was stirred at room temperature for 1 hour and concentrated to a volume of about 3 mL. 50 mL of ether was added to precipitate the product. The resulting solid was washed with two more portions of ether and dried under vacuum to give 812 mg of solid. The solid was suspended in 10.6 mL of dioxane and 10.6 mL of H₂O. NaHCO₃ (355 mg, 4.22 mmol) was added to the mixture followed by a solution of 1.33 g (3.38 mmol) of compound 15 in 10.5 mL of dioxane. The mixture was allowed to stir at room temperature for 20 hours and partitioned between 100 mL of 1N HCl and 3×100 mL of CH₂Cl₂. The combined CH₂Cl₂ layers were dried (Na₂SO₄), filtered and concentrated. Purification by silica gel chromatography (35×150 mm; step gradient, 5/95/1 MeOH/CH₂CL₂/HOAc (1 L) to 10/95/1). Pure fractions were concentrated and the residue was triturated with ether to give 881 mg (60%) of compound 18; TLC R$_f$ 0.59, 10/90/1 MeOH/CH₂Cl₂/HOAc; mp 116–117.5° C.; ¹H NMR (CDCl₃) δ 1.41 (s, 9H), 2.00 (m, 2H), 2.18 (m, 2H), 2.56 (m, 1H), 2.69 (m, 1H), 2.85 (m, 2H), 3.49 (m, 2H), 3.62 (m, 2H), 3.85 (m, 2H), 4.08 (m, 1H), 4.12 (m, 1H), 4.22 (t, 1H), 4.38 (m, 1H), 4.49 (m, 2H), 4.61 (m, 2H), 7.78 (d, bd s, 1H), 6.12 (bd s, 1H), 6.43 (bd s, 1H), 7.35 (d, 2H), 7.40 (d, 2H), 7.61 (d, 2H), 7.78 (d, 2h); ¹³C NMR (CDCL₃) δ 25.3, 27.8, 28.6, 29.4, 32.6, 35.1, 44.1, 46.9, 47.3, 52.2, 53.9, 61.2, 67.8, 80.8, 120.8, 125.7, 128.2, 129.0, 142.0, 144.5, 157.6, 157.8, 170.6, 181.2, 182.9, 183.1.

Analytical, Calculated for C₃₄H₄₃N₅O₉S: C, 58.52; H, 6.21; N, 10.03. Found: C, 58.38, H, 6.17; N, 10.20.

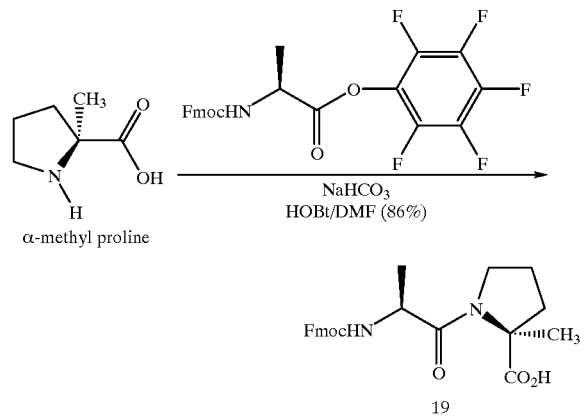

N-FMOC-L-Alanyl-L-2-methylproline, Compound 19

A solution of 2-methylproline (Seebach et al. (1983) *J. Am. Chem. Soc.* 105:5390–5398) (1.00 g, 4.76 mmol), 4.00 g (47.6 mmol) of NaHCO₃, and 31 mg (0.23 mmol) of HOBT in 6.9 mL of DMF was cooled to 0° C. and 3.18 g (6.66 mmol) of N-FMOC-L-alanine was added. The reaction was stirred for 1 hour at 0° C., then at room temperature for 18 hours. The mixture was partitioned between 50 mL of EtOAc and 3×50 mL of 1N HCl. The EtOAc layer was dried (MgSO₄), filtered and concentrated. Purification by silica gel chromatography (step gradient 45/55/1 EtOAc/Hexane/ HOAc to 47/53/1 EtOAc/Hexane/HOAc to 50/50/1 EtOAc/ Hexane/HOAc) gave 1.72 g (86%) of compound 19 as a white solid. The product was concentrated several times from dioxane to remove traces of acetic acid: mp 59–60° C.; ¹H NMR (CDCl₃) δ 1.39(d, 3H), 1.93 (m,2H), 2.06 (m, 2H), 3.78 (m, 2H), 4.22 (m, 1H), 4.40 (d, 2H), 4.56 (m, 1H), 5.09 (t, 1H), 5.69 (d, 1H), 7.32 (t, 2H), 7.42 (t, 2H), 7.62 (d, 2H), 7.78 (d, 2H); ¹³C NMR (CDCl₃) δ 17.8, 21.8, 23.8, 37.9, 47.1, 48.5, 65.9, 67.0, 120.0, 125.1, 127.1, 127.7, 141.3, 144.1, 155.6, 172.9, 175.1.

N-FMOC-L-Leucinyl-HMPB-MBHA Resin

A solution of N-FMOC-L-leucine in 22.5 mL of CH₂Cl₂ and a few drops of DMF was prepared and cooled to 0° C. To the solution was added 1.71 mL (1.38 g, 10.9 mmol) of diisopropylcarbodiimide (DIC) and the mixture was stirred for 20 minutes at 0° C. The mixture was concentrated to an oil; meanwhile, enough DMF (approximately 3 mL) was added to 2.5 g (0.87 mmol/g, 2.18 mmol) HMPB-MBHA resin (Nova Biochem) to swell the resin. The concentrated oil was dissolved in a minimal amount of DMF (approximately 1 mL) and added to the swelled resin followed by a solution of 266 mg (2.18 mmol) of DMAP dissolved in approximately 1 mL of DMF. The mixture was gently rocked for 1 hour and washed (2×DMF, 2×MeOH, 2×DMF, 2×MeOH). The resin was dried under vacuum to give 2.77 g (85%) and the substitution was determined by the Geisen test to be 0.540 mmol/g.

N-FMOC-linear Peptide with t-butyl Ester on Aspartic Acid and Pmc Group on Arginine and with Thioether Insert, Compound 20

This peptide was prepared by standard FMOC synthesis on N-FMOC-L-leucinyl-HMPB-MBHA resin. Three equivalents of amino acid, HOBT and (DIC) were used for each coupling step with the exception of the coupling step of compound 18. Two equivalents of compound 18 were used with three equivalents of HOBT and diisopropylcarbodiimide. Each step was monitored by using 10 $\mu$L of bromophenol blue indicator. Completeness of the reaction was also assessed with a ninhydrin test (beads turn blue for incomplete reaction with 1 mg is heated at 100° C. for 2 minutes with one drop of pyridine and one drop of 5% ninhydrin in EtOH and one drop of 80% phenol in EtOH). Thus, 1.13 mg (0.613 mmol) of resin was used to prepare the peptide. After the final coupling step, cleavage from the resin was accomplished by treatment with 15 mL of a solution of 1% trifluoroacetic acid in $CH_2Cl_2$ for 2 minutes. After 2 minutes, the solution was filtered under pressure into 30 mL of 10% pyridine in MeOH. This was repeated ten times and the filtrates which contained peptide as evidenced by HPLC (C18, gradient, 60/40/0.1 $CH_3CH/H_2O$/TFA to 90/10/0.1 $CH_3CN/H_2O$/TFA, 210 mn, 1 mL/min, 4.6 mm×250 mm column) were combined and concentrated. The concentrate was dissolved in 40 mL of 10% HOAc solution and purified by HPLC to give 0.528 g (49%) of peptide 20.

Conversion of Peptide 20 to Cyclic Peptide 21 (Removal of FMOC Group, Cyclization and Removal of Protecting Groups A solution (5 mL) of 99 $\mu$L of DBU in 10 mL of $CH_3CN$ was added to 96 mg (0.052 mmol) of peptide 20. The solution was stirred for 1 hour and concentrated to a residue. The residue was triturated with 2×10 mL of $Et_2O$ to give a white solid. The solid was dissolved in 100 mL of $CH_3CN$ and 312 $\mu$L (0.312 mmol) of 0.1 M solution of diphenylphosphorylazide (DPPA) in $CH_3CN$. The mixture was stirred for 20 hours and concentrated on a rotary evaporator. The residue was triturated with 2×50 mL of $Et_2O$ and the white opaque residue was treated with 5 mL of 92/3/2/3 TFA/anisole/EDT/$Me_2S$ for 1 hour. The product was precipitated by adding the mixture to 40 mL of $Et_2O$ in a 50 mL polypropylene centrifuge tube. The precipitate was cooled to 0° C. and centrifuged for 5 minutes at 2000 rpm. The supernatant was decanted and the pellet was washed with $Et_2O$ and recentrifuged. The pellet was dried and dissolved in 4 mL of 50/50 $CH_3CN/H_2O$. The mixture was diluted with 36 mL of $H_2O$/0.1% TFA, filtered and purified by HPLC (1"$C_{18}$ column, gradient, 10/90/0/1 $CH_3CN/H_2O$/TFA to 35/65/0.1 $CH_3CN/H_2O$/TFA, 230 nm). The pure fractions, as evidenced by HPLC, were lyophilized to give 52 mg (90%) of compound 21.

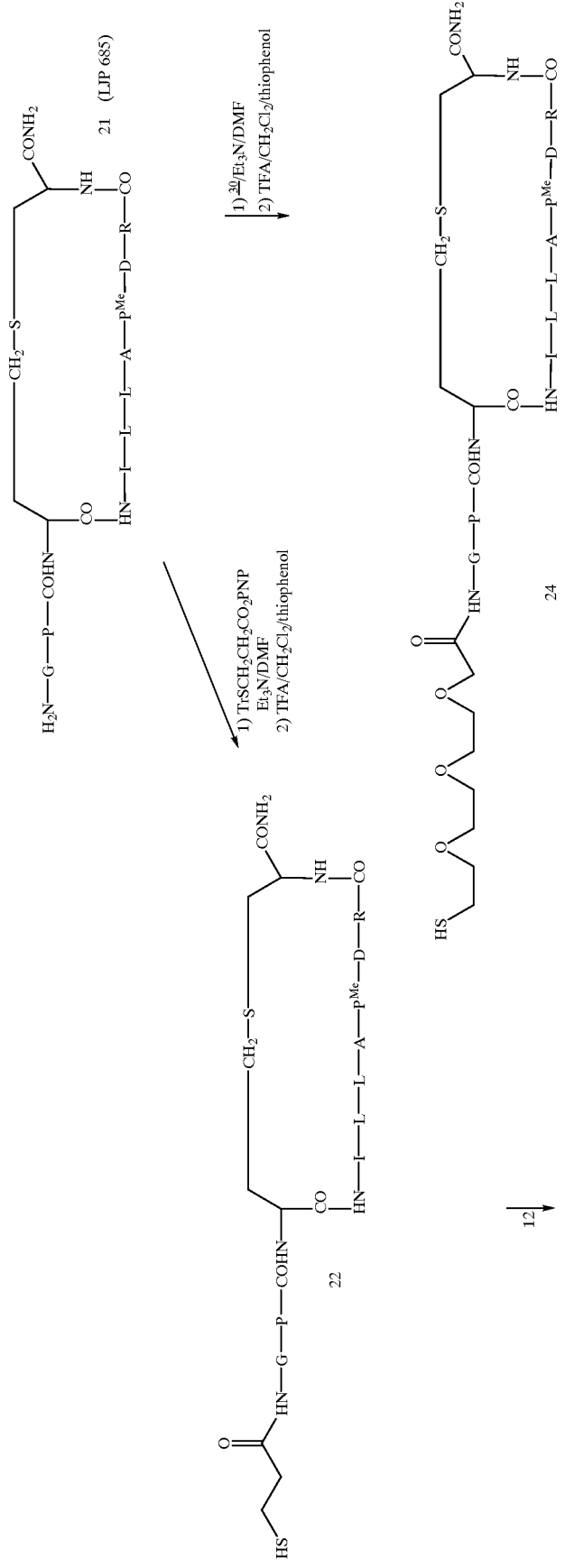
Example 12
Synthesis of Conjugates of LUP 685

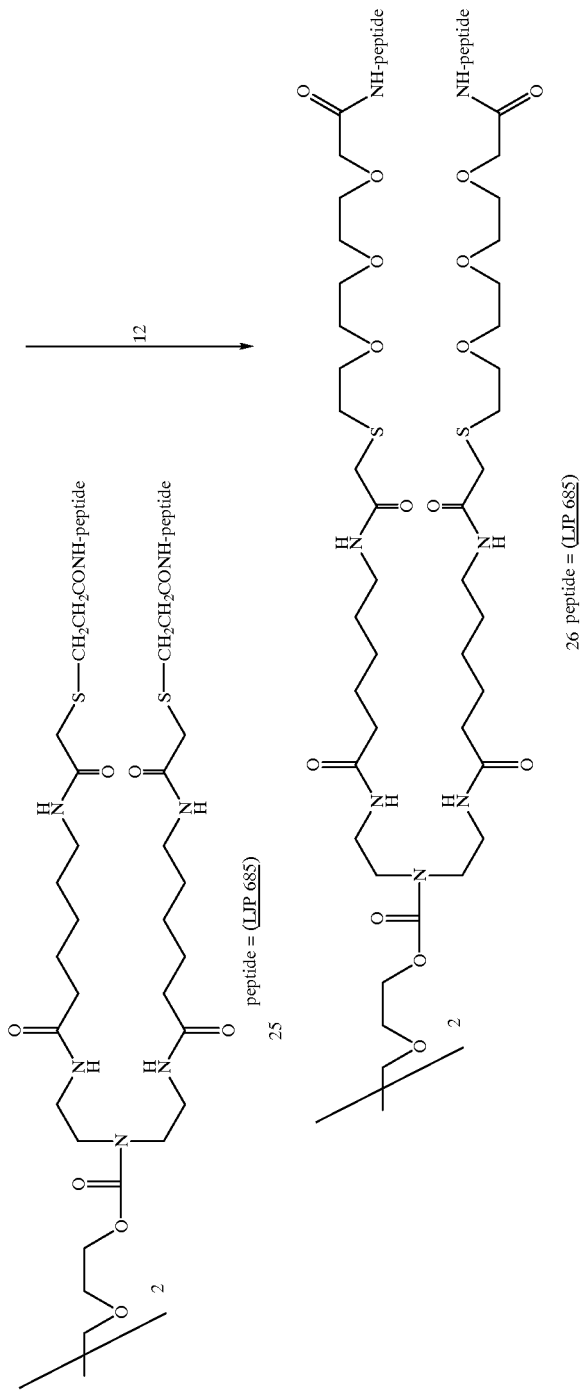

LJP 685, also referred to as compound 21, was treated with the PNP ester of 3-tritylmercaptopropionic acid and the resulting product was detritylated to give compound 22, the peptide with the free thiol linker. Reaction of an excess of compound 22 with valency platform molecule 12 produced tetravalent conjugate 25. Treatment of compound 21 with the longer linker, compound 33 (see reaction scheme below), followed by detritylation, gave compound 24. Compound 24 reacted with valency platform molecule 12 to give the tetraconjugate 26. Both conjugation reactions appeared very clean by HPLC.

Attachment of MTU Linker to LJP 685, Synthesis of Compound 24

To 15 mg (0.013 mmol) of compound 21 was added 160 $\mu$L of a solution of 29.5 mg of compound 23 and 17.5 $\mu$L of diisopropylethylamine in 0.5 mL of DMF. the mixture was stirred for 2 hours and precipitated from $Et_2O$. The precipitate was dried and dissolved in 650 $\mu$L of a solution of 1/1/0.056/0.040 TFA/CH2Cl2/thiophenol/$Me_2S$ and the solution was allowed to stand for 1 hour. Precipitation from $Et_2O$ gave crude compound 24 which was purified by HPLC ($C_{18}$, 15–45% $CH_3CN/H_2O$, 0.1% TFA). Fractions containing pure product were lyophilized to give 8.6 mg of compound 24 as a white solid.

LJP 685-MTU-AHAB-TEG, Compound 26

To a solution of 8.6 mg ($6.3 \times 10^{-6}$ mol) of compound 24 in 630 $\mu$L of He sparged pH 8.5 200 mM borate buffer was 40 $\mu$L of a 40 mg/mL solution of compound 12 in 9/1 $MeOH/H_2O$. The mixture was stirred for 24 hours and 1 mL of 10% $HOAc/H_2O$ solution was added. The mixture was purified by HPLC ($C_{18}$, gradient 25–55% $CH_3CN/H_2O$, 0.1% TFA) to give 8.3 mg of compound 26 (LJP 685-MTU-AHAB-TEG).

Example 13

Development of Extended SH Linkers

The thiobenzoate ester, compound 28, was prepared from compound 27. Compound 28 was converted to compound 22 in portions. The thiobenzoate was removed by ethanolysis and the resulting thiol was tritylated. The ethyl ester was then hydrolyzed to give compound 29. The nitrophenyl phosphate (PNP) ester, compound 30, was prepared from compound 29. Aminotrioxoudecanoicacid ethylester, compound 31, was prepared by treatment of compound 27 with sodium azide and reduction to the amine. Amine 31 was acylated with compound 30 to provide compound 32. Hydrolysis of compound 32 was achieved by treatment with sodium hydroxide to give a free carboxylic acid. The intermediate carboxylic acid was condensed with p-nitrophenol to give para-nitrophenyl (PNP) ester, compound 33. Linker 33 was attached to the peptide and the trityl group removed to give compound 34 which was used to produce an MTU-ATU-AHAB-TEG conjugate.

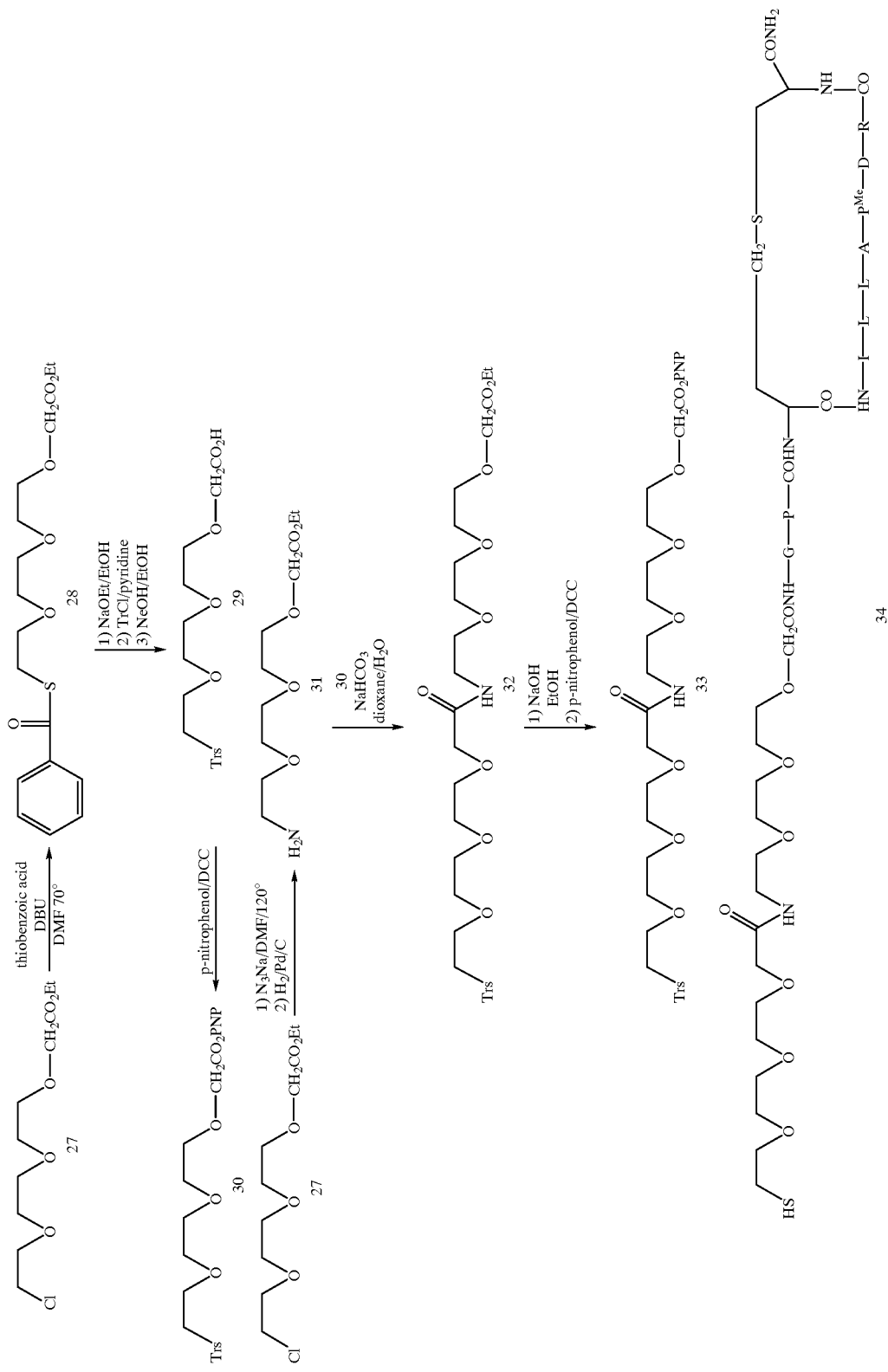

Example 14

Synthesis of a (LJP685)₄/MTU-ATU-AHAB-TEG Conjugate, Compound 35

Tetravalent conjugate 35 was prepared as shown below. The peptide with linkers attached, compound 34 was dissolved in He sparged, pH 8.5, 200 mM borate buffer. To the mixture was added 0.3 mol equivalents of platformn compound 12. The mixture was stirred for 1 hour and the product was purified by HPLC.

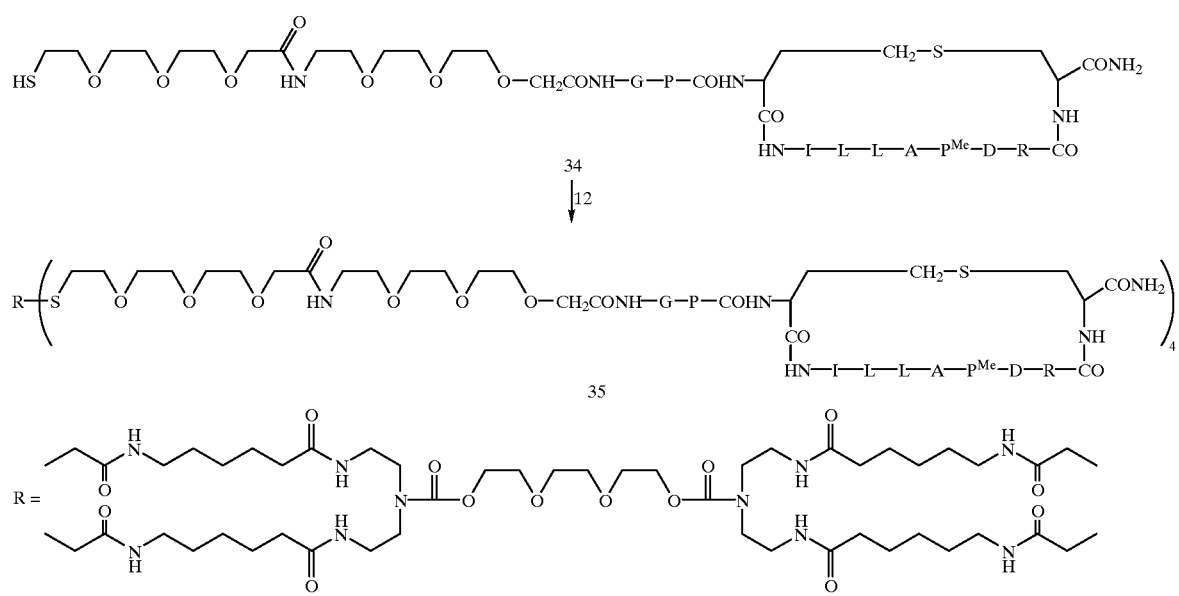

Example 15

Synthesis of a (LJP685)₄/DABA-PEG Conjugate, Compound 36

Treatment of IA-DABA-PEG with compound 24 in 8.5 borate buffer gave conjugate 36.

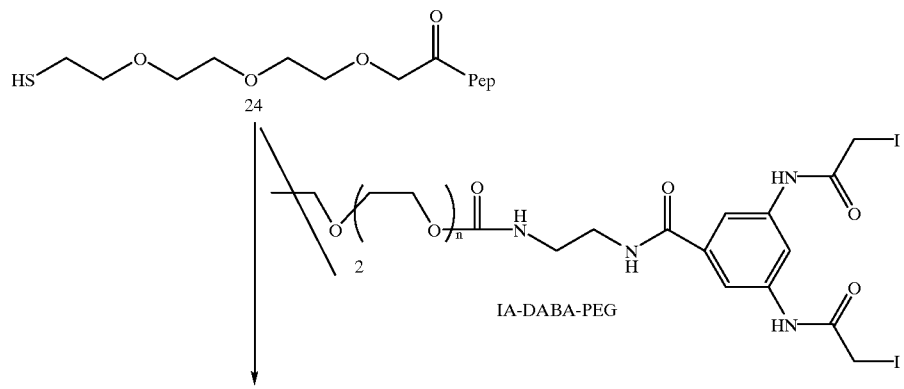

-continued

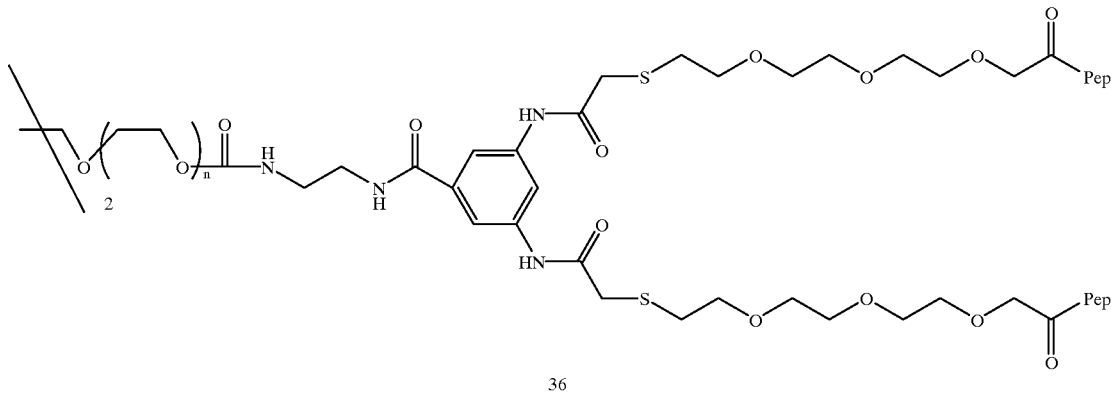

36

Pep = LJP 685

Example 16

T Cell Assay for Activation

Tritiated thymidine uptake by peptide-stimulated T cells was monitored in 96-well round bottom plates. A single-cell suspension of draining lymph node cells (mice) or isolated peripheral blood lymphocytes (human), $5 \times 10^5$ were mixed with between 1 and 30 μg of peptide in a final volume of 150 μL per well and incubated for 5 days at 37° C. in 5% $CO_2$. At that point, 1 micro curie of labeled thymidine was added and incubated for an additional 15–24 hours. The harvested cells were collected on filters and counted by liquid scintillation spectrometry.

Example 17

In vitro Induction of Tolerance

Figure 16:
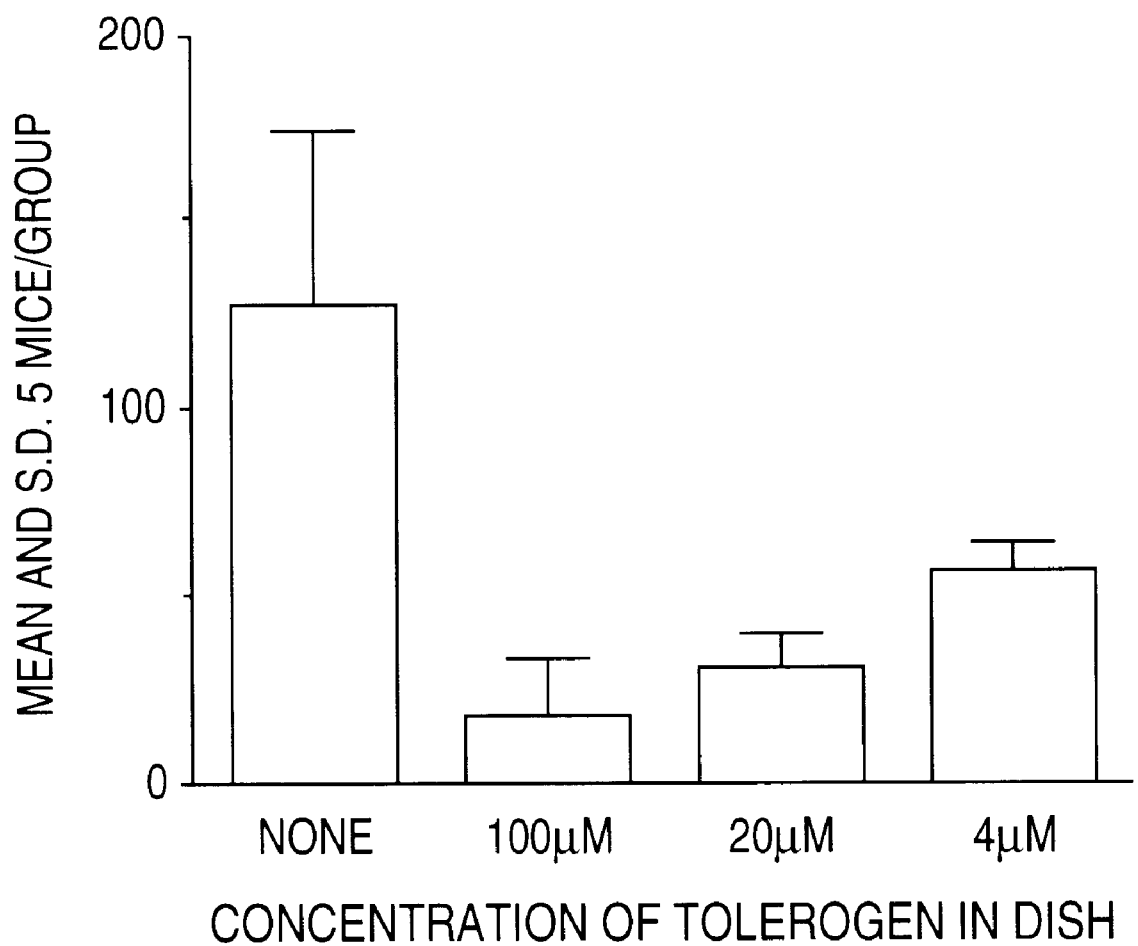
FIGS. 16 and 17 show the dose-dependent reduction in anti-685 antibody ABC at $10^8$M using spleen cells from mice immunized with LJP 685-KLH after the spleen cells were incubated with 100, 20 and 4 μM of LJP 685-MTU-DABA-PEG conjugate (compound 36 and LJP 685-ATU-MTU-AHAB-TEG conjugate (compound 35), respectively, for 2 hours.
Figure 17:
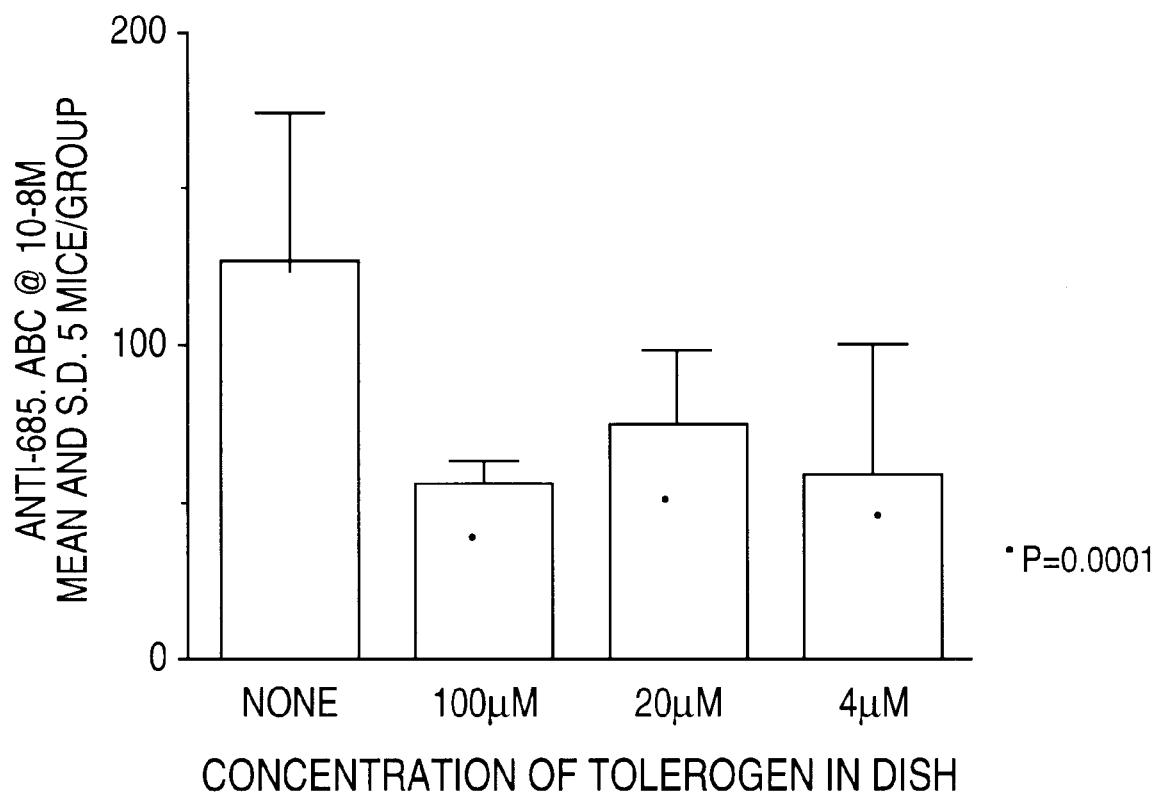

Eight groups, each containing five C57B1/6 mice, were primed with 10 μg/mouse of a conjugate of LJP685-KLH on alum plus *B. pertussis* vaccine as an adjuvant. After three weeks, spleens were harvested and single cells suspensions were prepared, washed three times with balanced salt solution and resuspended in complete RPMI-1640 medium at a concentration equivalent to one spleen/1.5 mLs of medium. The cell suspension was divided into aliquots of 2.5 mL/petri dish and incubated for 2 hours at 37° C. with $(LJP685)_4$-DABA-PEG, compound 36, and $(LJP685)_4$-TEG, compound 35, in concentrations of 100 μM, 20 μM and 4 μM. One group of cells was incubated without tolerogen and acted as the positive control. The cells were then washed with large volumes of balanced salt solution and resuspended in 2.5 mL of balanced salt solution. The cells were then injected into 650R irradiated syngeneic recipient mice in such a manner that all of the cells from a given treatment group were divided evenly into five recipients. All of the recipient mice, including the positive controls, were then given a booster immunization of 10 μg of LJP 685-KLH in saline, intraperitoneally. Seven days after the booster immunization, the mice were bled and their sera tested for the presence of anti-LJP 685 antibody. Treatment with either conjugate produced a significant, dose-dependent reduction of anti-LJP 685 antibodies as shown in FIGS. 16 and 17, which is measured by Antigen Binding Capacity (ABC) as described in Iverson, G. M., "Assay for in vivo adoptive immune responses," in HANDBOOK OF EXPERIMENTAL IMMUNOLOGY, Volume 2, Cellular Immunology (Weir, D. M., ed., Blackwell Scientific Publications, Palo Alto, Calif., 1986).

Example 18

NMR Solution Structure Analysis of the 5A12, CB2 and 3G3 Peptides

Two peptides isolated from phage library screens using the methodology described in the examples above were subjected to NMR analysis. The original peptide has a proline in the second to last position, however, this amino acid was removed since two dimensional (2D) double quantum filtered correlated spectroscopy (DQF-COSY) NMR data suggested the presence of two different structures from the cis and trans isomers at this position. Removal of the proline gave peptides with $K_d$'s in the 50–100 nM range for binding to ACA antibodies, and the expected number of peaks in the fingerprint region of the DQF-COSY spectrum. The resulting cyclic peptides are 5A12 (GPCLILAPDRCG) (SEQ ID NO:215) AND CB2 (GPClLARDRCG) (SEQ ID NO:216). The major difference between the peptides was the substitution of arginine for proline at position 8 which resulted in much less dispersion in the 1D 1H NMR spectrum of CB2 which was consistent with 5A12 being a more rigid peptide. The arginine substitution also produces a 0.55 kcal/mol stabilization of the ionized aspartyl carboxy group as reflected in pKa values. A structural analysis was carried out on the more ordered 5A12 peptide. Although deuterium exchange and temperature coefficient data show no evidence of hydrogen bonding, the Nuclear Overhauser Effect (NOE), Rotating Overhauser Effect (ROE) and coupling data are consistent with one structure. Distance geometry calculations yielded a family of 50 structures. The 15 best had a mean root mean square deviation (RMSD) for all atoms of 2.1±0.2 angstroms. We determined that the peptide has an oval shape with turns at opposite ends of the molecule, at the disulfide and at Proline 8 which is cis. There is also a kink in the backbone LIL region. Finally, the carboxy terminal glycine is very mobile as it is the only residue with a positive intraresidue NOE. This represents the first structural information determined about a peptide that mimics the ACA epitope on β2-GPI.

Figure 18:
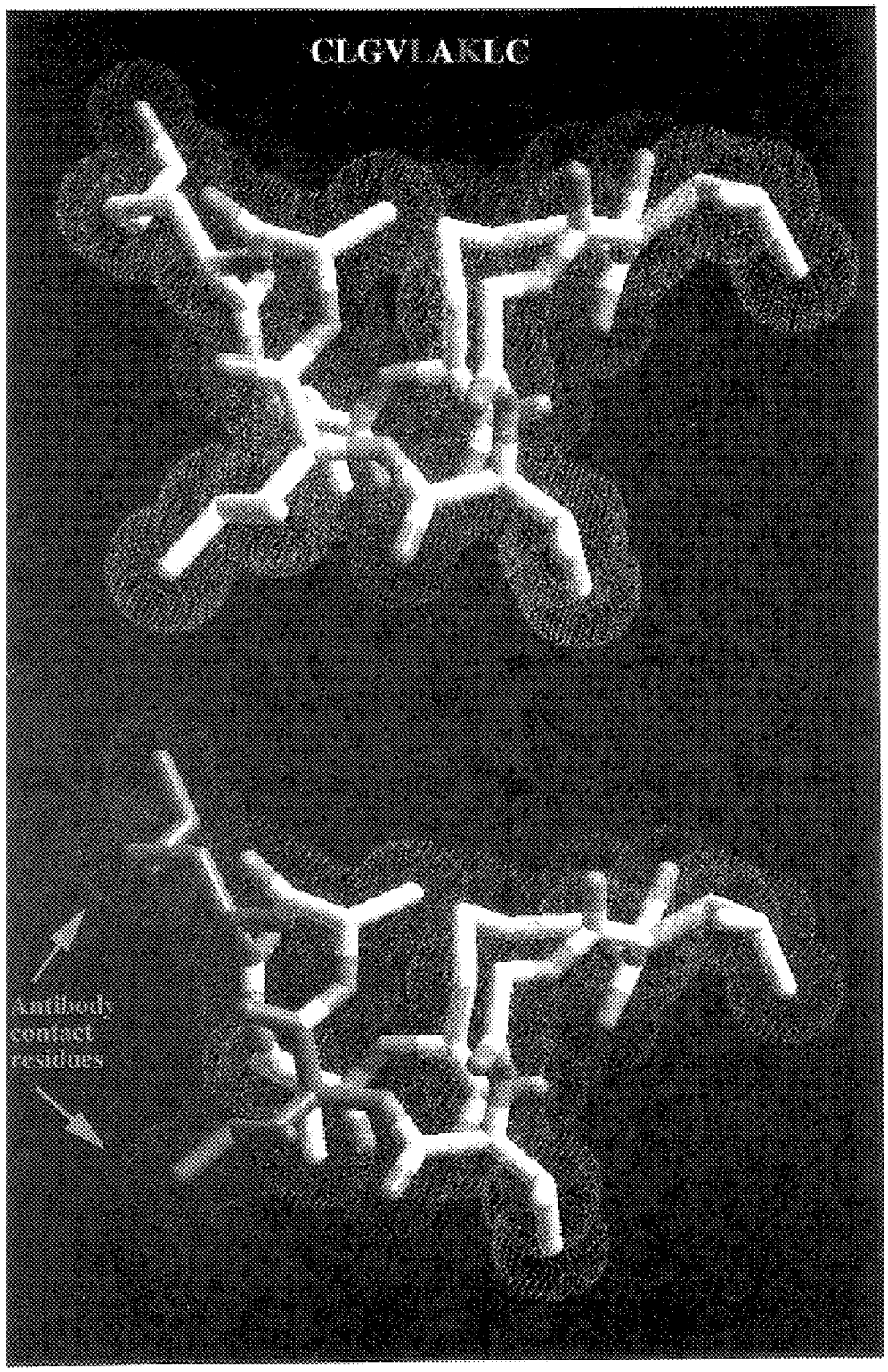
FIG. 18 displays the NMR structure closest to the centroid of the nine structures elucidated for peptide 925 and is a reasonable representation of the shape of the peptide 925 molecule.
Figure 19:
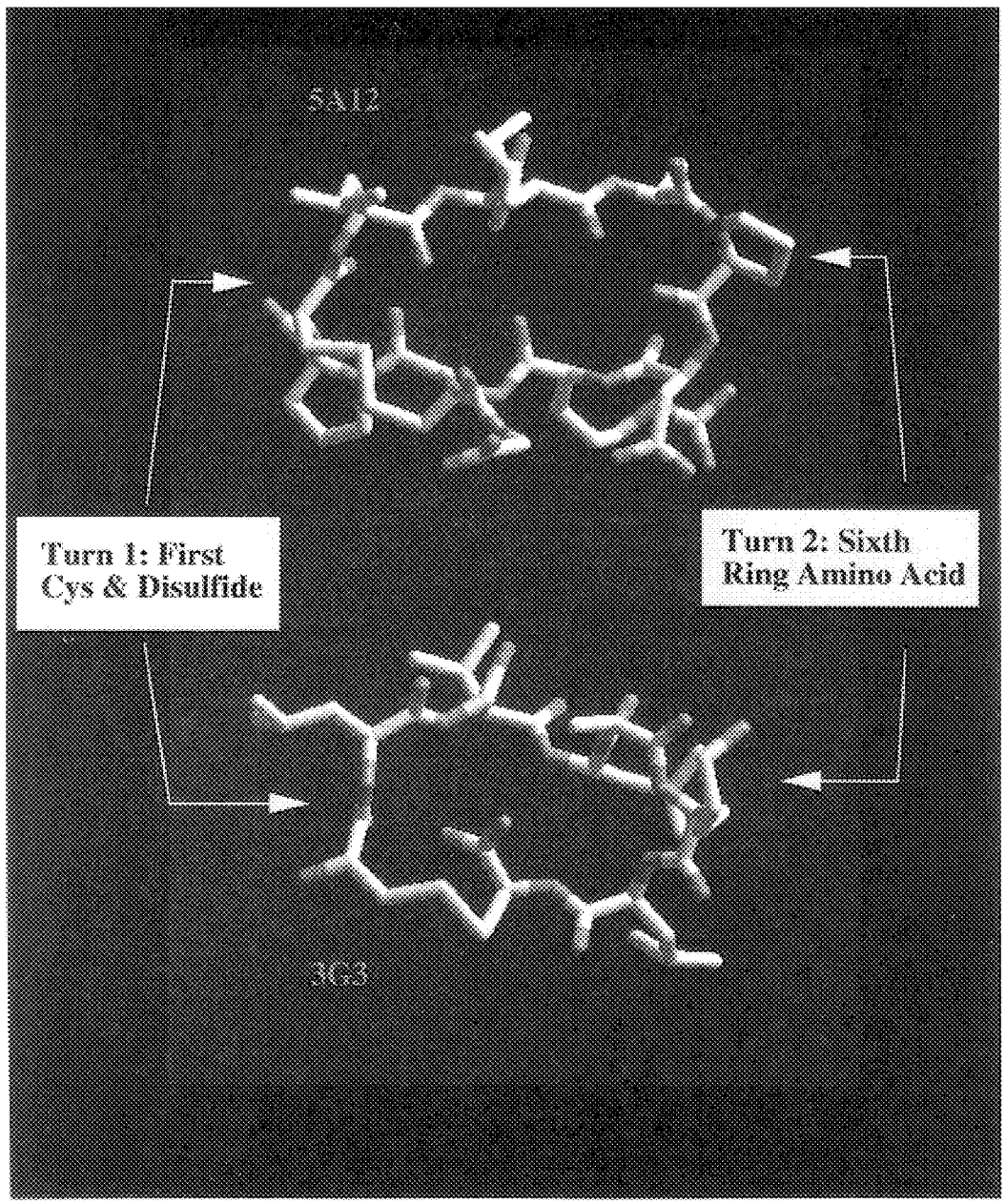
FIG. 19 compares the structure of peptide 925 (labeled at the bottom of the figure as 3G3) with the structure of peptide 5A12. Both peptides have turns at approximately the same positions in the peptide sequence.

NMR data coupled with distance geometry calculations were used to determine the three dimensional structure of peptide 925 (CLGVLAKLC) (SEQ ID NO:74), a truncated version of peptide 3G3 (AGPCLGVLGKLCPG) (SEQ ID NO:57) with alanine substituted for glycine in position 6 of the 925 peptide. The structure of peptide 925 was deter mined in water at pH 3.8 and at 25° C. An ensemble of nine structures were calculated all of which were consistent with the NMR data. The RMSD for all non-hydrogen atoms was 2.45±0.36 angstroms when each structure was compared to the centroid. FIG. 18 displays the structure closest to the centroid of the ensemble and, therefore, is a reasonable representation of the shape of the peptide 925 molecule. FIG. 19 compares the structure of peptide 925 (labeled at the bottom of the figure as 3G3) with the structure of peptide 5A12. Both peptides have turns at approximately the same positions in the peptide sequence.

Figure 20A:
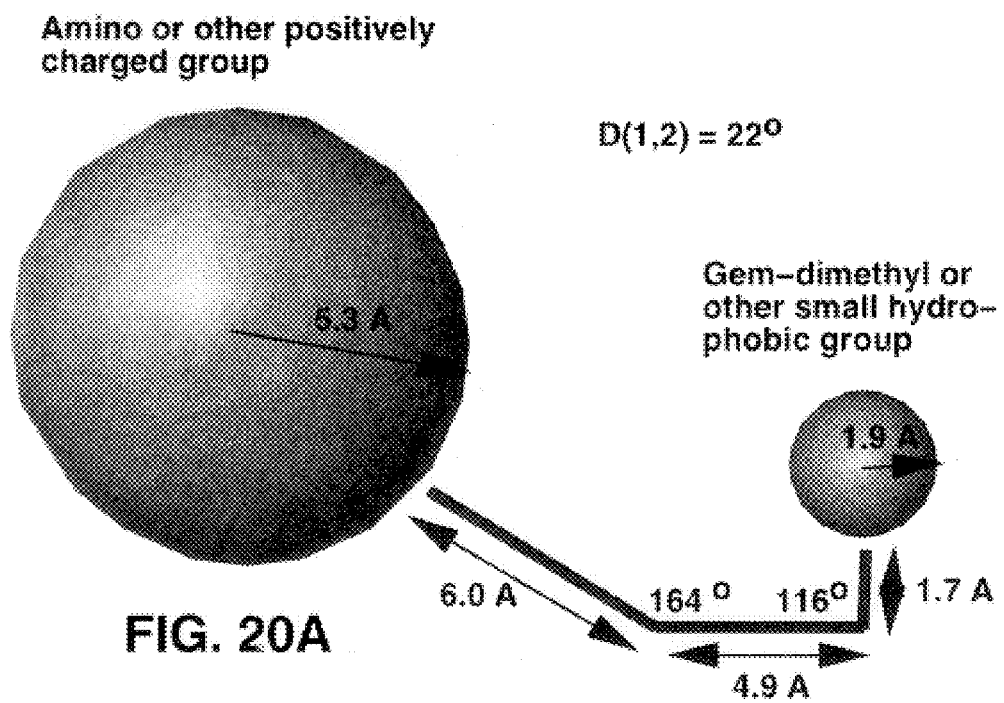
FIGS. 20A and 20B illustrate that the pharmacophore of aPL analogs has been tentatively identified as a small hydrophobic group and a positively charged group. The gem-dimethyl and amino groups of peptide 925 are tentatively identified as the pharmacophore of this peptide as shown in FIG. 20A. The lengths of the hydrocarbon linkers that tether the pharmacophore groups to some scaffold are specified in FIG. 20A as well as the distances separating the points at which these linkers are attached to the scaffold.
Figure 20B:
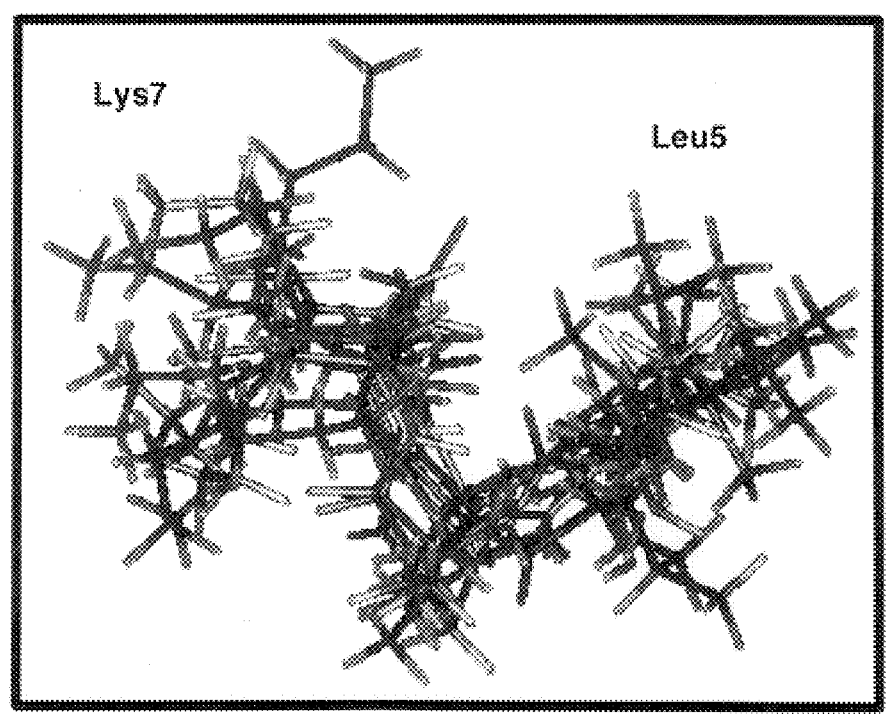

The pharmacophore of the peptides has been tentatively identified as a small hydrophobic group and a positively charged group. The gem-dimethyl and amino groups of peptide 925 are tentatively identified as the pharmacophore of this peptide as shown in FIG. 20. The hydrocarbon linkers that tether the pharmacophore groups to some scaffold have the lengths specified in FIG. 20 and the points at which these linkers are attached to the scaffold are separated by the distance specified. Finally, the dihedral angle defining the relative orientation of the two linkers was determined to be 22°.

We claim:

1. A composition for inducing specific B cell tolerance to an antiphospholipid (aPL) immunogen associated with an aPL antibody-mediated pathology comprising a conjugate of a nonimmunogenic valency platform molecule and an aPL antibody-binding analog of the immunogen that (a) is a peptide; (b) binds specifically to B cells to which the aPL immunogen binds and (c) lacks the T cell epitope(s) of the immunogen.

2. The composition of claim 1 wherein the amino acid sequence of the aPL antibody-binding analog is CLILAPDRC (SEQ ID NO:11), CLILTPDRC (SEQ ID NO:38), CLLLAPDRC (SEQ ID NO:29), CTILTLDRC (SEQ ID NO:34), CLVLALDRC (SEQ ID NO:13), CTILTPDRC (SEQ ID NO:33), CILLAHDRC (SEQ ID NO:15), CGNAADARC (SEQ ID NO:47), CTNWADPRC (SEQ ID NO:48), CGNIADPRC (SEQ ID NO:49), CTNLTDSRC (SEQ ID NO:50), CGNPTDVRC (SEQ ID NO:51), GILLNEFA (SEQ ID NO:52), GILTIDNL (SEQ ID NO:53), GILNALDYV (SEQ ID NO:54), LSDPGYVRNIFH (SEQ ID NO:55) or LTDPRYTRDISNFTD (SEQ ID NO:56).

3. The composition of claim 1 wherein the amino acid sequence of the aPL antibody-binding analog is AGPCLGVLGKLCPG (SEQ ID NO:60), GPCLGVLGKLCPG (SEQ ID NO:61), PCLGVLGKLCPG (SEQ ID NO:62), CLGVLGKLCPG (SEQ ID NO:63), AGPCLGVLGKLCG (SEQ ID NO:64) or CLGVLGKLC (SEQ ID NO:65).

4. The composition of claim 1 wherein at least one D-amino acid is substituted for a naturally-occurring L-amino acid in the peptide.

5. The composition of claim 1 wherein the analog is cyclized by a disulfide bond.

6. The composition of claim 1 wherein the analog is cyclized by a thioether bond.

7. The composition of claim 1 wherein the nonimmunogenic valency platform molecule comprises triethylene glycol.

8. The composition of claim 7 wherein the valency platform molecule comprises

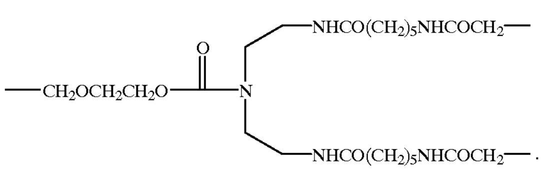

9. The composition of claim 7 wherein the valency platform molecule comprises

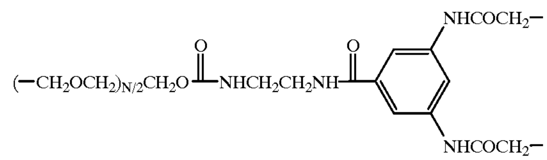

10. The composition of claim 1 wherein the nonimmunogenic valency platform molecule comprises polyethylene glycol.

11. The composition of claim 10 wherein the valency platform molecule comprises

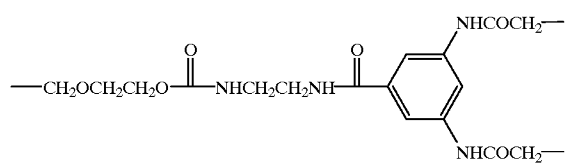

12. The composition of claim 1 wherein the nonimmunogenic valency platform molecule comprises tetraaminobenzene.

13. The composition of claim 1 wherein the nonimmunogenic valency platform molecule comprises heptaaminobetacyclodextrin.

14. The composition of claim 1 wherein the nonimmunogenic valency platform molecule comprises tetraaminopentaerythritol.

15. The composition of claim 1 wherein the nonimmunogenic valency platform molecule comprises 1,4,8,11-tetraazacyclotetradecane.

16. The composition of claim 1 wherein the nonimmunogenic valency platform molecule comprises 1,4,7,10-tetraazacyclododecane.

17. The composition of claim 1 wherein the analog contains at least one proline.

18. The composition of claim 17 wherein the peptide contains at least one α-methyl proline.

19. A method of treating an individual suffering from an antiphospholipid antibody-mediated disease comprising administering an effective amount of a composition comprising

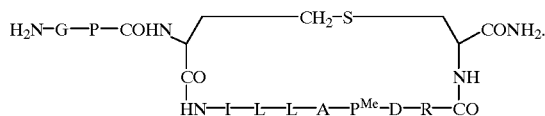

conjugated to a nonimmunogenic valency platform molecule to the individual.

20. The method of claim 19 wherein said antiphospholipid antibody-mediated disease is stroke.

21. The method of claim 19 wherein said antiphospholipid antibody-mediated disease is fetal loss.

22. The method of claim 19 wherein said antiphospholipid antibody-mediated disease is antiphospholipid antibody syndrome (APS).

23. The method of claim 19 wherein said antiphospholipid antibody-mediated disease is primary antiphospholipid antibody syndrome (PAPS).

24. The method of claim 19 wherein said antiphospholipid antibody-mediated disease is thrombosis.

25. The composition of claim 6 wherein the analog is

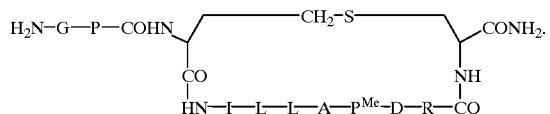

* * * * *

```
                             SEQUENCE LISTING (1) GENERAL INFORMATION:

(iii) NUMBER OF SEQUENCES: 216

(2) INFORMATION FOR SEQ ID NO:1:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Pro Cys Leu Leu Leu Ala Pro Asp Arg Cys Pro Gly
1               5                   10

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Gly Pro Cys Leu Leu Leu Ala Pro Asp Arg Cys Pro Gly
1               5                   10

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ala Gly Pro Cys Leu Leu Leu Ala Pro Asp Arg Cys Pro Gly
1               5                   10

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear
```

```
    (ii) MOLECULE TYPE: peptide (ix) FEATURE:
        (A) NAME/KEY: Modified-site
        (B) LOCATION: 3
        (D) OTHER INFORMATION: /product= "OTHER"
            /label= MeP
            /note= "alpha-methyl proline"

(xi) SEQUENCE DESCRIPTION: SEQ ID NO:4:

Ala Gly Xaa Cys Leu Leu Leu Ala Pro Asp Arg Cys Pro Gly
1               5                   10

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /product= "OTHER"
            /label= MeP
            /note= "alpha-methyl proline"

(xi) SEQUENCE DESCRIPTION: SEQ ID NO:5:

Ala Gly Pro Cys Leu Leu Leu Ala Xaa Asp Arg Cys Pro Gly
1               5                   10

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(3, 9)
        (D) OTHER INFORMATION: /product= "OTHER"
            /label= MeP
            /note= "alpha-methyl proline"

(xi) SEQUENCE DESCRIPTION: SEQ ID NO:6:

Ala Gly Xaa Cys Leu Leu Leu Ala Xaa Asp Arg Cys Pro Gly
1               5                   10

(2) INFORMATION FOR SEQ ID NO:7:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ala Gly Pro Cys Leu Leu Leu Ala Pro Asp Arg Cys Pro Gly
1               5                   10

(2) INFORMATION FOR SEQ ID NO:8:
```

```
        (i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:8:

Gly Ser Gly Ser
1

(2) INFORMATION FOR SEQ ID NO:9:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:9:

Cys Leu Leu Leu Ala Pro Asp Arg Cys
1               5

(2) INFORMATION FOR SEQ ID NO:10:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xy (details pg. 16)
            (B) CLONE: 2101

(xi) SEQUENCE DESCRIPTION: SEQ ID NO:10:

Cys Asn Ile Leu Val Leu Asp Arg Cys
1               5

(2) INFORMATION FOR SEQ ID NO:11:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz(details pg. 16)
            (B) CLONE: 5A12

(xi) SEQUENCE DESCRIPTION: SEQ ID NO:11:

Cys Leu Ile Leu Ala Pro Asp Arg Cys
1               5

(2) INFORMATION FOR SEQ ID NO:12:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz (details pg. 16)
            (B) CLONE: 2D7

(xi) SEQUENCE DESCRIPTION: SEQ ID NO:12:

Cys Leu Leu Leu Ala Pro Asp Arg Cys
1               5
```

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 3B6

(xi) SEQUENCE DESCRIPTION: SEQ ID NO:13:

Cys Leu Val Leu Ala Leu Asp Arg Cys
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 3E4

(xi) SEQUENCE DESCRIPTION: SEQ ID NO:14:

Cys Leu Phe Val Ala Leu Asp Arg Cys
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 3E7

(xi) SEQUENCE DESCRIPTION: SEQ ID NO:15:

Cys Ile Leu Leu Ala His Asp Arg Cys
1               5

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 2H1

(xi) SEQUENCE DESCRIPTION: SEQ ID NO:16:

Cys Ile Ile Leu Ala Pro Gly Arg Cys
1               5

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single

```
        (D) TOPOLOGY: linear (vii) IMMEDIATE SOURCE:
        (A) LIBRARY: xyz (details pg. 16)
        (B) CLONE: 3C10

(xi) SEQUENCE DESCRIPTION: SEQ ID NO:17:

Cys Ile Leu Leu Ala Lys Asn Arg Cys
1               5

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 3C5

(xi) SEQUENCE DESCRIPTION: SEQ ID NO:18:

Cys Ile Val Leu Val Pro Asp Arg Cys
1               5

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 2F4

(xi) SEQUENCE DESCRIPTION: SEQ ID NO:19:

Cys Leu Val Ile Ala Leu Asp Arg Cys
1               5

(2) INFORMATION FOR SEQ ID NO:20:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 5B1

(xi) SEQUENCE DESCRIPTION: SEQ ID NO:20:

Cys Trp Phe Arg Ser Gln Ser Ser Cys
1               5

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 3E11

(xi) SEQUENCE DESCRIPTION: SEQ ID NO:21:
```

```
Cys Ser Pro Ile Leu Arg Gly Asn Cys
1               5
```

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz (details pg. 16)
        (B) CLONE: 3E8

(xi) SEQUENCE DESCRIPTION: SEQ ID NO:22:

```
Cys His Lys Phe Phe Trp Leu Thr Cys
1               5
```

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z (details pg. 16)
        (B) CLONE: 2A10

(xi) SEQUENCE DESCRIPTION: SEQ ID NO:23:

```
Cys Thr Ile Leu Ala Pro Asp Arg Cys
1               5
```

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z (details pg. 16)
        (B) CLONE: 2G12

(xi) SEQUENCE DESCRIPTION: SEQ ID NO:24:

```
Cys Leu Leu Ile Thr Pro Asp Arg Cys
1               5
```

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z (details pg. 16)
        (B) CLONE: 2G11

(xi) SEQUENCE DESCRIPTION: SEQ ID NO:25:

```
Cys Leu Leu Ile Thr His Asp Arg Cys
1               5
```

(2) INFORMATION FOR SEQ ID NO:26:

```
    (i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z (details pg. 16)
        (B) CLONE: 2F10

(xi) SEQUENCE DESCRIPTION: SEQ ID NO:26:

Cys Asn Ile Leu Val Leu Asp Arg Cys
1               5

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z (details pg. 16)
        (B) CLONE: 2E3

(xi) SEQUENCE DESCRIPTION: SEQ ID NO:27:

Cys Pro Leu Ile Thr His Asp Arg Cys
1               5

(2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z (details pg. 16)
        (B) CLONE: 2D12

(xi) SEQUENCE DESCRIPTION: SEQ ID NO:28:

Cys Leu Val Leu Ala Ala Asp Arg Cys
1               5

(2) INFORMATION FOR SEQ ID NO:29:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z (details pg. 16)
        (B) CLONE: 3B10

(xi) SEQUENCE DESCRIPTION: SEQ ID NO:29:

Cys Leu Leu Ala Pro Asp Arg Cys
1               5

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
```

```
              (A) LIBRARY: xy'z (details pg. 16)
              (B) CLONE: 3F2

(xi) SEQUENCE DESCRIPTION: SEQ ID NO:30:

Cys Phe Phe His Phe Asp His Ser Cys
1               5

(2) INFORMATION FOR SEQ ID NO:31:

(i) SEQUENCE CHARACTERISTICS:
              (A) LENGTH: 9 amino acids
              (B) TYPE: amino acid
              (C) STRANDEDNESS: single
              (D) TOPOLOGY: linear (vii) IMMEDIATE SOURCE:
              (A) LIBRARY: xy'z (details pg. 16)
              (B) CLONE: 2D3

(xi) SEQUENCE DESCRIPTION: SEQ ID NO:31:

Cys Pro Leu His Thr His His Thr Cys
1               5

(2) INFORMATION FOR SEQ ID NO:32:

(i) SEQUENCE CHARACTERISTICS:
              (A) LENGTH: 9 amino acids
              (B) TYPE: amino acid
              (C) STRANDEDNESS: single
              (D) TOPOLOGY: linear (vii) IMMEDIATE SOURCE:
              (A) LIBRARY: Custom (X)6
              (B) CLONE: G11

(xi) SEQUENCE DESCRIPTION: SEQ ID NO:32:

Cys Thr Ile Leu Thr Pro Asp Arg Cys
1               5

(2) INFORMATION FOR SEQ ID NO:33:

(i) SEQUENCE CHARACTERISTICS:
              (A) LENGTH: 9 amino acids
              (B) TYPE: amino acid
              (C) STRANDEDNESS: single
              (D) TOPOLOGY: linear (vii) IMMEDIATE SOURCE:
              (A) LIBRARY: Custom (X)6
              (B) CLONE: 2H5

(xi) SEQUENCE DESCRIPTION: SEQ ID NO:33:

Cys Thr Ile Leu Thr Pro Asp Arg Cys
1               5

(2) INFORMATION FOR SEQ ID NO:34:

(i) SEQUENCE CHARACTERISTICS:
              (A) LENGTH: 9 amino acids
              (B) TYPE: amino acid
              (C) STRANDEDNESS: single
              (D) TOPOLOGY: linear (vii) IMMEDIATE SOURCE:
              (A) LIBRARY: Custom (X)6
              (B) CLONE: 2H2

(xi) SEQUENCE DESCRIPTION: SEQ ID NO:34:

Cys Thr Ile Leu Thr Leu Asp Arg Cys
1               5
```

(2) INFORMATION FOR SEQ ID NO:35:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 2H10

(xi) SEQUENCE DESCRIPTION: SEQ ID NO:35:

Cys Thr Leu Leu Thr Pro Asp Arg Cys
1               5

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 2E10

(xi) SEQUENCE DESCRIPTION: SEQ ID NO:36:

Cys Ile Gln Leu Thr Pro Asp Arg Cys
1               5

(2) INFORMATION FOR SEQ ID NO:37:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 1B7

(xi) SEQUENCE DESCRIPTION: SEQ ID NO:37:

Cys His Leu Leu Thr Pro Asp Arg Cys
1               5

(2) INFORMATION FOR SEQ ID NO:38:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 2H1

(xi) SEQUENCE DESCRIPTION: SEQ ID NO:38:

Cys Leu Ile Leu Thr Pro Asp Arg Cys
1               5

(2) INFORMATION FOR SEQ ID NO:39:

(i) SEQUENCE CHARACTERISTICS:
        (A) LENGTH: 9 amino acids
        (B) TYPE: amino acid

```
        (C) STRANDEDNESS: single
        (D) TOPOLOGY: linear (vii) IMMEDIATE SOURCE:
        (A) LIBRARY: Custom (X)6
        (B) CLONE: 2H12

(xi) SEQUENCE DESCRIPTION: SEQ ID NO:39:

Cys Ser Ile Leu Ala Pro Asp Arg Cys
1               5

(2) INFORMATION FOR SEQ ID NO:40:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 1A4

(xi) SEQUENCE DESCRIPTION: SEQ ID NO:40:

Cys Asn Leu Leu Ala Leu Asp Arg Cys
1               5

(2) INFORMATION FOR SEQ ID NO:41:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 2H6

(xi) SEQUENCE DESCRIPTION: SEQ ID NO:41:

Cys Asn Leu Leu Ala Ile Asp Arg Cys
1               5

(2) INFORMATION FOR SEQ ID NO:42:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 1C3

(xi) SEQUENCE DESCRIPTION: SEQ ID NO:42:

Cys Leu Leu Leu Ala Ile Asp Arg Cys
1               5

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 1D10
```

```
       (xi) SEQUENCE DESCRIPTION: SEQ ID NO:43:

Cys Thr Ile Ile Thr Gln Asp Arg Cys
1               5

(2) INFORMATION FOR SEQ ID NO:44:

(i) SEQUENCE CHARACTERISTICS:
         (A) LENGTH: 9 amino acids
         (B) TYPE: amino acid
         (C) STRANDEDNESS: single
         (D) TOPOLOGY: linear (vii) IMMEDIATE SOURCE:
         (A) LIBRARY: Custom (X)6
         (B) CLONE: 2H4

(xi) SEQUENCE DESCRIPTION: SEQ ID NO:44:

Cys Asn Ile Ile Thr Arg Asp Arg Cys
1               5

(2) INFORMATION FOR SEQ ID NO:45:

(i) SEQUENCE CHARACTERISTICS:
         (A) LENGTH: 9 amino acids
         (B) TYPE: amino acid
         (C) STRANDEDNESS: single
         (D) TOPOLOGY: linear (vii) IMMEDIATE SOURCE:
         (A) LIBRARY: Custom (X)6
         (B) CLONE: 2G12

(xi) SEQUENCE DESCRIPTION: SEQ ID NO:45:

Cys Ile Leu His Ala Ala His Arg Cys
1               5

(2) INFORMATION FOR SEQ ID NO:46:

(i) SEQUENCE CHARACTERISTICS:
         (A) LENGTH: 9 amino acids
         (B) TYPE: amino acid
         (C) STRANDEDNESS: single
         (D) TOPOLOGY: linear (vii) IMMEDIATE SOURCE:
         (A) LIBRARY: Custom (X)6
         (B) CLONE: 1A9

(xi) SEQUENCE DESCRIPTION: SEQ ID NO:46:

Cys Ser Ser Lys Ser Tyr Trp Arg Cys
1               5

(2) INFORMATION FOR SEQ ID NO:47:

(i) SEQUENCE CHARACTERISTICS:
         (A) LENGTH: 9 amino acids
         (B) TYPE: amino acid
         (C) STRANDEDNESS: single
         (D) TOPOLOGY: linear (vii) IMMEDIATE SOURCE:
         (A) LIBRARY: xy'z (details pg. 16)
         (B) CLONE: 4B11

(xi) SEQUENCE DESCRIPTION: SEQ ID NO:47:

Cys Gly Asn Ala Ala Asp Ala Arg Cys
1               5

(2) INFORMATION FOR SEQ ID NO:48:
```

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xy'z (details pg. 16)
            (B) CLONE: 4D3

(xi) SEQUENCE DESCRIPTION: SEQ ID NO:48:

Cys Thr Asn Trp Ala Asp Pro Arg Cys
1               5

(2) INFORMATION FOR SEQ ID NO:49:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xy'z (details pg. 16)
            (B) CLONE: 4C7

(xi) SEQUENCE DESCRIPTION: SEQ ID NO:49:

Cys Gly Asn Ile Ala Asp Pro Arg Cys
1               5

(2) INFORMATION FOR SEQ ID NO:50:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xy'z (details pg. 16)
            (B) CLONE: 4G7

(xi) SEQUENCE DESCRIPTION: SEQ ID NO:50:

Cys Thr Asn Leu Thr Asp Ser Arg Cys
1               5

(2) INFORMATION FOR SEQ ID NO:51:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xy'z (details pg. 16)
            (B) CLONE: 4A2

(xi) SEQUENCE DESCRIPTION: SEQ ID NO:51:

Cys Gly Asn Pro Thr Asp Val Arg Cys
1               5

(2) INFORMATION FOR SEQ ID NO:52:

(i) SEQUENCE CHARACTERISTICS:
            (A) LENGTH: 8 amino acids
            (B) TYPE: amino acid
            (C) STRANDEDNESS: single
            (D) TOPOLOGY: linear

```
    (xi) SEQUENCE DESCRIPTION: SEQ ID NO:52:

Gly Ile Leu Leu Asn Glu Phe Ala
1               5

(2) INFORMATION FOR SEQ ID NO:53:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:53:

Gly Ile Leu Thr Ile Asp Asn Leu
1               5

(2) INFORMATION FOR SEQ ID NO:54:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:54:

Gly Ile Leu Ala Leu Asp Tyr Val
1               5

(2) INFORMATION FOR SEQ ID NO:55:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:55:

Leu Ser Asp Pro Gly Tyr Val Arg Asn Ile Phe His
1               5                   10

(2) INFORMATION FOR SEQ ID NO:56:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:56:

Leu Thr Asp Pro Arg Tyr Thr Arg Asp Ile Ser Asn Phe Thr Asp
1               5                   10                  15

(2) INFORMATION FOR SEQ ID NO:57:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Ala Gly Pro Cys Leu Gly Val Leu Gly Lys Leu Cys Pro Gly
1               5                   10

(2) INFORMATION FOR SEQ ID NO:58:
```

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:58:

Cys Leu Gly Val Leu Gly Lys Leu Cys
1               5

(2) INFORMATION FOR SEQ ID NO:59:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

Cys Leu Ile Leu Ala Pro Asp Arg Cys
1               5

(2) INFORMATION FOR SEQ ID NO:60:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

Ala Gly Pro Cys Leu Gly Val Leu Gly Lys Leu Cys Pro Gly
1               5                   10

(2) INFORMATION FOR SEQ ID NO:61:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

Gly Pro Cys Leu Gly Val Leu Gly Lys Leu Cys Pro Gly
1               5                   10

(2) INFORMATION FOR SEQ ID NO:62:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

Pro Cys Leu Gly Val Leu Gly Lys Leu Cys Pro Gly
1               5                   10

(2) INFORMATION FOR SEQ ID NO:63:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Cys Leu Gly Val Leu Gly Lys Leu Cys Pro Gly
1               5                   10

(2) INFORMATION FOR SEQ ID NO:64:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Ala Gly Pro Cys Leu Gly Val Leu Gly Lys Leu Cys Gly
1               5                   10

(2) INFORMATION FOR SEQ ID NO:65:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

Cys Leu Gly Val Leu Gly Lys Leu Cys
1               5

(2) INFORMATION FOR SEQ ID NO:66:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Cys Leu Gly Val Leu Gly Lys Leu Cys
1               5

(2) INFORMATION FOR SEQ ID NO:67:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc

```
            /note= "Homocysteine"

(xi) SEQUENCE DESCRIPTION: SEQ ID NO:67:

Xaa Leu Gly Val Leu Gly Lys Leu Cys
1               5

(2) INFORMATION FOR SEQ ID NO:68:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /product= "OTHER"
            /label= Hc
            /note= "Homocysteine"

(xi) SEQUENCE DESCRIPTION: SEQ ID NO:68:

Cys Leu Gly Val Leu Gly Lys Leu Xaa
1               5

(2) INFORMATION FOR SEQ ID NO:69:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(1, 9)
        (D) OTHER INFORMATION: /product= "OTHER"
            /label= Hc
            /note= "Homocysteine"

(xi) SEQUENCE DESCRIPTION: SEQ ID NO:69:

Xaa Leu Gly Val Leu Gly Lys Leu Xaa
1               5

(2) INFORMATION FOR SEQ ID NO:70:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

Cys Ala Gly Val Leu Gly Lys Leu Cys
1               5

(2) INFORMATION FOR SEQ ID NO:71:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO:71:

Cys Leu Ala Val Leu Gly Lys Leu Cys
1               5

(2) INFORMATION FOR SEQ ID NO:72:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

Cys Leu Gly Ala Leu Gly Lys Leu Cys
1               5

(2) INFORMATION FOR SEQ ID NO:73:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

Cys Leu Gly Val Ala Gly Lys Leu Cys
1               5

(2) INFORMATION FOR SEQ ID NO:74:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

Cys Leu Gly Val Leu Ala Lys Leu Cys
1               5

(2) INFORMATION FOR SEQ ID NO:75:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Cys Leu Gly Val Leu Gly Ala Leu Cys
1               5

(2) INFORMATION FOR SEQ ID NO:76:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

Cys Leu Gly Val Leu Gly Lys Ala Cys
1               5

(2) INFORMATION FOR SEQ ID NO:77:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Cys Gly Gly Val Leu Gly Lys Leu Cys
1               5

(2) INFORMATION FOR SEQ ID NO:78:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

Cys Leu Gly Gly Leu Gly Lys Leu Cys
1               5

(2) INFORMATION FOR SEQ ID NO:79:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

Cys Leu Gly Val Gly Gly Lys Leu Cys
1               5

(2) INFORMATION FOR SEQ ID NO:80:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

Cys Leu Gly Val Leu Gly Gly Leu Cys
1               5

(2) INFORMATION FOR SEQ ID NO:81:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

Cys Leu Gly Val Leu Gly Lys Gly Cys
1               5

(2) INFORMATION FOR SEQ ID NO:82:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:82:

Cys Ile Gly Val Leu Gly Lys Leu Cys
1               5

(2) INFORMATION FOR SEQ ID NO:83:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:83:

Cys Val Gly Val Leu Gly Lys Leu Cys
1               5

(2) INFORMATION FOR SEQ ID NO:84:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:84:

Cys Met Gly Val Leu Gly Lys Leu Cys
1               5

(2) INFORMATION FOR SEQ ID NO:85:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /label= Cy
                /note= "cyclohexyl alanine"

(xi) SEQUENCE DESCRIPTION: SEQ ID NO:85:

Cys Xaa Gly Val Leu Gly Lys Leu Cys
1               5

(2) INFORMATION FOR SEQ ID NO:86:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= tL
            /note= "tertiary leucine"

(xi) SEQUENCE DESCRIPTION: SEQ ID NO:86:

Cys Xaa Gly Val Leu Gly Lys Leu Cys
1            5

(2) INFORMATION FOR SEQ ID NO:87:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= mL
            /note= "alpha-methyl leucine"

(xi) SEQUENCE DESCRIPTION: SEQ ID NO:87:

Cys Xaa Gly Val Leu Gly Lys Leu Cys
1            5

(2) INFORMATION FOR SEQ ID NO:88:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= Iv
            /note= "alpha-methyl, alpha amino butyric acid"

(xi) SEQUENCE DESCRIPTION: SEQ ID NO:88:

Cys Xaa Gly Val Leu Gly Lys Leu Cys
1            5

(2) INFORMATION FOR SEQ ID NO:89:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:89:

Cys Leu Gly Leu Leu Gly Lys Leu Cys
1               5

(2) INFORMATION FOR SEQ ID NO:90:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:90:

Cys Leu Gly Ile Leu Gly Lys Leu Cys
1               5

(2) INFORMATION FOR SEQ ID NO:91:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:91:

Cys Leu Gly Met Leu Gly Lys Leu Cys
1               5

(2) INFORMATION FOR SEQ ID NO:92:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= Cy
            /note= "homocysteine"

(xi) SEQUENCE DESCRIPTION: SEQ ID NO:92:

Cys Leu Gly Xaa Leu Gly Lys Leu Cys
1               5

(2) INFORMATION FOR SEQ ID NO:93:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= tL
            /note= "tertiary leucine"

(xi) SEQUENCE DESCRIPTION: SEQ ID NO:93:

Cys Leu Gly Xaa Leu Gly Lys Leu Cys
1               5

(2) INFORMATION FOR SEQ ID NO:94:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= mL
            /note= "alpha-methyl leucine"

(xi) SEQUENCE DESCRIPTION: SEQ ID NO:94:

Cys Leu Gly Xaa Leu Gly Lys Leu Cys
1               5

(2) INFORMATION FOR SEQ ID NO:95:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= Iv
            /note= "alpha-methyl, alpha-amino butyric acid"

(xi) SEQUENCE DESCRIPTION: SEQ ID NO:95:

Cys Leu Gly Xaa Leu Gly Lys Leu Cys
1               5

(2) INFORMATION FOR SEQ ID NO:96:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

Cys Leu Gly Val Ile Gly Lys Leu Cys
1               5

(2) INFORMATION FOR SEQ ID NO:97:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

```
Cys Leu Gly Val Val Gly Lys Leu Cys
1               5
```

(2) INFORMATION FOR SEQ ID NO:98:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

```
Cys Leu Gly Val Met Gly Lys Leu Cys
1               5
```

(2) INFORMATION FOR SEQ ID NO:99:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= Cy
            /note= "homocysteine"

(xi) SEQUENCE DESCRIPTION: SEQ ID NO:99:

```
Cys Leu Gly Val Xaa Gly Lys Leu Cys
1               5
```

(2) INFORMATION FOR SEQ ID NO:100:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= tL
            /note= "tertiary leucine"

(xi) SEQUENCE DESCRIPTION: SEQ ID NO:100:

```
Cys Leu Gly Val Xaa Gly Lys Leu Cys
1               5
```

(2) INFORMATION FOR SEQ ID NO:101:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site (B) LOCATION: 5
            (D) OTHER INFORMATION: /product= "OTHER"
                /label= mL
                /note= "alpha-methyl leucine"

(xi) SEQUENCE DESCRIPTION: SEQ ID NO:101:

Cys Leu Gly Val Xaa Gly Lys Leu Cys
1               5

(2) INFORMATION FOR SEQ ID NO:102:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= Iv
            /note= "alpha-methyl, alpha-amino butyric acid"

(xi) SEQUENCE DESCRIPTION: SEQ ID NO:102:

Cys Leu Gly Val Xaa Gly Lys Leu Cys
1               5

(2) INFORMATION FOR SEQ ID NO:103:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

Cys Leu Gly Val Leu Gly Lys Ile Cys
1               5

(2) INFORMATION FOR SEQ ID NO:104:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

Cys Leu Gly Val Leu Gly Lys Val Cys
1               5

(2) INFORMATION FOR SEQ ID NO:105:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Cys Leu Gly Val Leu Gly Lys Met Cys

```
1               5

(2) INFORMATION FOR SEQ ID NO:106:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= Cy
            /note= "homocysteine"

(xi) SEQUENCE DESCRIPTION: SEQ ID NO:106:

Cys Leu Gly Val Leu Gly Lys Xaa Cys
1               5

(2) INFORMATION FOR SEQ ID NO:107:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= tL
            /note= "tertiary leucine"

(xi) SEQUENCE DESCRIPTION: SEQ ID NO:107:

Cys Leu Gly Val Leu Gly Lys Xaa Cys
1               5

(2) INFORMATION FOR SEQ ID NO:108:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= mL
            /note= "alpha-methyl leucine"

(xi) SEQUENCE DESCRIPTION: SEQ ID NO:108:

Cys Leu Gly Val Leu Gly Lys Xaa Cys
1               5

(2) INFORMATION FOR SEQ ID NO:109:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

(ii) MOLECULE TYPE: peptide (ix) FEATURE:
            (A) NAME/KEY: Modified-site
            (B) LOCATION: 8
            (D) OTHER INFORMATION: /product= "OTHER"
                /label= Iv
                /note= "alpha-methyl, alpha-amino butyric acid"

(xi) SEQUENCE DESCRIPTION: SEQ ID NO:109:

Cys Leu Gly Val Leu Gly Lys Xaa Cys
1               5

(2) INFORMATION FOR SEQ ID NO:110:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:110:

Cys Leu Pro Val Leu Gly Lys Leu Cys
1               5

(2) INFORMATION FOR SEQ ID NO:111:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "OTHER"
                /label= mP
                /note= "alpha-methyl proline"

(xi) SEQUENCE DESCRIPTION: SEQ ID NO:111:

Cys Leu Xaa Val Leu Gly Lys Leu Cys
1               5

(2) INFORMATION FOR SEQ ID NO:112:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "OTHER"
                /label= mA
                /note= "alpha-methyl alanine"

(xi) SEQUENCE DESCRIPTION: SEQ ID NO:112:

Cys Leu Xaa Val Leu Gly Lys Leu Cys
1               5

(2) INFORMATION FOR SEQ ID NO:113:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= cG
            /note= "cyclo-propyl glycine"

(xi) SEQUENCE DESCRIPTION: SEQ ID NO:113:

Cys Leu Xaa Val Leu Gly Lys Leu Cys
1               5

(2) INFORMATION FOR SEQ ID NO:114:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:114:

Cys Leu Gly Val Leu Pro Lys Leu Cys
1               5

(2) INFORMATION FOR SEQ ID NO:115:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= mP
            /note= "alpha-methyl proline"

(xi) SEQUENCE DESCRIPTION: SEQ ID NO:115:

Cys Leu Gly Val Leu Xaa Lys Leu Cys
1               5

(2) INFORMATION FOR SEQ ID NO:116:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= mA
            /note= "alpha-methyl alanine"

(xi) SEQUENCE DESCRIPTION: SEQ ID NO:116:

```
Cys Leu Gly Val Leu Xaa Lys Leu Cys
1               5
```

(2) INFORMATION FOR SEQ ID NO:117:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= cG
            /note= "cyclopropyl glycine"

(xi) SEQUENCE DESCRIPTION: SEQ ID NO:117:

```
Cys Leu Gly Val Leu Xaa Lys Leu Cys
1               5
```

(2) INFORMATION FOR SEQ ID NO:118:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= dA
            /note= "D-alanine"

(xi) SEQUENCE DESCRIPTION: SEQ ID NO:118:

```
Cys Leu Xaa Val Leu Gly Lys Leu Cys
1               5
```

(2) INFORMATION FOR SEQ ID NO:119:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= dA
            /note= "D-alanine"

(xi) SEQUENCE DESCRIPTION: SEQ ID NO:119:

```
Cys Leu Gly Val Leu Xaa Lys Leu Cys
1               5
```

(2) INFORMATION FOR SEQ ID NO:120:

(i) SEQUENCE CHARACTERISTICS:
        (A) LENGTH: 9 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO:120:

Cys Pro Gly Val Leu Gly Lys Leu Cys
1               5

(2) INFORMATION FOR SEQ ID NO:121:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:121:

Cys Leu Pro Val Leu Gly Lys Leu Cys
1               5

(2) INFORMATION FOR SEQ ID NO:122:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:122:

Cys Leu Gly Pro Leu Gly Lys Leu Cys
1               5

(2) INFORMATION FOR SEQ ID NO:123:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:123:

Cys Leu Gly Val Pro Gly Lys Leu Cys
1               5

(2) INFORMATION FOR SEQ ID NO:124:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:124:

Cys Leu Gly Val Leu Pro Lys Leu Cys
1               5

(2) INFORMATION FOR SEQ ID NO:125:

(i) SEQUENCE CHARACTERISTICS:
            (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:125:

Cys Leu Gly Val Leu Gly Pro Leu Cys
1               5

(2) INFORMATION FOR SEQ ID NO:126:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:126:

Cys Leu Gly Val Leu Gly Lys Pro Cys
1               5

(2) INFORMATION FOR SEQ ID NO:127:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /label= pG
                /note= "phenylglycine"

(xi) SEQUENCE DESCRIPTION: SEQ ID NO:127:

Cys Xaa Gly Val Leu Gly Lys Leu Cys
1               5

(2) INFORMATION FOR SEQ ID NO:128:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "OTHER"
                /label= pG
                /note= "phenylglcine"

(xi) SEQUENCE DESCRIPTION: SEQ ID NO:128:

Cys Leu Xaa Val Leu Gly Lys Leu Cys
1               5

(2) INFORMATION FOR SEQ ID NO:129:

(i) SEQUENCE CHARACTERISTICS:
            (A) LENGTH: 9 amino acids
            (B) TYPE: amino acid
```

```
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /product= "OTHER"
                /label= pG
                /note= "phenylglycine"

(xi) SEQUENCE DESCRIPTION: SEQ ID NO:129:

Cys Leu Gly Xaa Leu Gly Lys Leu Cys
1               5

(2) INFORMATION FOR SEQ ID NO:130:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 5
            (D) OTHER INFORMATION: /product= "OTHER"
                /label= pG
                /note= "phenylglycine"

(xi) SEQUENCE DESCRIPTION: SEQ ID NO:130:

Cys Leu Gly Val Xaa Gly Lys Leu Cys
1               5

(2) INFORMATION FOR SEQ ID NO:131:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 6
            (D) OTHER INFORMATION: /product= "OTHER"
                /label= pG
                /note= "phenylglycine"

(xi) SEQUENCE DESCRIPTION: SEQ ID NO:131:

Cys Leu Gly Val Leu Xaa Lys Leu Cys
1               5

(2) INFORMATION FOR SEQ ID NO:132:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /product= "OTHER"
                /label= pG
```

/note= "phenylglycine"

(xi) SEQUENCE DESCRIPTION: SEQ ID NO:132:

Cys Leu Gly Val Leu Gly Xaa Leu Cys
1               5

(2) INFORMATION FOR SEQ ID NO:133:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= pG
            /note= "phenylglycine"

(xi) SEQUENCE DESCRIPTION: SEQ ID NO:133:

Cys Leu Gly Val Leu Gly Lys Xaa Cys
1               5

(2) INFORMATION FOR SEQ ID NO:134:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "Aib"

(xi) SEQUENCE DESCRIPTION: SEQ ID NO:134:

Cys Xaa Gly Val Leu Gly Lys Leu Cys
1               5

(2) INFORMATION FOR SEQ ID NO:135:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Aib"

(xi) SEQUENCE DESCRIPTION: SEQ ID NO:135:

Cys Leu Xaa Val Leu Gly Lys Leu Cys
1               5

(2) INFORMATION FOR SEQ ID NO:136:

(i) SEQUENCE CHARACTERISTICS:
        (A) LENGTH: 9 amino acids
        (B) TYPE: amino acid
        (C) STRANDEDNESS: single (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "Aib"

(xi) SEQUENCE DESCRIPTION: SEQ ID NO:136:

Cys Leu Gly Xaa Leu Gly Lys Leu Cys
1               5

(2) INFORMATION FOR SEQ ID NO:137:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "Aib"

(xi) SEQUENCE DESCRIPTION: SEQ ID NO:137:

Cys Leu Gly Val Xaa Gly Lys Leu Cys
1               5

(2) INFORMATION FOR SEQ ID NO:138:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "Aib"

(xi) SEQUENCE DESCRIPTION: SEQ ID NO:138:

Cys Leu Gly Val Leu Xaa Lys Leu Cys
1               5

(2) INFORMATION FOR SEQ ID NO:139:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "Aib"

(xi) SEQUENCE DESCRIPTION: SEQ ID NO:139:

Cys Leu Gly Val Leu Gly Xaa Leu Cys
1               5

(2) INFORMATION FOR SEQ ID NO:140:

```
        (i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 8
            (D) OTHER INFORMATION: /product= "Aib"

(xi) SEQUENCE DESCRIPTION: SEQ ID NO:140:

Cys Leu Gly Val Leu Gly Lys Xaa Cys
1               5

(2) INFORMATION FOR SEQ ID NO:141:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:141:

Cys Leu Gly Val Leu Gly Arg Leu Cys
1               5

(2) INFORMATION FOR SEQ ID NO:142:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /product= "Orn"

(xi) SEQUENCE DESCRIPTION: SEQ ID NO:142:

Cys Leu Gly Val Leu Gly Xaa Leu Cys
1               5

(2) INFORMATION FOR SEQ ID NO:143:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /product= "OTHER"
                /label= mK
                /note= "N-epsilon-methyl lysine"

(xi) SEQUENCE DESCRIPTION: SEQ ID NO:143:

Cys Leu Gly Val Leu Gly Xaa Leu Cys
1               5
```

(2) INFORMATION FOR SEQ ID NO:144:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= dP
            /note= "D-proline"

(xi) SEQUENCE DESCRIPTION: SEQ ID NO:144:

```
Xaa Cys Leu Gly Val Leu Gly Lys Leu Cys
1               5                   10
```

(2) INFORMATION FOR SEQ ID NO:145:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= dL
            /note= "D-leucine"

(xi) SEQUENCE DESCRIPTION: SEQ ID NO:145:

```
Cys Xaa Gly Val Leu Gly Lys Leu Cys
1               5
```

(2) INFORMATION FOR SEQ ID NO:146:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= dV
            /note= "D-valine"

(xi) SEQUENCE DESCRIPTION: SEQ ID NO:146:

```
Cys Leu Gly Xaa Leu Gly Lys Leu Cys
1               5
```

(2) INFORMATION FOR SEQ ID NO:147:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Modified-site
         (B) LOCATION: 5
         (D) OTHER INFORMATION: /product= "OTHER"
             /label= dL
             /note= "D-leucine"

(xi) SEQUENCE DESCRIPTION: SEQ ID NO:147:

Cys Leu Gly Val Xaa Gly Lys Leu Cys
1               5

(2) INFORMATION FOR SEQ ID NO:148:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 7
         (D) OTHER INFORMATION: /product= "OTHER"
             /label= dK
             /note= "D-lysine"

(xi) SEQUENCE DESCRIPTION: SEQ ID NO:148:

Cys Leu Gly Val Leu Gly Xaa Leu Cys
1               5

(2) INFORMATION FOR SEQ ID NO:149:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 8
         (D) OTHER INFORMATION: /product= "OTHER"
             /label= dL
             /note= "D-leucine"

(xi) SEQUENCE DESCRIPTION: SEQ ID NO:149:

Cys Leu Gly Val Leu Gly Lys Xaa Cys
1               5

(2) INFORMATION FOR SEQ ID NO:150:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /label= dL
             /note= "D-leucine"

(ix) FEATURE:
         (A) NAME/KEY: Modified-site
```

(B) LOCATION: 4
        (D) OTHER INFORMATION: /product= "OTHER"
            /label= dV
            /note= "D-valine"

(xi) SEQUENCE DESCRIPTION: SEQ ID NO:150:

Cys Xaa Gly Xaa Leu Gly Lys Leu Cys
1               5

(2) INFORMATION FOR SEQ ID NO:151:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(2, 4)
        (D) OTHER INFORMATION: /product= "OTHER"
            /label= dV
            /note= "D-valine"

(xi) SEQUENCE DESCRIPTION: SEQ ID NO:151:

Cys Xaa Gly Xaa Leu Gly Lys Leu Cys
1               5

(2) INFORMATION FOR SEQ ID NO:152:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(2, 4)
        (D) OTHER INFORMATION: /product= "OTHER"
            /label= dL
            /note= "D-leucine"

(xi) SEQUENCE DESCRIPTION: SEQ ID NO:152:

Cys Xaa Gly Xaa Leu Gly Lys Leu Cys
1               5

(2) INFORMATION FOR SEQ ID NO:153:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= dV
            /note= "D-valine"

(ix) FEATURE:
        (A) NAME/KEY: Modified-site
        (B) LOCATION: 5
        (D) OTHER INFORMATION: /product= "OTHER"
            /label= dL /note= "D-leucine"

(xi) SEQUENCE DESCRIPTION: SEQ ID NO:153:

Cys Leu Gly Xaa Xaa Gly Lys Leu Cys
1               5

(2) INFORMATION FOR SEQ ID NO:154:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= dV
            /note= "D-valine"

(ix) FEATURE:
        (A) NAME/KEY: Modified-site
        (B) LOCATION: 4
        (D) OTHER INFORMATION: /product= "OTHER"
            /label= dL
            /note= "D-leucine"

(xi) SEQUENCE DESCRIPTION: SEQ ID NO:154:

Cys Leu Gly Xaa Xaa Gly Lys Leu Cys
1               5

(2) INFORMATION FOR SEQ ID NO:155:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(4, 5)
        (D) OTHER INFORMATION: /product= "OTHER"
            /label= dV
            /note= "D-valine"

(xi) SEQUENCE DESCRIPTION: SEQ ID NO:155:

Cys Leu Gly Xaa Xaa Gly Lys Leu Cys
1               5

(2) INFORMATION FOR SEQ ID NO:156:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(4, 5)
        (D) OTHER INFORMATION: /product= "OTHER"
            /label= dL
            /note= "D-leucine"

(xi) SEQUENCE DESCRIPTION: SEQ ID NO:156:

```
Cys Leu Gly Xaa Xaa Gly Lys Leu Cys
1               5
```

(2) INFORMATION FOR SEQ ID NO:157:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= dL
            /note= "D-leucine"

(ix) FEATURE:
        (A) NAME/KEY: Modified-site
        (B) LOCATION: 7
        (D) OTHER INFORMATION: /product= "OTHER"
            /label= dK
            /note= "D-lysine"

(xi) SEQUENCE DESCRIPTION: SEQ ID NO:157:

```
Cys Leu Gly Val Xaa Gly Xaa Leu Cys
1               5
```

(2) INFORMATION FOR SEQ ID NO:158:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /label= dL
            /note= "D-leucine"

(ix) FEATURE:
        (A) NAME/KEY: Modified-site
        (B) LOCATION: 5
        (D) OTHER INFORMATION: /product= "OTHER"
            /label= dK
            /note= "D-lysine"

(xi) SEQUENCE DESCRIPTION: SEQ ID NO:158:

```
Cys Leu Gly Val Xaa Gly Xaa Leu Cys
1               5
```

(2) INFORMATION FOR SEQ ID NO:159:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(5, 7)
        (D) OTHER INFORMATION: /product= "OTHER"

```
            /label= dL
            /note= "D-leucine"

(xi) SEQUENCE DESCRIPTION: SEQ ID NO:159:

Cys Leu Gly Val Xaa Gly Xaa Leu Cys
1               5

(2) INFORMATION FOR SEQ ID NO:160:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(5, 7)
        (D) OTHER INFORMATION: /product= "OTHER"
            /label= dK
            /note= "D-lysine"

(xi) SEQUENCE DESCRIPTION: SEQ ID NO:160:

Cys Leu Gly Val Xaa Gly Xaa Leu Cys
1               5

(2) INFORMATION FOR SEQ ID NO:161:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /label= dK
            /note= "D-lysine"

(ix) FEATURE:
        (A) NAME/KEY: Modified-site
        (B) LOCATION: 8
        (D) OTHER INFORMATION: /product= "OTHER"
            /label= dL
            /note= "D-leucine"

(xi) SEQUENCE DESCRIPTION: SEQ ID NO:161:

Cys Leu Gly Val Leu Gly Xaa Xaa Cys
1               5

(2) INFORMATION FOR SEQ ID NO:162:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= dK
            /note= "D-lysine"
```

```
    (ix) FEATURE:
         (A) NAME/KEY: Modified-site
         (B) LOCATION: 7
         (D) OTHER INFORMATION: /product= "OTHER"
             /label= dL
             /note= "D-leucine"

(xi) SEQUENCE DESCRIPTION: SEQ ID NO:162:

Cys Leu Gly Val Leu Gly Xaa Xaa Cys
1               5

(2) INFORMATION FOR SEQ ID NO:163:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: group(7, 8)
         (D) OTHER INFORMATION: /product= "OTHER"
             /label= dK
             /note= "D-lysine"

(xi) SEQUENCE DESCRIPTION: SEQ ID NO:163:

Cys Leu Gly Val Leu Gly Xaa Xaa Cys
1               5

(2) INFORMATION FOR SEQ ID NO:164:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: group(7, 8)
         (D) OTHER INFORMATION: /product= "OTHER"
             /label= dL
             /note= "D-leucine"

(xi) SEQUENCE DESCRIPTION: SEQ ID NO:164:

Cys Leu Gly Val Leu Gly Xaa Xaa Cys
1               5

(2) INFORMATION FOR SEQ ID NO:165:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 6
         (D) OTHER INFORMATION: /product= "OTHER"
             /label= dA
             /note= "D-alanine"

(xi) SEQUENCE DESCRIPTION: SEQ ID NO:165:

Cys Leu Gly Val Leu Xaa Lys Leu Cys
```

1          5

(2) INFORMATION FOR SEQ ID NO:166:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /product= "OTHER"
            /label= dC
            /note= "D-cysteine"

(xi) SEQUENCE DESCRIPTION: SEQ ID NO:166:

Cys Leu Gly Val Leu Gly Lys Leu Xaa
1               5

(2) INFORMATION FOR SEQ ID NO:167:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= nC
            /note= "N-alpha-methyl cysteine"

(xi) SEQUENCE DESCRIPTION: SEQ ID NO:167:

Xaa Leu Gly Val Leu Gly Lys Leu Cys
1               5

(2) INFORMATION FOR SEQ ID NO:168:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= nL
            /note= "N-alpha-methyl leucine"

(xi) SEQUENCE DESCRIPTION: SEQ ID NO:168:

Cys Xaa Gly Val Leu Gly Lys Leu Cys
1               5

(2) INFORMATION FOR SEQ ID NO:169:

(i) SEQUENCE CHARACTERISTICS:
        (A) LENGTH: 9 amino acids
        (B) TYPE: amino acid
        (C) STRANDEDNESS: single
        (D) TOPOLOGY: linear

```
    (ii) MOLECULE TYPE: peptide (ix) FEATURE:
         (A) NAME/KEY: Modified-site
         (B) LOCATION: 3
         (D) OTHER INFORMATION: /product= "OTHER"
             /label= nG
             /note= "N-methyl glycine"

(xi) SEQUENCE DESCRIPTION: SEQ ID NO:169:

Cys Leu Xaa Val Leu Gly Lys Leu Cys
1               5

(2) INFORMATION FOR SEQ ID NO:170:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 4
         (D) OTHER INFORMATION: /product= "OTHER"
             /label= nV
             /note= "N-alpha-methyl valine"

(xi) SEQUENCE DESCRIPTION: SEQ ID NO:170:

Cys Leu Gly Xaa Leu Gly Lys Leu Cys
1               5

(2) INFORMATION FOR SEQ ID NO:171:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 5
         (D) OTHER INFORMATION: /product= "OTHER"
             /label= nL
             /note= "N-alpha-methyl leucine"

(xi) SEQUENCE DESCRIPTION: SEQ ID NO:171:

Cys Leu Gly Val Xaa Gly Lys Leu Cys
1               5

(2) INFORMATION FOR SEQ ID NO:172:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 6
         (D) OTHER INFORMATION: /product= "OTHER"
             /label= nG
             /note= "N-methyl glycine"
```

```
    (xi) SEQUENCE DESCRIPTION: SEQ ID NO:172:

Cys Leu Gly Val Leu Xaa Lys Leu Cys
1               5

(2) INFORMATION FOR SEQ ID NO:173:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /label= nK
            /note= "N-alpha-methyl lysine"

(xi) SEQUENCE DESCRIPTION: SEQ ID NO:173:

Cys Leu Gly Val Leu Gly Xaa Leu Cys
1               5

(2) INFORMATION FOR SEQ ID NO:174:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= nL
            /note= "N-alpha-methyl leucine"

(xi) SEQUENCE DESCRIPTION: SEQ ID NO:174:

Cys Leu Gly Val Leu Gly Lys Xaa Cys
1               5

(2) INFORMATION FOR SEQ ID NO:175:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /product= "OTHER"
            /label= nC
            /note= "N-alpha-methyl cysteine"

(xi) SEQUENCE DESCRIPTION: SEQ ID NO:175:

Cys Leu Gly Val Leu Gly Lys Leu Xaa
1               5

(2) INFORMATION FOR SEQ ID NO:176:

(i) SEQUENCE CHARACTERISTICS:
        (A) LENGTH: 9 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:176:

Cys Leu Gly Val Leu Gly Lys Leu Cys
1               5

(2) INFORMATION FOR SEQ ID NO:177:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:177:

Cys Leu Gly Val Leu Gly Lys Leu Cys
1               5

(2) INFORMATION FOR SEQ ID NO:178:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:178:

Cys Leu Gly Val Leu Gly Lys Leu Cys
1               5

(2) INFORMATION FOR SEQ ID NO:179:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 9
            (D) OTHER INFORMATION: /product= "OTHER"
                /label= dC
                /note= "D-cysteine"

(xi) SEQUENCE DESCRIPTION: SEQ ID NO:179:

Cys Leu Gly Val Leu Gly Lys Leu Xaa
1               5

(2) INFORMATION FOR SEQ ID NO:180:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site

```
            (B) LOCATION: 1
            (D) OTHER INFORMATION: /product= "OTHER"
                /label= dC
                /note= "D-cysteine"

(xi) SEQUENCE DESCRIPTION: SEQ ID NO:180:

Xaa Leu Gly Val Leu Gly Lys Leu Cys
1               5

(2) INFORMATION FOR SEQ ID NO:181:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(1, 9)
        (D) OTHER INFORMATION: /product= "OTHER"
            /label= dC
            /note= "D-cysteine"

(xi) SEQUENCE DESCRIPTION: SEQ ID NO:181:

Xaa Leu Gly Val Leu Gly Lys Leu Xaa
1               5

(2) INFORMATION FOR SEQ ID NO:182:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:182:

Xaa Leu Gly Val Leu Ala Lys Leu Cys
1               5

(2) INFORMATION FOR SEQ ID NO:183:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:183:

Xaa Gly Val Leu Ala Lys Leu Cys
1               5
```

(2) INFORMATION FOR SEQ ID NO:184:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:184:

Xaa Leu Val Leu Ala Lys Leu Cys
1            5

(2) INFORMATION FOR SEQ ID NO:185:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:185:

Xaa Leu Gly Leu Ala Lys Leu Cys
1            5

(2) INFORMATION FOR SEQ ID NO:186:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:186:

Xaa Leu Gly Val Ala Lys Leu Cys
1            5

(2) INFORMATION FOR SEQ ID NO:187:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide

```
    (ix) FEATURE:
          (A) NAME/KEY: Modified-site
          (B) LOCATION: 1
          (D) OTHER INFORMATION: /product= "OTHER"
                /label= Hc
                /note= "homocysteine"

(xi) SEQUENCE DESCRIPTION: SEQ ID NO:187:

Xaa Leu Gly Val Leu Lys Leu Cys
1               5

(2) INFORMATION FOR SEQ ID NO:188:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
                /label= Hc
                /note= "homocysteine"

(xi) SEQUENCE DESCRIPTION: SEQ ID NO:188:

Xaa Leu Gly Val Leu Ala Leu Cys
1               5

(2) INFORMATION FOR SEQ ID NO:189:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
                /label= Hc
                /note= "homocysteine"

(xi) SEQUENCE DESCRIPTION: SEQ ID NO:189:

Xaa Leu Gly Val Leu Ala Lys Cys
1               5

(2) INFORMATION FOR SEQ ID NO:190:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
                /label= Hc
                /note= "homocysteine"

(xi) SEQUENCE DESCRIPTION: SEQ ID NO:190:
```

```
Xaa Val Leu Ala Lys Leu Cys
1               5
```

(2) INFORMATION FOR SEQ ID NO:191:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:191:

```
Xaa Leu Ala Lys Leu Cys
1               5
```

(2) INFORMATION FOR SEQ ID NO:192:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:192:

```
Xaa Leu Ala Lys Cys
1               5
```

(2) INFORMATION FOR SEQ ID NO:193:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(ix) FEATURE:
        (A) NAME/KEY: Modified-site
        (B) LOCATION: 9
        (D) OTHER INFORMATION: /product= "OTHER"
            /label= Pe
            /note= "penicillamine"

(xi) SEQUENCE DESCRIPTION: SEQ ID NO:193:

```
Xaa Leu Gly Val Leu Gly Lys Leu Xaa
1               5
```

(2) INFORMATION FOR SEQ ID NO:194:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(ix) FEATURE:
        (A) NAME/KEY: Modified-site
        (B) LOCATION: 9
        (D) OTHER INFORMATION: /product= "OTHER"
            /label= dPe
            /note= "D-penicillamine"

(xi) SEQUENCE DESCRIPTION: SEQ ID NO:194:

Xaa Leu Gly Val Leu Gly Lys Leu Xaa
1               5

(2) INFORMATION FOR SEQ ID NO:195:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Pe
            /note= "penicillamine"

(ix) FEATURE:
        (A) NAME/KEY: Modified-site
        (B) LOCATION: 9
        (D) OTHER INFORMATION: /product= "OTHER"
            /label= Hc
            /note= "homocysteine"

(xi) SEQUENCE DESCRIPTION: SEQ ID NO:195:

Xaa Leu Gly Val Leu Gly Lys Leu Xaa
1               5

(2) INFORMATION FOR SEQ ID NO:196:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= dPe
            /note= "D-penicillamine"

(ix) FEATURE:

(A) NAME/KEY: Modified-site
                    (B) LOCATION: 9
                    (D) OTHER INFORMATION: /product= "OTHER"
                          /label= Hc
                          /note= "homocysteine"

(xi) SEQUENCE DESCRIPTION: SEQ ID NO:196:

Xaa Leu Gly Val Leu Gly Lys Leu Xaa
1               5

(2) INFORMATION FOR SEQ ID NO:197:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: group(1, 9)
          (D) OTHER INFORMATION: /product= "OTHER"
                /label= dPe
                /note= "D-penicillamine"

(xi) SEQUENCE DESCRIPTION: SEQ ID NO:197:

Xaa Leu Gly Val Leu Gly Lys Leu Xaa
1               5

(2) INFORMATION FOR SEQ ID NO:198:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
                /label= dHc
                /note= "D-homocysteine"

(xi) SEQUENCE DESCRIPTION: SEQ ID NO:198:

Xaa Leu Gly Val Leu Gly Lys Leu Cys
1               5

(2) INFORMATION FOR SEQ ID NO:199:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
                /label= dHc
                /note= "D-homocysteine"

(ix) FEATURE:
          (A) NAME/KEY: Modified-site
          (B) LOCATION: 9
          (D) OTHER INFORMATION: /product= "OTHER"

```
                /label= dC
                /note= "D-cysteine"

(xi) SEQUENCE DESCRIPTION: SEQ ID NO:199:

Xaa Leu Gly Val Leu Gly Lys Leu Xaa
1               5

(2) INFORMATION FOR SEQ ID NO:200:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
                /label= Hc
                /note= "homocysteine"

(ix) FEATURE:
        (A) NAME/KEY: Modified-site
        (B) LOCATION: 9
        (D) OTHER INFORMATION: /product= "OTHER"
                /label= dC
                /note= "D-cysteine"

(xi) SEQUENCE DESCRIPTION: SEQ ID NO:200:

Xaa Leu Gly Val Leu Gly Lys Leu Xaa
1               5

(2) INFORMATION FOR SEQ ID NO:201:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
                /label= By
                /note= "butyroyl"

(ix) FEATURE:
        (A) NAME/KEY: Modified-site
        (B) LOCATION: 9
        (D) OTHER INFORMATION: /product= "OTHER"
                /label= Hc
                /note= "homocysteine"

(xi) SEQUENCE DESCRIPTION: SEQ ID NO:201:

Xaa Leu Gly Val Leu Gly Lys Leu Xaa
1               5

(2) INFORMATION FOR SEQ ID NO:202:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide
```

```
    (ix) FEATURE:
         (A) NAME/KEY: Modified-site
         (B) LOCATION: 1
         (D) OTHER INFORMATION: /product= "OTHER"
             /label= By
             /note= "butyroyl"

(xi) SEQUENCE DESCRIPTION: SEQ ID NO:202:

Xaa Leu Gly Val Leu Gly Lys Leu Cys
1               5

(2) INFORMATION FOR SEQ ID NO:203:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /label= Pp
             /note= "proprionyl"

(ix) FEATURE:
         (A) NAME/KEY: Modified-site
         (B) LOCATION: 9
         (D) OTHER INFORMATION: /product= "OTHER"
             /label= Hc
             /note= "homocysteine"

(xi) SEQUENCE DESCRIPTION: SEQ ID NO:203:

Xaa Leu Gly Val Leu Gly Lys Leu Xaa
1               5

(2) INFORMATION FOR SEQ ID NO:204:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /label= Pp
             /note= "proprionyl"

(xi) SEQUENCE DESCRIPTION: SEQ ID NO:204:

Xaa Leu Gly Val Leu Gly Lys Leu Cys
1               5

(2) INFORMATION FOR SEQ ID NO:205:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 1
```

(D) OTHER INFORMATION: /product= "OTHER"
                /label= Hc
                /note= "homocysteine"

(xi) SEQUENCE DESCRIPTION: SEQ ID NO:205:

Xaa Leu Gly Val Leu Gly Lys Leu Cys
1               5

(2) INFORMATION FOR SEQ ID NO:206:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:206:

Ser Leu Gly Val Leu Gly Lys Leu Ser
1               5

(2) INFORMATION FOR SEQ ID NO:207:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:207:

Cys Leu Gly Val Ala Gly Lys Leu Cys
1               5

(2) INFORMATION FOR SEQ ID NO:208:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:208:

Cys Leu Gly Val Leu Gly Ala Leu Cys
1               5

(2) INFORMATION FOR SEQ ID NO:209:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:209:

GGGCTGGACC CNNKCCGGGG GCTGCTG                                               27

(2) INFORMATION FOR SEQ ID NO:210:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:210:

GGGTCCAGCC CCGT                                                            14

(2) INFORMATION FOR SEQ ID NO:211:

(i) SEQUENCE CHARACTERISTICS:
　　　　　(A) LENGTH: 10 base pairs
　　　　　(B) TYPE: nucleic acid
　　　　　(C) STRANDEDNESS: single
　　　　　(D) TOPOLOGY: linear (xi) SEQUENCE DESCRIPTION: SEQ ID NO:211:

CAGCCCCCGG                                                                 10

(2) INFORMATION FOR SEQ ID NO:212:

(i) SEQUENCE CHARACTERISTICS:
　　　　　(A) LENGTH: 10 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO:212:

Gly Ile Leu Ala Leu Asp Tyr Val Gly Gly
1               5                   10

(2) INFORMATION FOR SEQ ID NO:213:

(i) SEQUENCE CHARACTERISTICS:
　　　　　(A) LENGTH: 10 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO:213:

Gly Ile Leu Thr Ile Asp Asn Leu Gly Gly
1               5                   10

(2) INFORMATION FOR SEQ ID NO:214:

(i) SEQUENCE CHARACTERISTICS:
　　　　　(A) LENGTH: 10 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO:214:

Gly Ile Leu Leu Asn Glu Phe Ala Gly Gly
1               5                   10

(2) INFORMATION FOR SEQ ID NO:215:

(i) SEQUENCE CHARACTERISTICS:
　　　　　(A) LENGTH: 12 amino acids
　　　　　(B) TYPE: amino acid
　　　　　(C) STRANDEDNESS: single
　　　　　(D) TOPOLOGY: linear (ii) MOLECULE TYPE: peptide (xi) SEQUENCE DESCRIPTION: SEQ ID NO:215:

Gly Pro Cys Leu Ile Leu Ala Pro Asp Arg Cys Gly

-continued

```
1               5                   10

(2) INFORMATION FOR SEQ ID NO:216:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:216:

Gly Pro Cys Ile Leu Leu Ala Arg Asp Arg Cys Gly
1               5                   10
```